(12) United States Patent
Mulcahey et al.

(10) Patent No.: US 11,446,075 B2
(45) Date of Patent: Sep. 20, 2022

(54) METHOD AND SYSTEM FOR CONSISTENT, REPEATABLE, AND SAFE CRYOSPRAY TREATMENT OF AIRWAY TISSUE

(71) Applicant: CSA Medical, Inc., Lexington, MA (US)

(72) Inventors: Thomas Mulcahey, Belmont, MA (US); Marc Davidson, Andover, MA (US); Brian M. Hanley, Reading, MA (US); Ellen E. Sheets, Boston, MA (US); Wei Li Fan, Boston, MA (US)

(73) Assignee: CSA Medical, Inc., Lexington, MA (US)

( * ) Notice: Subject to any disclaimer, the term of this patent is extended or adjusted under 35 U.S.C. 154(b) by 994 days.

(21) Appl. No.: 15/846,741

(22) Filed: Dec. 19, 2017

(65) Prior Publication Data
US 2018/0110556 A1    Apr. 26, 2018

Related U.S. Application Data

(63) Continuation of application No. 14/809,826, filed on Jul. 27, 2015, now Pat. No. 9,867,648, which is a
(Continued)

(51) Int. Cl.
*A61B 18/02*   (2006.01)
*A61B 90/98*   (2016.01)
*A61B 18/00*   (2006.01)

(52) U.S. Cl.
CPC .......... *A61B 18/0218* (2013.01); *A61B 90/98* (2016.02); *A61B 2018/00041* (2013.01);
(Continued)

(58) Field of Classification Search
CPC ........ A61B 18/0218; A61B 2018/0212; A61B 2018/00642; A61B 2018/00744;
(Continued)

(56) References Cited

U.S. PATENT DOCUMENTS 6,027,499 A * 2/2000 Johnston ............ A61B 18/0218
600/104
6,413,255 B1   7/2002 Stern
(Continued)

FOREIGN PATENT DOCUMENTS

DE   102017130107 A1   6/2019
EP       1089780 A1   4/2001
(Continued)

OTHER PUBLICATIONS

S. Smith, "The Scientists and Engineer's Guide to Digital Signal Processing", Jan. 1, 1999, California Technical Publishing, pp. 277-284.
(Continued)

*Primary Examiner* — Jaymi E Della
*Assistant Examiner* — Sean W Collins
(74) *Attorney, Agent, or Firm* — Goodwin Procter LLP

(57) ABSTRACT

A method and system for automated and semi-automated predictable, consistent, safe, effective, and lumen-specific and patient-specific cryospray treatment of airway tissue in which treatment duration is automatically set by the system following entry of patient information and treatment location information into the system by the user, and treatment spray is automatically stopped by the system when the automatically selected treatment duration has been achieved as determined by the system.

20 Claims, 36 Drawing Sheets

Related U.S. Application Data continuation of application No. 14/731,359, filed on Jun. 4, 2015, now Pat. No. 10,492,843.

(60) Provisional application No. 62/007,518, filed on Jun. 4, 2014, provisional application No. 62/047,936, filed on Sep. 9, 2014.

(52) U.S. Cl.
CPC ........... *A61B 2018/00172* (2013.01); *A61B 2018/00541* (2013.01); *A61B 2018/00577* (2013.01); *A61B 2018/00642* (2013.01); *A61B 2018/00714* (2013.01); *A61B 2018/00744* (2013.01); *A61B 2018/00761* (2013.01); *A61B 2018/00791* (2013.01); *A61B 2018/00863* (2013.01); *A61B 2018/00988* (2013.01); *A61B 2018/0212* (2013.01); *A61B 2018/0231* (2013.01)

(58) Field of Classification Search
CPC .......... A61B 2018/00863; A61B 18/02; A61B 2018/0225; A61B 2018/0293
See application file for complete search history.

(56) References Cited

U.S. PATENT DOCUMENTS

| | | | |
|---|---|---|---|
| 7,594,925 | B2 | 9/2009 | Danek et al. |
| 7,995,816 | B2 | 8/2011 | Roger et al. |
| 8,322,335 | B2 | 12/2012 | Barry |
| 9,144,449 | B2 | 9/2015 | Burr et al. |
| 9,226,648 | B2 | 1/2016 | Saadat et al. |
| 2005/0027289 | A1 | 2/2005 | Castellano et al. |
| 2005/0261674 | A1 | 11/2005 | Nobis et al. |
| 2006/0200076 | A1 | 9/2006 | Gonzalez |
| 2007/0123958 | A1 | 5/2007 | Laufer |
| 2007/0156125 | A1 | 7/2007 | Delonzor |
| 2009/0299356 | A1 | 5/2009 | Watson |
| 2009/0143640 | A1 | 6/2009 | Saadat et al. |
| 2009/0192505 | A1* | 7/2009 | Askew ............. A61M 16/0463 606/21 |
| 2009/0209943 | A1 | 8/2009 | Marsman |
| 2010/0042087 | A1* | 2/2010 | Goldboss .......... A61B 18/0218 606/22 |
| 2010/0081971 | A1 | 4/2010 | Allison |
| 2011/0306958 | A1* | 12/2011 | Berzak ................ A61B 18/02 606/24 |
| 2012/0015587 | A1 | 1/2012 | Leishman et al. |
| 2012/0035601 | A1 | 2/2012 | Wittenberger |
| 2013/0211393 | A1 | 8/2013 | Barry |
| 2015/0009460 | A1 | 1/2015 | Jang et al. |
| 2015/0066005 | A1 | 3/2015 | Fan et al. |
| 2015/0094607 | A1* | 4/2015 | Barry ................... A61B 34/10 600/538 |
| 2015/0119868 | A1* | 4/2015 | Lalonde ............... A61B 18/02 606/21 |
| 2015/0202003 | A1 | 7/2015 | Wolf et al. |
| 2016/0125161 | A1 | 5/2016 | Sankaran et al. |
| 2017/0119258 | A1 | 5/2017 | Kotanko et al. |
| 2017/0209218 | A1* | 7/2017 | Sahay .................. A61B 34/25 |

FOREIGN PATENT DOCUMENTS

| | | |
|---|---|---|
| GB | 1108905 A | 4/1968 |
| JP | 2001520541 A | 10/2001 |
| JP | 2003503123 A | 1/2003 |
| JP | 2005534460 A | 11/2005 |
| JP | 2008538524 A | 10/2008 |
| JP | 2009500052 A | 1/2009 |
| JP | 2010505527 A | 2/2010 |
| JP | 2010528815 A | 8/2010 |
| JP | 2011520513 A | 7/2011 |
| JP | 2011520536 A | 7/2011 |
| JP | 2012196389 | 10/2012 |
| JP | 2016508820 A | 3/2016 |
| WO | 1998052479 A1 | 11/1998 |
| WO | 9966970 A1 | 12/1999 |
| WO | 2001001049 A1 | 1/2001 |
| WO | 0232334 A1 | 4/2002 |
| WO | 2006053308 A2 | 5/2006 |
| WO | 2009140067 A1 | 11/2009 |
| WO | 2010007954 A1 | 1/2010 |
| WO | 2011056684 A2 | 5/2011 |
| WO | 2015188013 A1 | 12/2015 |

OTHER PUBLICATIONS

European Search Report dated (Jan. 1, 2018) for 15803402.5 (10 pages).
Supplementary Partial European Search Report dated (Dec. 19, 2016), for 13877095.3 (5 pages).
Non-Final Office Action issued in corresponding Japanese application No. JP2014/560134 dated Dec. 20, 2016.
Penultimate Office Action dated Feb. 19, 2020 for Japanese application No. 2018-152432, 14 pages.
European Search Opinion for European Patent Application No. 21201198.5 dated Apr. 2, 2022, 5 pages.
Office Action for Japanese Patent Application No. 2015-561321 dated Apr. 9, 2018, 5 pages.
Extended European Search Report for Application No. EP20216715.1, dated Jul. 8, 2021, 10 pages.
International Search Report and Written Opinion for International application No. PCT/US2020/055674, dated Feb. 9, 2021, 10 pages.

\* cited by examiner

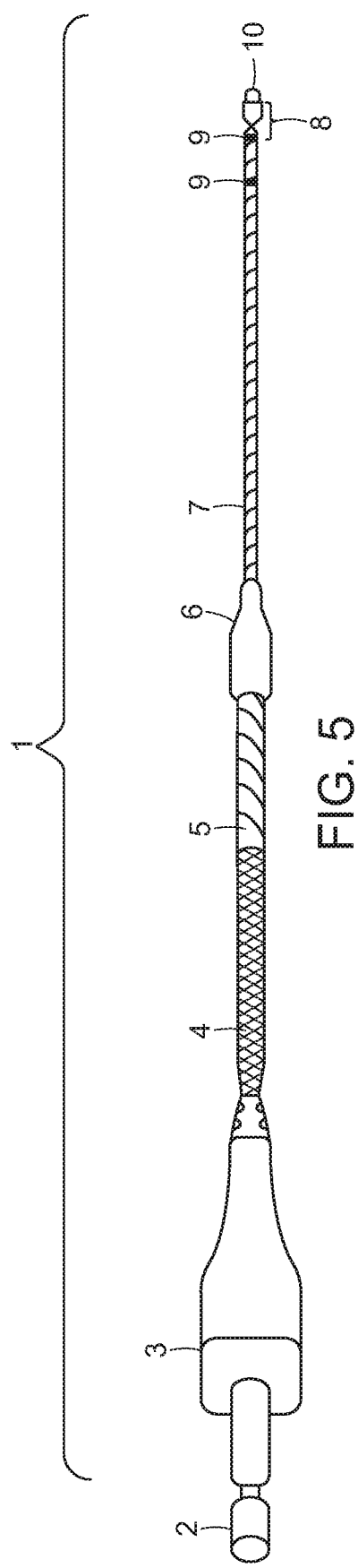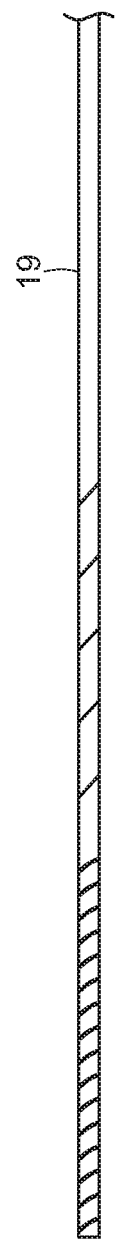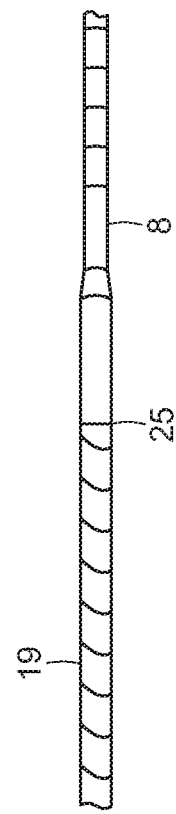

| Options ▼ | LN₂ OK |

Procedure Settings

Therapy ID

Is this procedure a new therapy or a continuation of a therapy?

| New | Continuation |

The new Therapy ID will be
20150409T120045
(Custom ID)

Gender
| Male | Female |

Lung Terminology
| Short (e.g. RB1) | Long (e.g. Apical) |

Select Procedure Settings

| Cancel |

| Options ▼ | LN₂ OK |

Procedure Settings

Therapy ID

Is this procedure a new therapy or a continuation of a therapy?

| New | Continuation |

The new Therapy ID
20150409T120045
(Custom ID)

Gender
| Male | Female |

Lung Technology
| Short (e.g. RB1) | Long (e.g. Apical) |

Confirm Settings with Physician
Then press OK to proceed to Catheter Setup

| OK |
| Cancel |

FIG. 13F

| Options ▼ | Therapy ID: 20150409T120045 | LN₂ OK |

Catheter Setup

① Scan Catheter
Hold catheter pouch to RFID Pad to scan

Scan Catheter

[ Cancel ]

FIG. 13G

| Options ▼ | Therapy ID: 20150409T120045 | LN₂ OK |

Catheter Setup

✓ Scan Catheter
Catheter ID: 2543864508

[ Rescan Catheter ]

② Connect Catheter

③ Connect Thermocouple

Connect Catheter and Thermocouple
Or Press Rescan Catheter

[ Back ]

FIG. 13H

Catheter Setup

- ✓ Scan Catheter
  Catheter ID: 2543864508
  [Rescan Catheter]
- ✓ Connect Catheter
- (3) Connect Thermocouple

Connect Thermocouple
Or Press Rescan Catheter    [Back]

Options ▼ | 03:00 | Therapy ID: 20150409T120045 | LN₂ OK

Catheter Setup

- ✓ Scan Catheter
  Catheter ID: 2543864508
  [Rescan Catheter]
- ✓ Connect Catheter
- ✓ Connect Thermocouple

Press OK to continue to the Procedure
Or Press Rescan Catheter    [OK] [Back]

FIG. 13J

Offset Control:
CSA: .0035in$^2$

2X3X020 Oblong
CSA: .0035in$^2$

2X3X028 Oblong
CSA: .0070in$^2$

2X8X016
CSA: .0035in$^2$

3X6X022
CSA: .0070in$^2$

4X8X016
CSA: .0070in$^2$

Uniform circumferental /
radial pattern

Uniform circumferental /
radial pattern

Quadrant Effect, Scalloping

Quadrant Effect, Scalloping

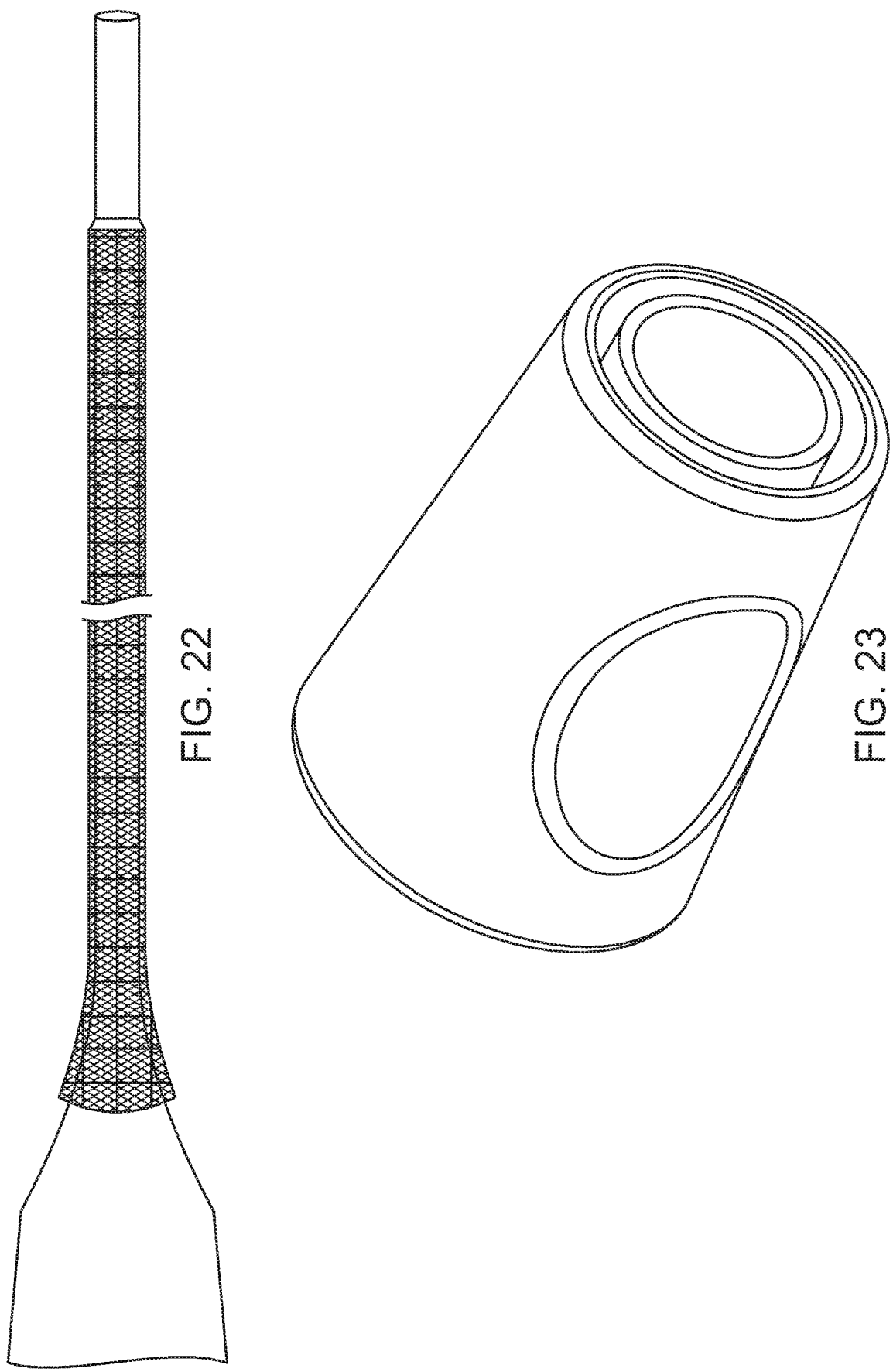

METHOD AND SYSTEM FOR CONSISTENT, REPEATABLE, AND SAFE CRYOSPRAY TREATMENT OF AIRWAY TISSUE

CROSS-REFERENCE TO RELATED APPLICATIONS

This application is a continuation of application Ser. No. 14/809,826, filed Jul. 27, 2015, which is a Continuation of application Ser. No. 14/731,359, filed Jun. 4, 2015, which claims priority under 35 U.S.C. § 119 to U.S. Provisional Patent Application No. 62/007,518 by Maners, et al. titled "Method and System For Consistent, Repeatable, and Safe Cryospray Treatment of Airway Tissue" and filed Jun. 4, 2014 and to U.S. Provisional Patent Application No. 62/047,936 by Hanley et al. titled "Bronchoscopic Sheath For Measuring or Spacing" and filed Sep. 9, 2014. Each of the foregoing applications is incorporated by reference in its entirety and for all purposes.

FIELD OF THE INVENTION

The present invention relates to medical devices for treating pulmonary diseases, more specifically to cryospray devices.

BACKGROUND OF THE INVENTION

The conducting airways of humans are lined by a superficial layer of epithelial cells which comprise an important primary line of defense to the entire respiratory tract. This superficial cellular layer consists primarily of mucus-producing (goblet) cells and ciliated cells. These cells function in a coordinated fashion to entrap inhaled biological and inert particulates and remove them from the airways. While this "mucociliary escalator" functions with great efficiency in the face of potentially injurious stimuli, it is a delicately balanced system relying on maintenance of appropriate complements of ciliated and mucus-producing cells and the normal functioning of those cells to accomplish effective clearance. Perturbations in epithelial cell type distribution and function can lead to adverse health effects.

Ciliated cells represent approximately 80% of the epithelial cells residing on luminal borders of the large airways. While they are the most prevalent epithelial cell type lining the airways, many studies suggest that they also are among the most vulnerable to injury by infection, irritant, and pollutant exposure. The identifying characteristic of ciliated cells, are the highly organized appendages of the cell, i.e., the cilia which cover the luminal border.

Mucus and other non-ciliated cells represent approximately 20% of the epithelial cells lining the luminal borders of the large airways. Mucus cells often are distended with secretory product and exhibit a characteristic "goblet" shape. Together with the submucosal glands, goblet cells secrete high molecular weight mucus glycoproteins (mucins). Goblet cells are thought to have the potential to produce markedly more mucus than do the glands, especially in response to injury such as environmental pollutants and other noxious elements such as tobacco/cigarette smoke.

Other non-ciliated cells with fewer or no granules also may be present along the luminal border. These may represent mucus cells which have emptied their contents onto the luminal surface or cells which have not yet differentiated. The entire epithelial layer sits on a basement lamina comprised of collagen and connective tissue. All the cells of the epithelial layer are anchored to this "basement membrane."

Chronic bronchitis is a non-infectious inflammatory disease typically resulting from airway injury due to a noxious element (usually smoking). It is defined by cough with productive sputum of three months duration for two consecutive years. It is further characterized by excess mucus (mucus hyperactivity/hypersecretion/hyperplasia of goblet cells) in the bronchi, damage to cilia and loss of ciliated cells. Noxious stimuli lead to airway inflammation with swelling of the lamina propria leading to thickening of the airway wall, and this functional narrowing causes shortness of breath. More specifically, this injury causes over-proliferating goblet cells to over-produce a thick viscous, acidic mucus which is difficult to clear due to cilia dysfunction. The acidic mucous in chronic bronchitis leads to inflammation of the airway wall and varies in viscosity.

Asthma is a chronic respiratory disease characterized by bronchial inflammation, increased airway smooth muscle and airway hyper-responsiveness, in which airways narrow (constrict) excessively or too easily in response to a stimulus. Asthma episodes or attacks cause narrowing/constriction of the airways, which makes breathing difficult. Asthma attacks may occur at irregular intervals and be triggered by allergens or irritants that are inhaled into the lungs or by stress, cold air, viral infections or other stimuli. Asthma is sometimes, but not always, associated with mucus hyperactivity.

Airway hypersecretion is a feature of other airway diseases as well, including chronic obstructive pulmonary disease (COPD), cystic fibrosis, viral bronchitis, and bronchiolitis.

In an individual suffering from hypersecretion, mucus accumulates in the airways and may cause airway obstruction. Airway submucosal glands and goblet cells lining the airway epithelium secrete mucus, an adhesive, viscoelastic gel composed of water, carbohydrates, proteins, and lipids. In a healthy individual, mucus is a primary defense against inhaled foreign particles and infectious agents and is cleared by active columnated cilial cells/movement which assists in clearing the mucus in an upward direction where it is either swallowed or eliminated via a productive cough. Mucus traps these particles and agents and facilitates their clearance while also preventing tissues from drying out. Small airways that contain goblet cells as well as peripheral airways and which cannot be cleared by cough are particularly vulnerable to mucus accumulation and gradual obstruction by mucus.

Conventional treatments for individuals suffering from airway hypersecretion or chronic bronchitis include use of systemic or inhaled corticosteroids, anticholinergics, antibiotic therapy, bronchodilators (e.g., methylxanthines), short or long-acting beta2-agonists which relax the muscles in the airways to relieve symptoms, aerosol delivery of "mucolytic" agents (e.g., water, hypertonic saline solution), and oral administration of expectorants (e.g., guaifenesin). It should be noted that while these medications are variably approved by the FDA for use in COPD they are not specific for chronic bronchitis with the exception of roflumilast, an inhibitor of an enzyme called phosphodiesterase type 4 (PDE-4).

Many of the above described medications have serious side effects. For example, inhaled corticosteroids can cause thrush (a yeast infection of the mouth), cough, or hoarseness, and systemic corticosteroids have even more severe side effects, such as delayed sexual development, changes in menstrual cycle, weight gain, and increased blood sugar (diabetes). The side effects of methylxanthines include severe nausea, tremors, muscle twitching, seizures, and irregular heartbeat. Roflumilast commonly induces significant diarrhea. Patient compliance is often low due to these side-effects.

Interventional approaches to managing occluded airways include surgery, mechanical debulking, brachytherapy, stents, photodynamic therapy, and thermal modalities, such as electrocautery, laser, argon plasma coagulation, and bronchial thermoplasty. Bronchial thermoplasty is a procedure designed to help control severe asthma by reducing the mass of airway smooth muscle by delivering thermal energy to the airway wall, heating the tissue in a controlled manner. Bronchial thermoplasty with RF energy creates a deep ablation effect down to the level of the airway smooth muscle creating a reparative healing that results in scar tissue which is fibrotic in nature. Hyper-thermal treatment denatures proteins, and causes enzyme inactivation and prevents collagen remodeling. Accordingly, bronchial thermoplasty patients cannot be re-treated in the same areas. Cryoprobes have also been used in airway management, but their use can be tedious and time-consuming because of surface area limitations of the probes, which requires contact between the probe and the surface of the targeted lesion or tissue.

Reports of promising results from use of low-pressure spray cryotherapy for ablation of esophageal lesions (Barrett esophagus, dysplasia and esophageal cancers) led Krimsky, et al. to gauge the safety of using cryospray in airway tissues. Krimsky, et al., 2009. Krimsky, et al., reported performing spray cryotherapy on 21 subjects who were scheduled for lung resection for treatment of lung cancer, carcinoid tumor and mycobacterial infection. Treatment areas were directed to normal and unrestricted portions of the airway distal to planned anastomotic sites. All sites received a targeted delivery of low-pressure (2-3 psi) liquid nitrogen of identical dosimetry, 2 cycles of 5-second spray with a 60-second interval thaw. All patients had treatment times shorter than 5 minutes. Post-treatment bronchoscopic and histologic examinations of airways were conducted from less than 1 day to 106 days after treatment.

Findings from the treated areas revealed varying levels of cryonecrosis, limited to the mucosal and submucosal layers (approximately 1.5 mm), and changes consistent with recent tissue injury with no damage to connective tissue. Krimsky, et al. reported loss of epithelium and airway smooth muscle, edema, and damaged submucosal glands at early time points post-treatment, followed by adjacent re-epithelialization and healing centrally from the margin of the injury. Complete re-epithelialization of the airway mucosa and a thinned or absent smooth muscle layer, as well as some continued thinning of the submucosal glands was reported to persist to 106 days after treatment.

Krimsky, et al. reported that these initial safety and histologic assessments suggested that spray cryotherapy may be safe and conducive to treatment of the airways by causing focal injury to the cellular elements of treated tissue without damage to underlying connective tissue, i.e., the extracellular matrix. Acknowledging the small number of the subjects in the study, and particularly noting that only normal, unobstructed airways were treated, Krimsky et al. nevertheless posited that the results of that study suggest treatment possibilities in human thoracic diseases.

Notably, in addition to only treating healthy unobstructed tissue (no treatment of regions characterized by excess goblet cells, hypersecretion, or damaged or lost cilia), Krimsky, et al. reported no observations concerning mucous production, goblet cell population or proliferation, and or cilia/ciliated cell population, either pre- or post-treatment. Additionally, Krimsky et al. made no observations or suggestions that cryospray treatment can actually cause change in architecture of diseased/damaged tissue, and no suggestion that diseased sections could be regenerated as healthy tissue. Moreover, there have been no published studies since Krimsky, et al. that have addressed these questions. Indeed, as of this writing, there are no medications or devices today that propose reduction in mucous secreting cells, and/or remodeling of cilia.

SUMMARY OF THE INVENTION

Cryospray methods and devices of the prior art, while effective to provide approximate cryospray amounts for approximate cryospray durations, are not configured to deliver precise and consistent cryospray doses from device to device, and even from use to use by the same user using the same device. Yet the prior art cryospray devices and methods have met a long-felt need in the industry, and excellent treatment results have been reported from the use of prior art cryospray devices. According to current cryospray devices and methods, the spray pedal is pressed, the surgeon waits for the cryospray to travel through the system and delivery catheter to exit the catheter tip, observes the cryospray application to the desired tissue through the endoscope or bronchoscope, continues the spray until the treated tissue turns white, generally recognized as indicating that the tissue has achieved a frozen state, then manually continues on with the spray for a measured amount of time such as five or up to ten seconds. The flow of cryogen is immediately stopped by the treating physician releasing the pedal. The treated tissue is allowed to thaw, then the treatment is repeated in the same fashion, if desired. In short, current cryospray devices and methods are designed to ablate tissue, and the amount of cryospray applied varies from patient to patient, and surgeon to surgeon, based on the surgeon's observation of the change in tissue during treatment, making a subjective assessment concerning progress of the treatment and making a subjective determination concerning whether additional treatment of the treated area is indicated. Surgeons and other users of the prior art cryospray devices and methods are trained and comfortable with the current method of cryospray, and are reporting excellent results. Accordingly, there has been no need perceived in the art for a cryospray method or device that performs differently than the prior art cryospray methods and devices.

Notwithstanding the foregoing, and even taking into account the expertise and experience of surgeon users, the inventors have discovered that treatment of a superficial depth of tissue in airways that do not have obstructions from excess tissue, tumors or fibrotic tissue, for the purpose of triggering tissue regeneration requires cryospray devices and methods that provide automated or semi-automated cryospray application to airway tissue that is predictable, consistent and repeatable, from application to application and from device to device, and that is specifically and individually tailored to each patient and to each segment of airway tissue. In order to provide such predictable, consistent, and repeatable cryospray application (the need for which was not previously appreciated in the art), the inventors developed the devices and methods described herein.

According to the invention, therefore, the present invention is a method and system for automated and semi-automated predictable, consistent, effective, lumen-specific dose(s) and patient-specific cryospray extended treatment of airway tissue, across one or more treatment sessions.

According to one embodiment of the invention, treatment duration is automatically set by the system following entry of patient information and treatment location information into the system by the user, and treatment spray is automatically stopped by the system when the automatically selected treatment duration has been achieved as determined by the system. According to another embodiment of the invention, different treatment durations are automatically set for different treatment locations in the airway based on treatment site luminal diameter. According to another embodiment of the invention, treatment spray cannot occur until a user enters patient information and treatment location into the system console.

According to another embodiment of the system, the device is configured to maintain the cryospray supply line between the onboard cryogen tank and the delivery catheter port at a constant temperature during cryospray operation. According to a preferred embodiment, the cryospray supply line between the cryogen tank and the delivery catheter port is maintained at a constant temperature above (warmer than) −120 C, and preferably at or around 20 C using combinations of sensors and heaters at the control valves and at the end piece.

According to yet another embodiment of the invention, each individual delivery console is calibrated and tuned so that each delivery console provides a nearly identical automated dosage for each set of delivery parameters, i.e., patient information and treatment location/luminal diameter. According to this embodiment, a fully assembled and operating cryospray delivery console, already charged with cryogen, is connected to an external source of cryogen (in gaseous form) via an adjustable pressure valve. The adjustable pressure valve is used to dial in a specific and precise tank pressure. The cryospray delivery system is then operated in test mode, and that cooling power is measured at the cryospray outlet, i.e., the tip of the cryospray delivery catheter. The adjustable pressure valve is then adjusted, and the system re-tested until the desired cooling power is achieved at the outlet. Once the pressure necessary to achieve the desired cooling power has been determined, the console is tuned to set the nominal cryogen tank pressure to the determined pressure. According to this embodiment, notwithstanding variations from machine to machine due to manufacturing tolerances for tubing, valves, and other cryogen supply elements, each cryospray device according to the invention delivers the exact cryospray dose for each set of delivery parameters, i.e., patient information and luminal diameter.

According to a further embodiment of the invention, there is provided an improved cryogen delivery catheter having a proximal segment that is wider than the working channel of a corresponding bronchoscope, and a distal segment that is configured to fit within the working channel of a corresponding bronchoscope. According to yet another embodiment, treatment of airway tissue is administered circumferentially using a radial spray pattern delivery catheter configured to deliver a cryospray to the entire circumferential interior of a selected endoluminal cross-section simultaneously without having to rotate the delivery catheter. According to this embodiment, the distal end of the catheter is configured to direct cryospray radially relative to the axis of the delivery catheter, and not forward (i.e., not longitudinally, relative to the axis of the delivery catheter). According to this embodiment, the distal end of the delivery catheter is configured with exactly two rows of eight cryogen delivery ports, equally spaced around the perimeter of the catheter, the center line of the rows preferably displaced 0.025" from one-another, and each port offset from an adjacent port of the other row by 22.5°. The inventors have discovered that prior radial cryospray delivery port arrangements having more than two rows of delivery ports tend to produce a cryogen delivery pattern that extends forward, often beyond the visualization limits of the bronchoscope. Moreover, the inventors discovered that the two, offset rows of delivery ports described herein avoid the forward traveling cryospray characterized by delivery catheters that have more than two rows of delivery ports.

These embodiments, together with others as explained in more detail herein, provide an automated and semi-automated predictable, consistent, safe, effective, and lumen-specific and patient-specific cryospray treatment of diseased airway tissue.

Another aspect of the present invention, therefore, is the therapeutic treatment of epithelial hyperplasia and metaplasia using the methods and devices of the present invention. The treatments can also be used, for example, therapeutically to ameliorate altered epithelial architecture in the setting of asthma, bronchitis, bronchiolitis, and/or related inflammatory and infectious disorders characterized by a similar pattern of goblet cell metaplasia and/or increased airway smooth muscle. The treatments can similarly be used to treat an airway disease or condition characterized by hypersecretion of mucus.

Disease states indicative of a need for cryospray therapy include, for example, chronic obstructive pulmonary disease, inflammatory diseases (e.g., asthma, bronchiectasis, and pulmonary fibrosis), and chronic obstructive lung diseases (e.g., chronic bronchitis).

A determination of the need for treatment may be assessed according to any number of ways, including but not limited to one or more of the following—a history and physical exam, histopathology (biopsy confirmation) consistent with over production of mucus or goblet cell proliferation (e.g., cough productive of mucous), radiographic or other imaging studies of the airways that indicate diseases or conditions with overproduction of mucous, or pulmonary function tests that indicate evidence of airway obstruction and/or hyperreactivity.

According to the present invention, a method is presented for spray cryotherapy directed to at the airway surface epithelium to destroy damaged cilia and hypersecretory goblet cells and to stimulate/or induce remodeling resulting in regenerative healing response or remodeling resulting in new tissue/cell growth, new cilia, new epithelium resulting in reduced mucous production. According to the invention, the airway tissue response to cryospray treatment is a regenerative healing response, i.e., resulting in tissue remodeling, as compared to a reparative healing response leading to scar/fibrosis. As cryospray results in a preservation of the extracellular matrix with little scarring or fibrotic tissue healing, cryospray treated regions can be re-treated in the same areas in the event that treated and remodeled tissue suffers a relapse after remodeling/regeneration.

According to an aspect of the invention, there is presented a method for cryospray treatment of damaged, inflammatory, or hypersecretory airway tissue which causes airway remodeling resulting in return of airway epithelium to healthy architecture.

According to an aspect of the invention, there is presented a method for cryospray treatment of treating airway hypersecretion which causes airway remodeling and therapeutic reduction of mucous hypersecretion.

According to an aspect of the invention, there is presented a method for cryospray treatment of damaged, inflammatory, or hypersecretory airway tissue wherein the application/delivery of cryogen is touch free.

According to an aspect of the invention, there is presented a method for cryospray treatment of damaged, inflammatory, or hypersecretory airway tissue which does not require apposition of the cryospray instrument to the target tissue.

According to an aspect of the invention, there is presented a method for cryospray treatment of damaged airway cilia.

According to an aspect of the invention, there is presented a method for cryospray treatment of chronic bronchitis.

According to an aspect of the invention, there is presented a method for cryospray treatment of asthma-associated bronchial obstruction due to mucous hyperactivity.

According to an aspect of the invention, there is presented a method for cryospray treatment of asthma-associated bronchial obstruction due to increased airway smooth muscle.

According to an aspect of the invention, there is presented a method for cryospray treatment of COPD.

According to an aspect of the invention, there is presented a method for cryospray treatment of overproduction of or hyperplasia of goblet cells in the airway.

According to an aspect of the invention, there is presented a method for using cryospray treatment to reduce production of airway mucous.

According to an aspect of the invention, there is presented a method for using cryospray treatment to reset the tissue, causing remodeling of the treated tissue to normal goblet cell count.

According to an aspect of the invention, there is presented a method for using cryospray treatment to induce regrowth of cilia.

According to an aspect of the invention, there is presented a method for using cryospray treatment to treat airway tissue which does not damage underlying connective tissue and which is less-fibrotic.

According to an aspect of the invention, there is presented a method for cryospray treatment of damaged, inflammatory or hypersecretory airway tissue comprising a predetermined dose based on endoluminal diameter/anatomic location in the bronchial tree.

According to an aspect of the invention, there is presented a method for cryospray treatment of damaged, inflammatory or hypersecretory airway tissue comprising a delivery dose that is configured to produce a limited cryonecrosis that does not extend to the underlying connective tissue. The depth of cryonecrosis increases with increased dose, in particular the length of the spray time. Since the connective tissue depth in the airway is generally related to the diameter of the vessel, this aspect of the invention includes a cryospray dose that is dependent on endoluminal diameter of anatomic location e.g. trachea, main bronchi, lobar and sub-segmental bronchi. Typical endoluminal diameters in the bronchial tree in an average adult are trachea: 18 mm; main bronchus: 12 mm; lobar bronchus: 8 mm; segmental bronchus: 6 mm. Yet the thickness of bronchial tissue layers of relevant to disease processes tends to be substantially the same irrespective of the endoluminal diameter. Accordingly, according to this aspect of the invention, systems and methods for ablation of airway tissue are provided which ablate tissues at substantially constant depths (0.1-0.5 mm) and axial extents (1-2 cm) in airways of widely varying diameter. This is achieved by delivering patient- and region-specific quantities of cryogen to the airway based on limited user inputs.

According to some embodiments within this aspect of the invention, dose time optionally follows the following guidelines:

TABLE 1

| Endoluminal Diameter/Segment | Dwell/spray Time |
|---|---|
| 18 mm/Trachea | 17 to 25 seconds |
| 12 mm/Bronchii (Primary) | 11 to 18 seconds |
| 8 mm/Lobar | 10 to 16 seconds |
| 6 mm/Segmental | 8 to 14 seconds |

According to an aspect of the invention, a treatment procedure is comprised of multiple lumen-specific doses in the lung and/or trachea. According to a preferred embodiment, treatment begins at the most distal targeted sites and progresses in a proximal direction up the respiratory tree. Each dose is applied once to targeted treatment site and allowed to thaw as the bronchoscope is navigated proximally to the next targeted site. Hand ventilation may be required with or without removing bronchoscope after a number of doses are given and oxygen levels are monitored and stabilized during treatment. Additionally, more than one treatment session (also referred to as a procedure day) may be required to complete treatment. For instance, ipsilateral bronchi may be treated on a first procedure day, while contralateral bronchi are treated on a second procedure day. Thus, embodiments according to this aspect of the present invention encompasses the delivery of multiple cryosprays (e.g. 1, 2, 3, 4, 5, 6, 7, 8, 9 or 10 or more cryosprays) to the same region, adjoining regions, or contralateral regions of the bronchial tree, in a single procedure day or in multiple procedure days (e.g. 2, 3, 4, 5, 6, 7, 8, 9, or 10 or more procedure days). In some cases, previously treated areas are retreated on subsequent treatment days to provide supplemental ablation or to ablate new tissue growth at a site of treatment According to another embodiment of the invention, a dose spacing sheath may be provided over the bronchoscope. According to this embodiment, the dose spacing sheath extends over the bronchoscope a sufficient length to cover the portion of the scope that is visible to the user/operator outside of the patient's body during use, including portions of the scope that are inside the patient's body during part of the treatment but that are withdrawn from the patient's body as progressive parts of the airway tissue are treated. The exterior of the dose spacing sheath contains markings that can be used by the operator to gage how far the scope is being moved, i.e., how far the scope is being withdrawn in order to treat a subsequent location so that doses do not overlap one-another.

Accordingly, to begin treatment, the catheter and scope is advanced to the most distal segment that will receive treatment. According to a preferred embodiment, each treatment area/location within an airway segment is treated with only a single dose. Once the first anatomical location is treated, the catheter and scope is withdrawn to a less distal anatomic location in the same or a different segment of the lung or trachea, moving in a distal to proximal direction. A dose spacing sheath placed over the bronchoscope may be used to assist the operator in showing how far the scope and catheter are moved in order to avoid overlapping doses. Depending on the new location, the dose administered may be the same as administered to the first anatomical segment or it may be different. According to one embodiment of the invention, a circumferential region of untreated tissue is left between regions of treated tissue. According to this embodiment, regions of contiguous treated tissue range from 5 mm to 15 mm in length (measured along the axis of the airway segment, and regions of intervening untreated tissue range in length from 1 mm to 5 mm.

According to an aspect of the invention, there is presented a method for cryospray treatment of damaged, inflammatory or hypersecretory airway tissue comprising low pressure cryospray to airway tissue where the pressure of the spray exiting the catheter is less than 5 psi (e.g. 4, 3, 2, 1, 0.5, 0.25 psi or less).

According to an aspect of the invention, there is presented a method for cryospray treatment of damaged, inflammatory or hypersecretory airway tissue where the cryogen exiting the delivery catheter is in the range of −150 degrees to −200 degrees Centigrade.

According to an aspect of the invention, there is presented a method for cryospray treatment of damaged, inflammatory or hypersecretory airway tissue comprising single or multiple treatment sessions whereas one or more lobes are treated in the same session e.g. a treatment may include the left lower and middle lobes and one main bronchi; and a subsequent session may include the right lobe, main bronchi and trachea.

According to an aspect of the invention, there is presented a method for cryospray treatment of damaged, inflammatory, or hypersecretory airway tissue which is effective to result in reduced mucous/sputum production and cough. Validated measures of cough-specific quality of life include but are not limited to the Cough Quality-of-Life Questionnaire (CQLQ) or St. George Respiratory Questionnaire (SGRQ). Additional tools for dyspnea associated with sputum production include but are not limited to, patient directed sputum diary cards, such as described by IS Woolhouse; and the Breathlessness, Cough and Sputum Score (BCSS©).

According to an aspect of the invention, there is presented a method for cryospray treatment of damaged, inflammatory or hypersecretory airway tissue which is effective to improve lung function by 20%, 30%, 50%, 70%, 100%, 150% or 200%, as measured by spirometry (e.g.—Forced Expiratory Volume (FEV1) or FEV1/FVC ratio). Forced Expiratory Volume (FEV1) is the amount of air a patient can blow out of his/her lungs in the first second. Forced Vital Capacity (FVC) is the largest amount of air that a patient can blow out after taking the biggest possible breath.

According to an aspect of the invention, there is presented a method for cryospray treatment of damaged, inflammatory or hypersecretory airway tissue which is effective to result in reduced symptoms including exacerbations requiring medication or hospital stay. There are several accepted measurement tools for exacerbations and symptom assessment including but not limited to, the EXACT © (The EXAcerbations of Chronic Pulmonary Disease Tool); EXACT PRO©, where PRO is an acronym for Patient-Reported Outcome, and EXACT-RS, daily diary to assess respiratory symptoms in patients with stable COPD According to a further embodiment of the invention, there is a method for cryospray treatment of damaged, inflammatory or hypersecretory airway tissue which is effective to result in the reduction of pulmonary biomarkers associated with COPD or other disease/damage.

The present invention also relates, in certain aspects, to a sheath or sleeve, designed to fit snugly over the outside surface of a bronchoscope during a bronchoscopic procedure such as a procedure according to another aspect of the present invention. The exterior surface of the sleeve bears markings at pre-determined increments to reflect distance along the length of the sheath which are designed to be used by the practitioner to help gauge and measure movement of the bronchoscope into and out of the patient's airway. The reference markings then are used to reference or align to another object such as the endotracheal tube or rigid bronchoscope.

According to one embodiment, the sheath is made of braided polymer thread/filament. The braid structure is analogous to a Chinese finger puzzle, increasing in diameter when compressed longitudinally, and collapsing/locking down when it is placed under tension. When the sheath is compressed longitudinally, the inner diameter of the sheath expands significantly more than its braided diameter, permitting it to slide over scopes or catheters of a broad range of diameters. When permitted to relax and recover to its original braided dimension, and particularly when it is placed under tension, it fits snugly on the surface of the scope. This allows the sheath to accommodate and provide insulation and reference markings for multiple scope diameters. The braided sleeve Inner Diameter (ID) is intentionally sized smaller than the Outer Diameter (OD) of the preferred bronchoscope such that it expands and fits snuggly to the scope upon insertion. Therefore, the sheath stays tightly fixed to the exterior surface of the flexible bronchoscope during use, but may be easily loaded and unloaded by pushing the ends of the sheath towards one-another, and "inch-worming" the sheath down the length of the bronchoscope shaft.

The reference markings may be printed on the exterior surface of the sheath, e.g., using a pad printer or other method, or may be braided into the sheath, for example using a different colored filament. In either event, the markings are set at defined intervals, e.g., 0.5 cm, 1.0 cm, 1.5 cm, etc. According to an embodiment of the invention, the markings may be made in one color to indicate major lengths, e.g., every 10 cm, and the markings may be made in a different color to indicate minor lengths, e.g., every 1 cm. Whatever markings are used, they may be made according to any known method.

According to an embodiment of the invention, the proximal end of the sheath may be cuffed and/or flared and/or bear a hub to facilitate loading and unloading of the sheath from a flexible bronchoscope. A hub may be a molded or machined plastic component that is joined to the braided sheath by bonding or insert molding and, optionally, secures the braided sheath to the bronchoscope, for example by means of a slidable locking mechanism that can be engaged and disengaged by a user.

According to yet another embodiment, the distal end of the sheath may be tapered and or cuffed to facilitate insertion of the sheath-mounted bronchoscope into the sealing gasket of the endotracheal tube, to provide an atraumatic end so that the sheath does not scythe the tissue when moving proximal to distal, and/or to prevent fraying and/or unravelling of the braid. In some cases, the cuff is configured to engage (reversibly or irreversibly) with an introducer element, preferably a rigid, molded or machined polymer component slidably disposable about the sheath and having a distal portion sized to interfit with a proximal portion of an endotracheal tube. When engaged with the endotracheal tube, the introducer element holds a gasket or valve in the opening of the endotracheal tube in the open position, permitting the sheath to slide freely through the gasket or valve and, consequently, through the endotracheal tube.

According to a cuffed embodiment, the cuffs at either end may be thermally formed from the braided material, or they may be formed from a different elastomeric or plastic material and fixed to the end of the braided material according to one of any number of known methods. According to an alternative embodiment, the distal end of the braided sleeve may be dipped in or otherwise coated with a flexible material to create a distal tip that is stiffer to aid with insertion into an endotracheal tube gasket, but still flexible enough to assemble onto the bronchoscope.

According to an embodiment of the invention, the bronchscopic measurement sheath is configured to extend over the flexible bronchoscope a sufficient length to cover the portion of the scope that is visible to the user/operator outside of the patient's body during use, including portions of the scope that are inside the patient's body during part of the treatment but that are withdrawn from the patient's body as progressive parts of the airway tissue are treated. A portion of the distal end of the scope may be left uncovered to avoid interruption of diagnostic and therapeutic devices or gases delivered via the bronchoscope e.g. LN2 cryospray delivery and LN2 gas egress According to an embodiment of the invention, the bronchoscopic measurement sheath provides thermal insulation of portions of the scope that are inside the patient's body during procedures such as radio frequency, laser, or cryotherapy to provide protection from thermal injury. The braided construction and mix of monofilament and multifilament fibers provide both thermal insulation and a physical barrier between the smooth surface of the bronchoscope and endothelium. As the braided construction can comprise of any combination of polymeric material, there will also be the insulating contribution provided by the polymer. According to other embodiments, the braid may be made from filaments of other compositions (e.g., polypropylene, nylon, polyester) or the braid may be made from a hybrid of filaments made from PET and other materials.

Turning now to further aspects of the present invention, in one aspect the present invention relates to a computer-moderated method for lumen-specific and gender-specific cryospray treatment of airway tissue that is preferably (though not necessarily) damaged, inflammatory, or hypersecretory. The method includes receiving, via a cryospray user-interface such as a touch-sensitive display, user inputs of patient type and anatomical airway segment to be treated, then automatically delivering a pre-determined metered cryospray of cryogen based on the patient type and airway segment entered by the user, which is initiated by a user input and ends automatically when the predetermined metered cryospray has been delivered. In various embodiments, the method does not require a cryospray instrument to be apposed to airway tissue, and the method optionally sets different cryospray doses automatically for different airway regions based on their luminal diameter. The patient type is, in some cases, gender, such that different doses are automatically set for male and female patients. Optionally or additionally, treatment spray cannot be initiated until a user has entered patient information and treatment location into the system console. The method may also involve maintaining a cryospray supply line between a cryogen tank and a delivery catheter at a constant temperature during cryospray operation, and one or more valves, manifolds, and catheter interfaces along the supply line may be held at, for example, a temperature warmer than −120° C. The metered cryospray is optionally delivered via a cryogen delivery catheter having a proximal segment that is wider than the working channel of a corresponding bronchoscope, and a distal segment that is configured to fit within the working channel of said bronchoscope, said delivery catheter configured to deliver a cryospray to the entire circumferential interior of a selected endoluminal cross-section simultaneously without having to rotate the delivery catheter, wherein a distal end of the delivery catheter is configured with exactly two rows of eight cryogen delivery ports, equally spaced around the perimeter of the catheter, the center line of the rows displaced 0.025" (0.635 mm) from one-another, and each port offset from an adjacent port of the other row by 20°-25 (e.g. 22.5°).

In another aspect, the present invention relates to an apparatus for computer-moderated cryospray of a body lumen (not limited to an airway) that includes pressure maintenance system, a cryogen level monitoring system, a catheter attachment apparatus, a fluid path pre-cool function, user-control system for user-control of cryogen flow, a display screen, a cryogen supply line between a cryogen source and said catheter attachment apparatus, a plurality of temperature sensors and heaters associated with said supply line configured to maintain said supply line at a constant temperature during cryospray treatment, and an on-board control system comprising a computer readable medium containing computer readable instructions for monitoring and controlling cryogen tank fill operation; running pre-procedure system checks; controlling fluid path pre-cool; and controlling thermal functions during user treatment of patients. In some embodiments, the control system will prompt a user to enter a patient type and an anatomical lumen segment for treatment, and will not to permit cryospray treatment until after said patient type and anatomical airway segment has been entered; the control system is optionally further configured to cause the apparatus to deliver a pre-determined dose of cryospray upon initiation by a user, based on an entered patient type and anatomical airway segment. The cryogen supply line also optionally includes a cryogen valve, a manifold having a fixed orifice for the escape of cryogen gas, a catheter valve, and a catheter interface having a fixed orifice for the escape of cryogen gas.

In yet another aspect, the present invention relates to a system with a reservoir comprising a cryogen, a fluid path between a the reservoir and a connector port for a cryospray catheter, the fluid path comprising at least one valve controllable by a processor, an input for a temperature sensor attached to a cryospray catheter, a graphical output device, a user input device, a non-transitory computer readable medium storing instructions executable by a processor; and a processor configured to (a) execute the instructions stored on the non-transitory computer readable medium, (b) receive an input from the temperature sensor, (c) deliver an output to the graphical output device, (d) receive an input from the user input device, and to (e) provide an output to the at least one valve. The instructions on the computer readable medium include several steps: receiving a user input identifying a sex of a patient and an airway region of the patient to be treated; calculating, based on the user input and on a temperature input from the cryospray catheter, an amount of cryogen to deliver to ablate an endothelial layer of the airway of the patient; and delivering, through a catheter connected to the system and into the airway region, the calculated amount of cryogen. The instructions also optionally include comparing a temperature received from the temperature sensor of the catheter to a threshold temperature selected based upon the user input of airway location; calculating a rate of change of the temperature received from the temperature sensor over a time interval and comparing the rate of change to a threshold rate of change selected based upon the user input; measuring an elapsed time from the opening of the at least one valve during the step of delivering the cryogen to the catheter and comparing the timer to a threshold time; and terminating the flow of cryogen by closing the at least one valve if at least one of the following conditions is detected: (a) the temperature received from the temperature sensor is at or below the threshold temperature, (b) the rate of change varies by a predetermined amount from the threshold rate of change, (c) the elapsed time equals or exceeds the threshold time, and (d) a user input to sustain the flow of cryogen is terminated before the elapsed time reaches 2 seconds, and/or (e) providing an output to the graphical output device if the flow of cryogen is interrupted and if neither condition (a) nor condition (c) was detected and, based upon a number of cryosprays delivered during a treatment session and a temperature output from the temperature sensor, either displaying a user prompt on the graphical output device for an additional spray or terminating the procedure.

In yet another aspect, the present invention relates to a system that includes a cryogen source in fluid communication with a cryogen delivery device, one or more adjustable pressure valves configured to adjust a pressure of the cryogen source in response to a control signal, and a controller configured to receive an indication of a target pressure, measure the pressure of the cryogen source during an operation of the cryogen delivery device, determine whether the measured pressure matches the target pressure, and send the control signal to the one or more adjustable pressure valves to adjust the pressure of the cryogen source towards the target pressure. The controller optionally determines the target pressure by (a) receiving a cooling power measurement indicative of a cooling power of the cryogen delivery device when the cryogen delivery device is delivering a cryogen, (b) receiving an indication of the cryogen source pressure when the cryogen delivery device achieves a cooling power corresponding to the cooling power measurement, identifying that the cooling power measurement matches a target cooling power, and storing the indicated cryogen source pressure as the target pressure. Steps (a) and (b) are optionally repeated until the cooling power measurement matches the target cooling power. In some cases, the adjustable pressure valves include a first valve configured to provide rough reduction in the pressure of the cryogen source and second and third valves configured to control pressure vent and pressure build functions of the cryogen source. In this arrangement, the processor optionally triggers the first valve when the pressure of the cryogen source is greater than a predetermined threshold amount, while the second and third valves are optionally responsive to a pulse width modulation controller that adjusts its duty cycle based on a control voltage provided by the control signal. The control signal may be driven by a proportional-integral-derivative (PID) control algorithm, which can optionally adjust the control signal based on the target pressure, a current rate of change of pressure, and a pressure history of the cryogen source and which is preferably (though not necessarily) configured to avoid cycling between vent and build operations.

In still another aspect, the present invention relates to a catheter for cryospray treatment of an airway with a proximal interface bayonet configured to connect to a cryospray console, an ergonomic plastic bayonet cover configured to interface with the console along with the bayonet, an insulating sheath distributed over a proximal portion of a catheter assembly configured to reside outside a working channel of a scope, a proximal tube portion comprising laser cut metal hypotube and having a diameter that exceeds the inner diameter of the working channel of said scope, and a distal tube portion comprising laser cut stainless steel hypotube having a diameter and length configured to work in the working channel of said scope. The catheter includes an outer covering in the form of a polymeric layer to cover the entire length of the catheter to provide a fluid tight lumen, and the distal tube portion terminates in a cylindrical segment including an atraumatic tip and, proximal to the tip, a plurality of cryogen delivery ports formed as circular fenestrations having a diameter of 0.015" (0.381) within the segment, the segment comprising exactly two rows of eight cryogen delivery ports, equally spaced around the perimeter of the catheter, the center line of the rows displaced 0.025" (0.635 mm) from one-another, and each port offset from an adjacent port of the other row by 22.5°. Optionally or additionally, the catheter includes a thermocouple situated at or near a distal tip of the catheter to provide temperature feedback to a cryospray console, and/or is configured to deliver cryogen to an airway in an annular region about the plurality of fenestrations. The annular region preferably has substantially uniform (e.g. uniform when examined visually) axial and radial margins. The catheter can also include multiple markings on the exterior of the catheter proximal to the distal segment, which markings are regularly spaced (e.g. separated by a defined distance such as 1.2.5 mm etc.).

In yet another aspect, the present invention relates to a method of treating a patient by ablating a lung epithelium by cooling an annular region of an airway to −20° C. to a depth no greater than 0.5 mm from an (inner or luminal) airway surface, for example by delivering a quantity of a cryogen calculated by an automated system to the annular region of the airway through a catheter, the catheter terminating in a cylindrical segment including an atraumatic tip and, proximal to the tip, a plurality of cryogen delivery ports formed as circular fenestrations within the segment, the segment comprising exactly two rows of eight cryogen delivery ports, equally spaced around the perimeter of the catheter, the center line of the rows displaced 0.025" (0.635 mm) from one-another, and each port offset from an adjacent port of the other row by 22.5° and offset from an adjacent port of the same row by 45°. The cryogen may be liquid nitrogen, and the predetermined quantity may be based in part upon the region of the airway being treated/ablated. In some cases, the catheter includes markings on its exterior surface as described above, in which case treatment includes moving the catheter by a fixed distance between applications of cryogen. As one example, a first system-calculated quantity of cryogen can be delivered to a first annular region of the airway, the catheter advanced or retracted by the fixed distance, and a second system calculated quantity of cryogen can be delivered to a second annular region of the airway adjacent to the first annular region. The second predetermined quantity of cryogen is determined based in part upon a temperature reading after delivery of the first predetermined quantity of cryogen, the reading provided by a temperature sensor disposed near the distal end of the catheter, a temperature of the second material on the exterior of the catheter.

In yet another aspect, the present invention relates to a sheath configured to be placed over the outer surface of a bronchoscope along a portion of its length during cryospray treatment of an airway or other bronchoscopic procedure, which includes an elongated tube having a lumen configured to receive a bronchoscope, a securing device at one end of said tube configured to secure the sheath to a proximal end of the bronchoscope, and a plurality of markings along a portion of the external surface of the tube configured to denote a distance that said scope is moved relative to a fixed position of a patient, a patient feature, or other fixed reference point. The markings are, variously, circumferential marker bands, outside the working channel of the scope, and/or associated with printed numbers.

And in yet another aspect, the present invention relates to a method of treating a patient by: inserting, into an airway of the patient, a bronchoscope, at least a portion of the bronchoscope being covered by a braided polymer sheath bearing a plurality of external markings separated from one another by a fixed distance, extending, through a working channel of the bronchoscope, a cryospray delivery catheter into the airway and delivering a metered cryospray to a first portion of the airway, advancing or retracting the bronchoscope a predetermined distance, using the plurality of markings on the sheath as an indicator of the predetermined distance, and delivering a metered cryospray to a second portion of the airway.

DESCRIPTION OF THE DRAWINGS

The following figures accompany the Detailed Description of the Invention which describes the methods and results of specific examples of the practice and success of the invention.

FIG. 5 is an isometric view of a radial spray catheter according to an embodiment of the invention, FIG. 6 is a side view of the steel tube proximal construction of a catheter according to the invention with a laser cut pattern that varies to adjust tube flexibility.

FIG. 7 shows a side view of one embodiment of the junction of a large I.D. hypotube to a small I.D. hypotube shaft

FIGS. 13A-L are exemplary interfaces for performing a setup procedure in accordance with exemplary embodiments.

FIGS. 16G-H illustrate cryospray delivery patterns that result from the radial spray design illustrated in FIG. 16D, while

FIG. 22 is a close-up of a bronchoscopic measurement sheath according to another embodiment of the invention, mounted on a flexible fiber-optic bronchoscope.

FIG. 23 shows a proximal end hub according to an embodiment of the invention.

DETAILED DESCRIPTION OF THE INVENTION

Cryospray Systems and Methods

Certain methods and devices described herein are improvements to the cryospray methods and devices described in co-pending U.S. patent application Ser. No. 13/784,596, filed Mar. 4, 2013, entitled "Cryosurgery System," and co-pending U.S. patent application Ser. No. 14/012,320, filed Aug. 28, 2013; each of these applications is incorporated herein by reference in its entirety and for all purposes.

Figure 1:
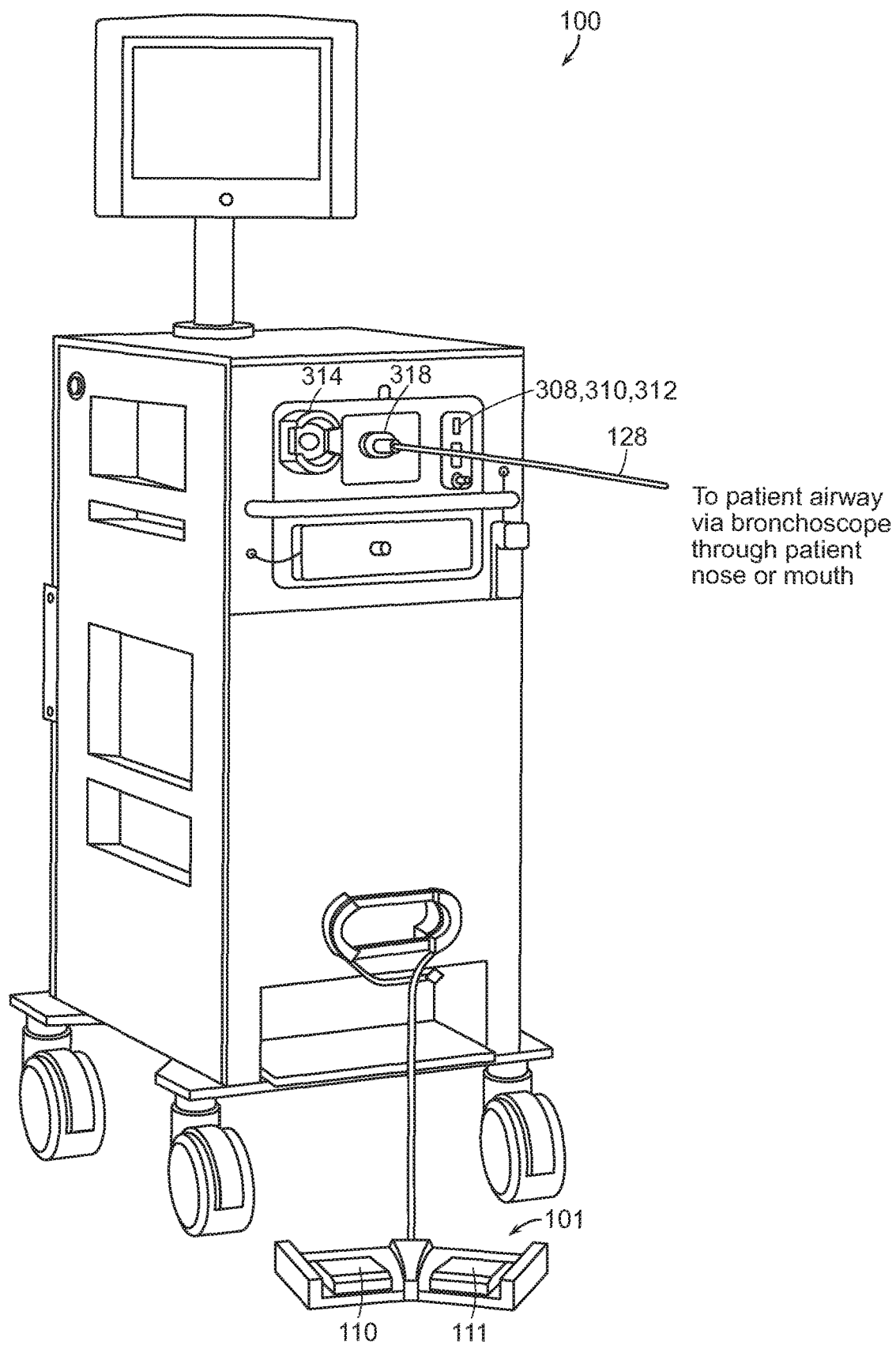
FIG. 1 is a perspective view of a cryosurgery system according to an embodiment of the invention.
Figure 2:
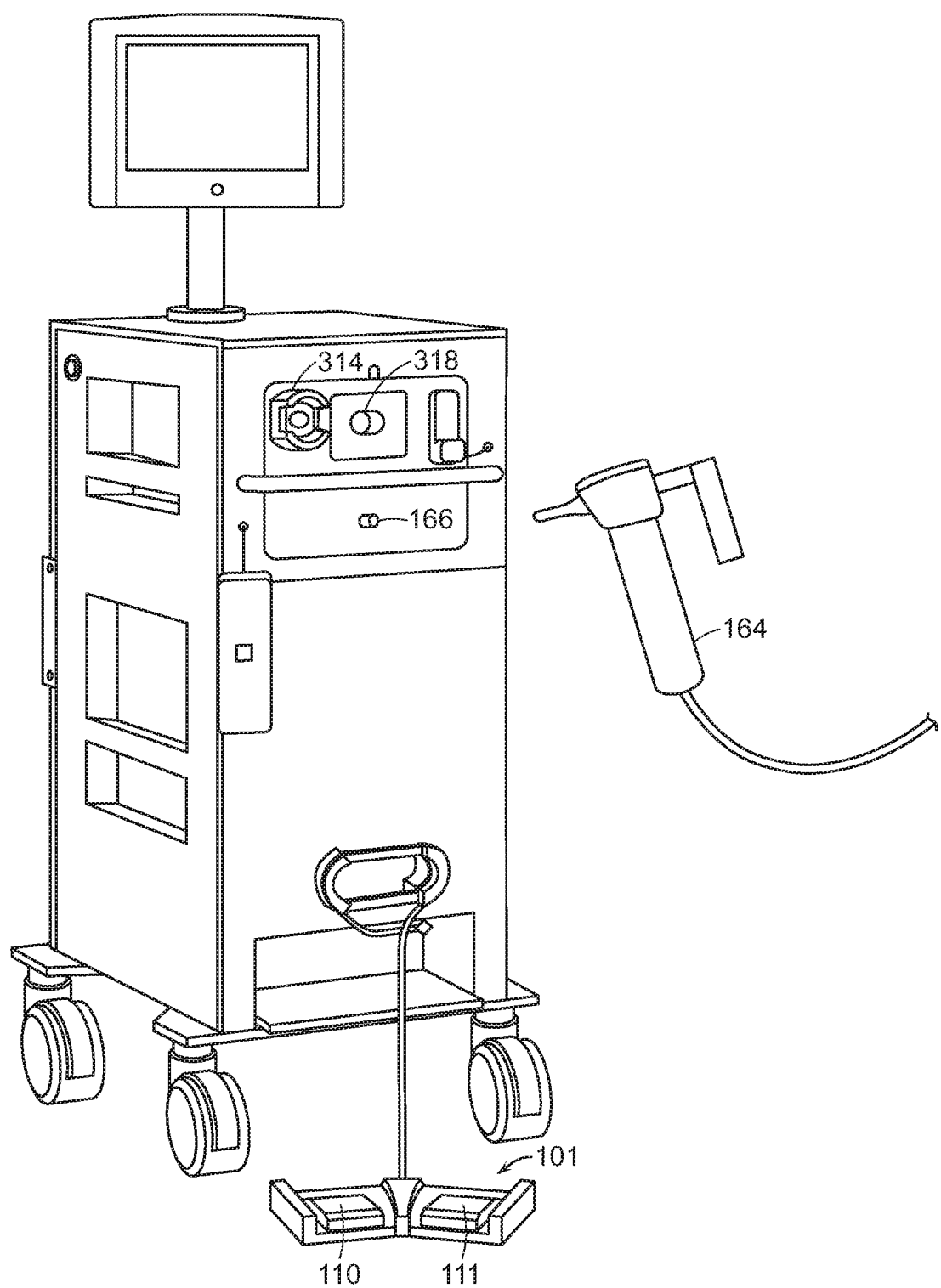
FIG. 2 is a perspective view of another embodiment of a cryosurgery system according to the invention.
Figure 3:
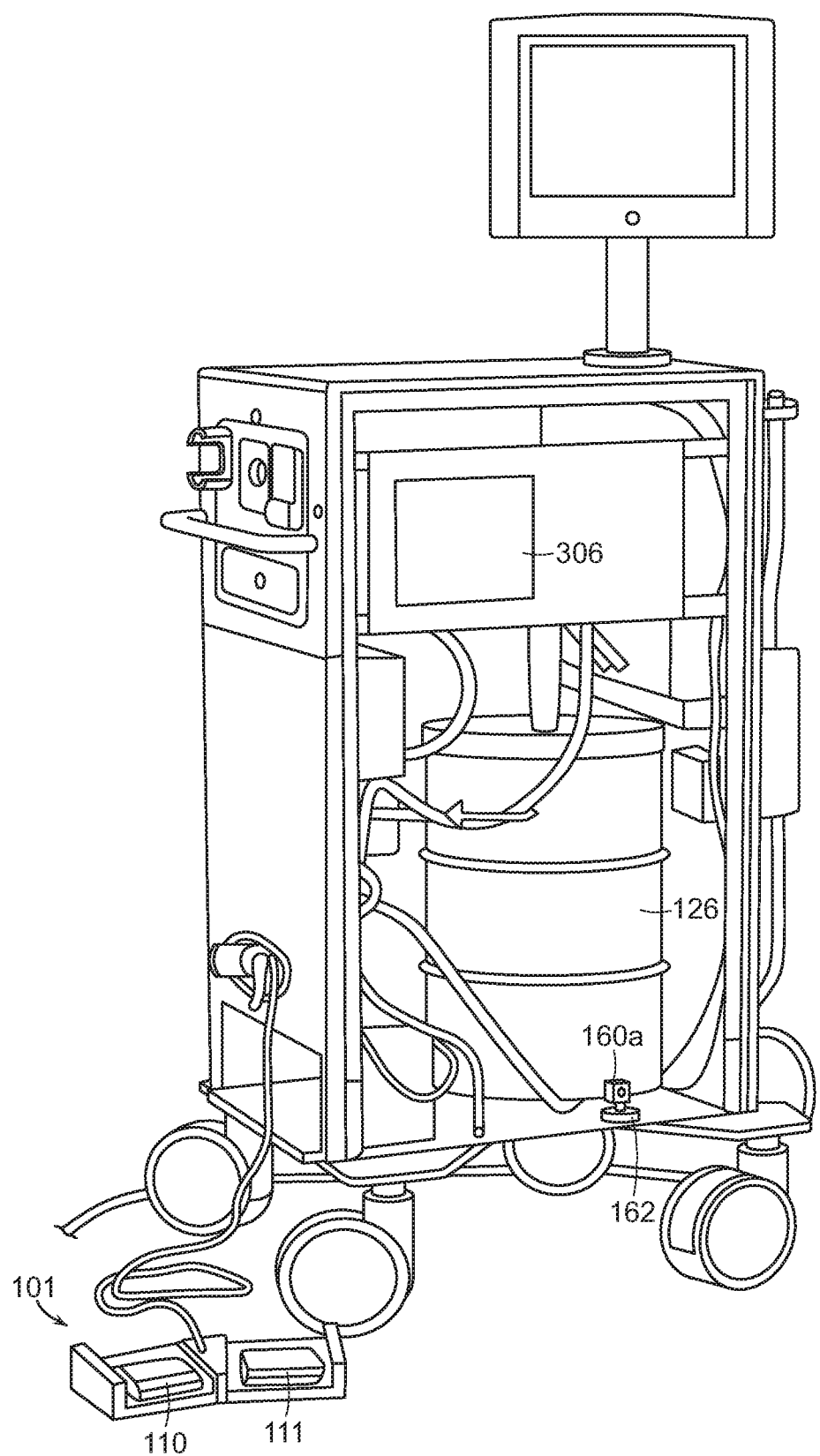
FIG. 3 is a perspective view of the interior of an embodiment of a cryosurgery system according to an embodiment of the invention.

A simplified perspective view of an exemplary cryosurgery system in which embodiments of the present invention may be implemented is illustrated in FIGS. 1-3. Cryosurgery system 100 comprises a pressurized cryogen storage tank 126 to store cryogen under pressure. In the following description, the cryogen stored in tank 126 is liquid nitrogen although cryogen may be other materials as described in detail below. The pressure for the liquefied gas in the tank may range from 5 psi to 50 psi. According to a more preferred embodiment, pressure in the tank during storage is 40 psi or less, and pressure in the tank during operation is 35 psi or less. According to a more preferred embodiment, pressure in the tank during storage is 35 psi or less and pressure during operation is 25 psi or less. According to a most preferred embodiment, pressure during operation at normal nitrogen flow is 20±4 psi.

Nominal tank pressures according to preferred embodiments of the present invention are established to assure that different systems have a standardized energy output, which is, for example, the nominal energy output of a standard system used to successfully deliver treatment in an animal model or in a human patient according to one of the various embodiments of the present invention; Energy output of individual systems is assessed using one or more of a standard catheter and/or a standard airway phantom comprising multiple one or more temperature sensing elements (e.g. one or more thermocouples); temperature changes measured by the phantom are used to calculate the total energy output during the spray, and multiple sprays may be carried out at varying pressures to establish a pressure-energy relationship that is then used to select a pressure value that yields the energy output of the standard system, within a predetermined error (e.g. ±5% of standard energy output).

In an alternate embodiment, the cryogen pressure may be controlled all the way to 45 psi to deliver through smaller lumen catheters and additional feature sets. In such alternate embodiments the pressure in the tank during storage may be 55 psi or less.

Liquid nitrogen (LN2) resides on the bottom of the tank and liquid nitrogen gas/vapor (GN2) occupies the top portion of the tank. Tank level is monitored electronically via a sensor internal to the tank that changes value with the level of the liquid inside the tank. This can be done in a variety of ways, including but not limited to capacitively (an example being a Rotarex C-Stic), resistively, or by measuring differential pressure.

Figure 4A:
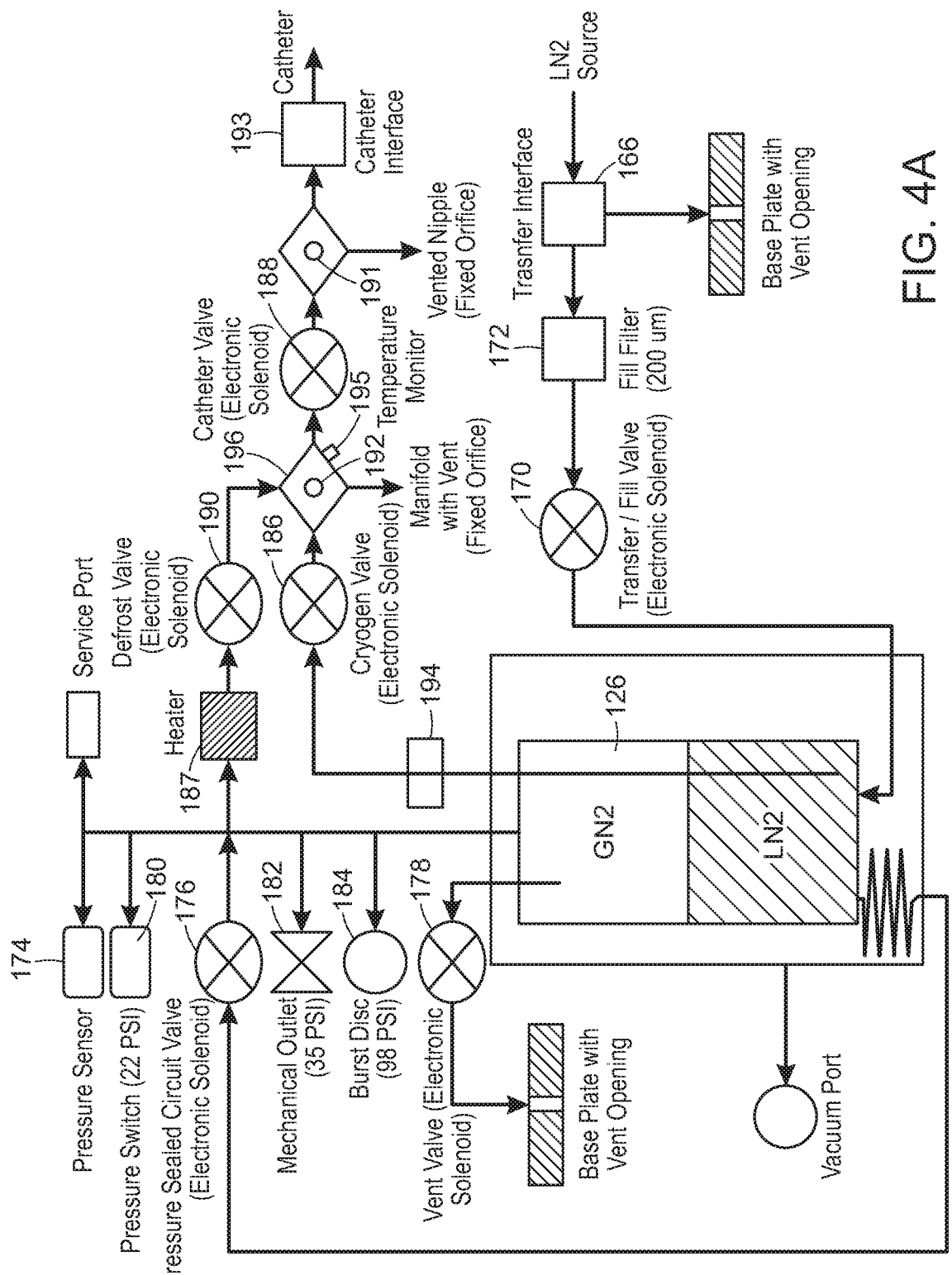
FIG. 4A is a schematic showing a cryogen storage, delivery and pressure control apparatus according to an embodiment of the invention.
Figure 4B:
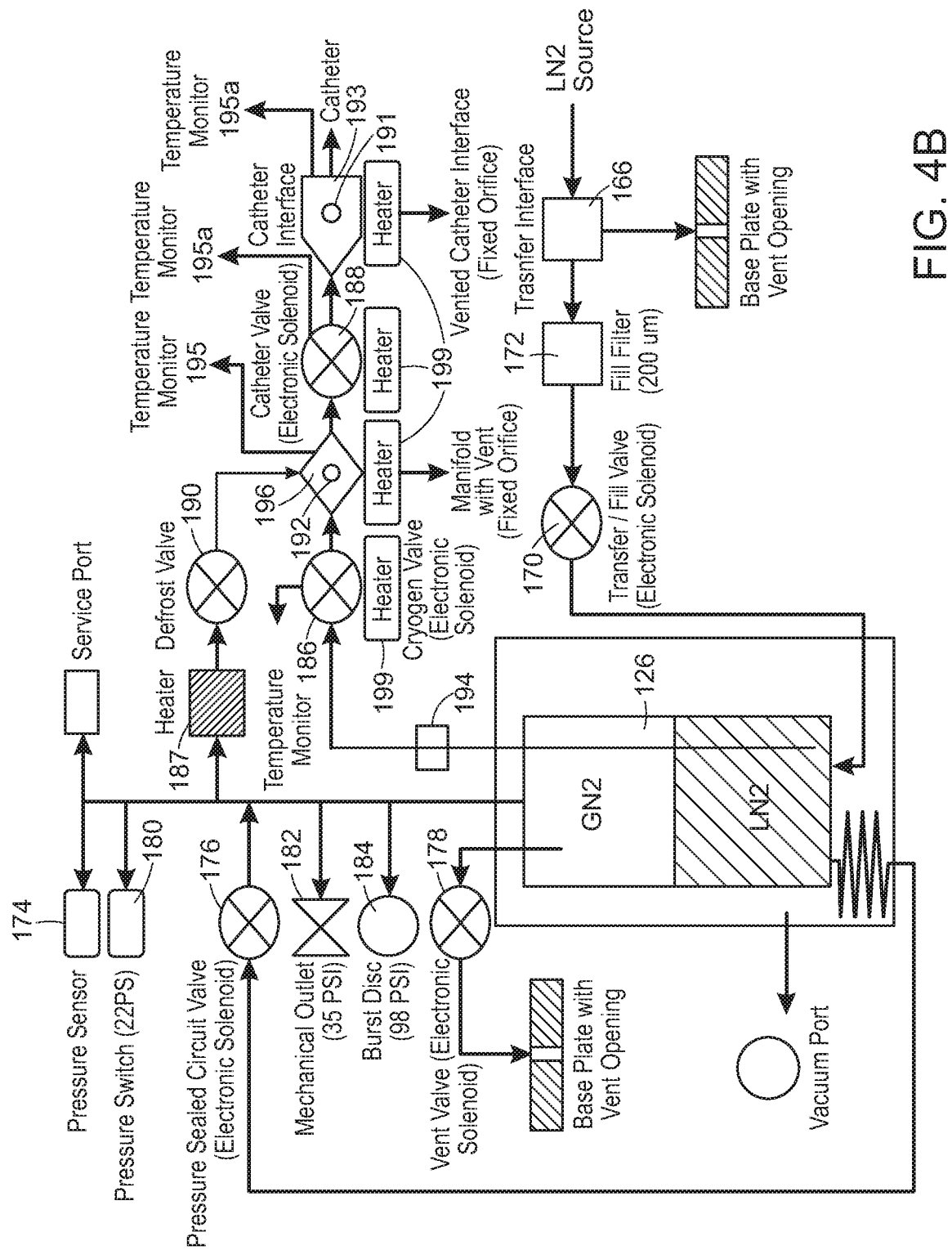
FIG. 4B is a schematic showing a cryogen storage, delivery and pressure control apparatus according to another embodiment of the invention.

Referring to FIGS. 4A and 4B, the present invention utilizes valves and a pressure sensor 174 to continuously monitor and control the pressure of liquid nitrogen in the tank during use. The console monitors the current pressure of the tank via a pressure sensor 174. The software reads the current pressure from the sensor and adjusts the pressure accordingly. If pressure is too low, the software actuates the pressure build circuit valve 176 to increase the pressure to a specified threshold and then turns off. When the pressure is too high, the software turns on the vent valve 178 until the pressure reaches a specified threshold.

In some cases, system charge pressure is actively controlled by a set of three solenoid valves. A cryogenic solenoid valve connected to the head space is used for rough reduction of tank pressure in cases where tank pressure is significantly above the desired set pressure (>5 psi) or during fill operations when tank pressure must be completely relieved. A set of proportional solenoid valves control the pressure vent and pressure build functions. The proportional solenoid valves are driven by a pulse width modulation (PWM) controller which adjusts its duty cycle based on a control voltage, allowing the valve plunger position to open proportional to the control signal. The control signal is driven by a standard proportional integral derivative (PID) control algorithm executable by a central processor of the system. The PID controller collects data from a precision capacitive pressure sensor and adjusts the valve control signal based on the current pressure deviation with respect to the set point, the current rate of change of pressure, and the pressure history. A PID output control signal determines whether venting or building operations occur. This control scheme advantageously implements precise pressure regulation while allowing software changes to the pressure set point. The PID controller is tuned (inputs P, I, and D) to provide quick response with minimal overshoot or undershoot, while avoiding unstable cycling between vent and build operations.

A mechanical relief valve 182 on the console tank ensures that the tank pressure stays in a safe pressure range. Constant pressure monitoring and adjustment, allows the set point on the mechanical relief valve to be set at 35 psi, allowing for a low tank storage pressure. A redundant burst disk 184 provides protection should the mechanical relief valve fail. For optimal safety, both electronic and mechanical pressure valves are present to regulate the pressure, providing triple redundancy in the event of failure. In addition, a redundant pressure switch 180 may provide accurate tank pressure readings and is checked during the self-test. In an alternate embodiment, the mechanical relief valve 182 may be set at 60 psi, but still allowing to remain a low pressure storage tank.

The system of the present invention utilizes a manifold assembly including cryogen valve 186, manifold 196, catheter valve 188, defrost valve 190, fixed orifices 191 and 192, and catheter interface 193 to control liquid nitrogen delivered through the catheter. When the cryogen valve 186 is actuated, liquid nitrogen exits the tank through the lance 194 and proceeds through the cryogen valve 186 to manifold 196 where fixed orifice 192 is present to allow cold expanded gas and liquid cryogen to exit the line and cool down the internal cryogen circuit. During this precool, the catheter valve 188 downstream of the manifold remains closed. A data acquisition board collects data from a thermocouple 195 located on the manifold body. In the precool function, the system software monitors data from the thermocouple 195, and opens the cryogen valve 186 to cool the manifold 196 when its temperature is above the desired set-point. According to a preferred embodiment, fixed orifice 191 is provided on catheter interface 193 to allow venting of cold expanded gas to exit the line while spraying.

Figure 4C:
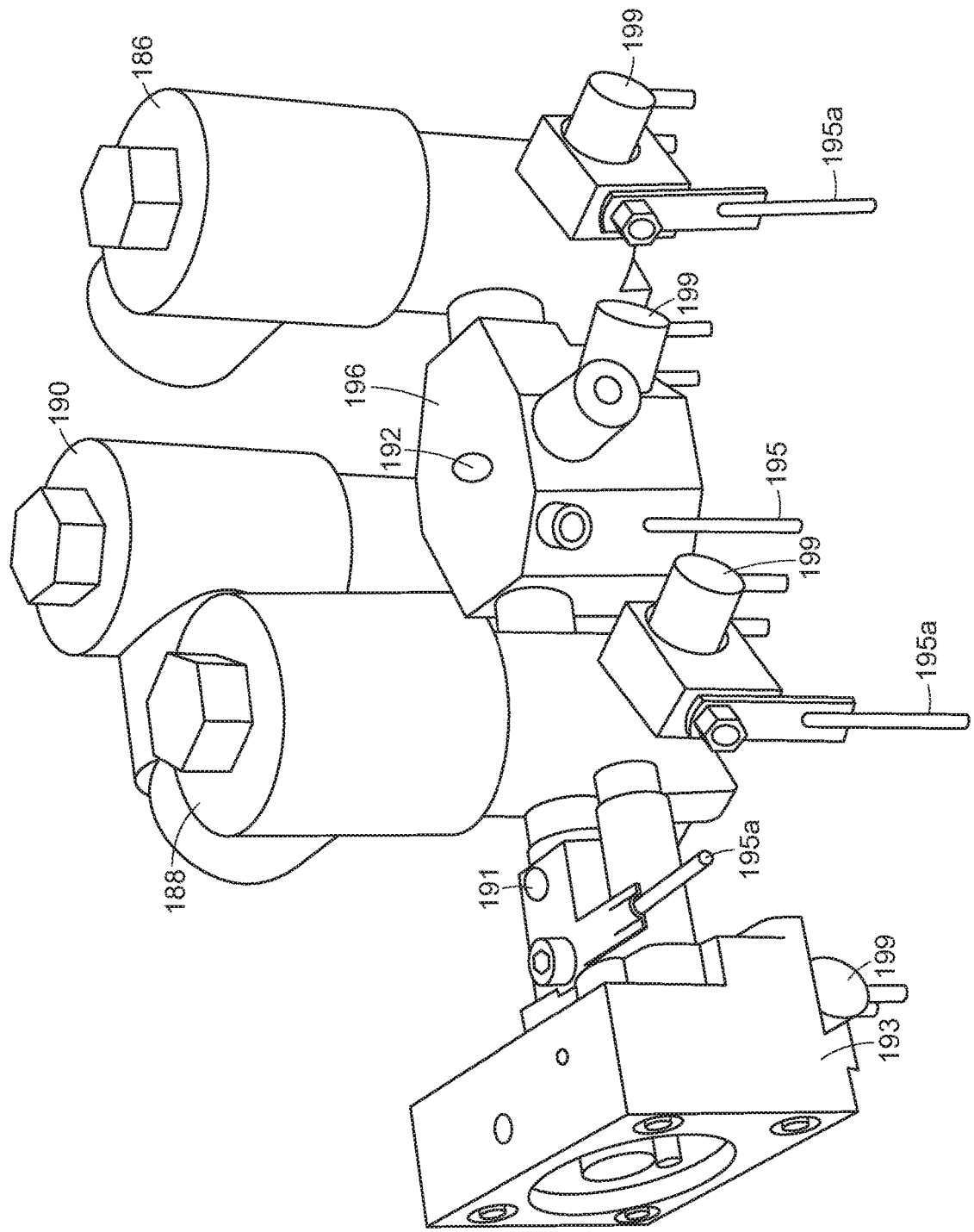
FIG. 4C is a three dimensional perspective representation of a cryogen manifold and valve assembly according to the embodiment shown in FIG. 4B.

According to a preferred embodiment of the invention, represented in FIGS. 4B and 4C, each of cryogen valve 186, manifold 192, catheter valve 188 and catheter interface 193 are provided with a temperature thermocouple or sensor 195a and a heater 199 to maintain the cryogen flow path at a constant selected temperature to prevent overcooling of the system resulting from the continuous flow of cryogen through the valves and manifold assembly. According to various embodiments of the invention, each of the heaters may be controlled to maintain the valves, the manifold and the catheter interface at the same temperature or at different temperatures. According to a preferred embodiment, the system is set so that the temperature(s) of the valves, manifold, and catheter interface is/are controlled to be maintained at a temperature greater than −120° C. during cryospray treatment. According to a most preferred embodiment, the system is set so that the temperature(s) of the valves, manifold, and catheter interface is/are controlled to be maintained at a temperature of +20° C. during cryospray treatment. According to another embodiment, each of the valves, manifold, and catheter interface are controlled and maintained at constant temperatures, but the constant temperatures of each may be different from one or more of the constant temperatures of the others.

A defrost function is useful for thawing the catheter after cryogen spray, before removal from the scope. A defrost circuit directs gaseous nitrogen from the top of the tank through a heater 187 and defrost valve 190 to the catheter 128. When the defrost button on the software screen is pressed, the defrost circuit is activated for a prescribed time (e.g. 30 seconds) but can be stopped earlier at the user's discretion. A low voltage (24 VDC) DC defrost heater delivers 6 W minimum of warming/defrost performance but minimizes variation due to line voltage and limits maximum gas temperature, as compared to the prior art line voltage (120V) AC heater.

The console of the present invention comes with an insulated quick release custom fill hose 164 to fill the tank through the external fill port 166 in a semi-automatic cryogen fill process. A fill port switch on the console actuates only when the fill hose is in the locked position. During the fill process, liquid nitrogen passes through a filter 172 and transfer valve 170 en route to the tank. The software automatically shuts off the electronic transfer valve 170 when the tank is full and vents the hose prior to removing from the console. According to an alternate embodiment, manual filling can take place by mechanically bypassing the electronic transfer and vent valves with manual valves, thus allowing the tank to be filled without the need for computer control.

The catheter is designed to transport liquid nitrogen (or other cryogen) from the console to the patient treatment site. According to one embodiment, the catheter 1 may contain a bayonet 2 and hub 3 for attachment to the console at its proximal end, a laser cut hypotube to minimize kinking and breaking, and a polymer layer disposed over the hypotube, thereby sealing the catheter 1, and an insulation layer 4 to protect the user from cold, a strain relief 4a to help prevent kinking when torqued by users and an atraumatic rounded tip (10) at its distal end to prevent damage to tissue. The hypotube is preferably spiral cut, imparting radial flexibility while maintaining some axial stiffness and pushablility, and the relative flexibility of the hypotube is, in some cases, variable along the length of the catheter 1 through the use of a variable-pitch spiral cut. For instance, the spiral cut may be characterized by a first, relatively large pitch proximally, and a second, smaller pitch more distally, allowing the distal end, and particularly the tip, to bend about a tighter curve than the most proximal portions of the catheter. The strength and flexibility provided by catheters according to these embodiments allows a user (e.g. a physician) to retroflex the catheter during a treatment procedure, if needed.

The polymer layer may be any suitable flexible polymer that is substantially gas impermeable (for example fluorinated ethylene propylene or urethane), and may be disposed over the hypotube in the form of one or more extrusion layers attached by means of heat shrinking, or by means of dip coating, melt coating or spray coating. The catheter package may contain an RFID tag that the user scans prior to use to prevent reuse and track disposable information.

The catheter package may also contain an introducer that provides reinforcement for the catheter and helps prevent kinking during use and when placing the catheter into the scope. An alternative construction locates the RFID tag on the connector area adjacent to the bayonet, such that the RFID tag is scanned by the system when the catheter is connected to the system.

According to a preferred embodiment, the delivery catheter may be constructed out of hypotubes of different internal diameters mated to each other to make a proximal shaft and a distal shaft, with the distal shaft containing the smaller ID. The proximal and distal shafts may be joined at a connector, which connector can be covered by a molded handle to permit a user to make fine adjustments to the catheter 1. The proximal shaft may contain a bayonet and hub for attachment to the console at its proximal end. The distal shaft preferably has a reduced ID to be able to fit through the working channels of a bronchoscope. The distal tip of the catheter contains the radial spray pattern holes which make up the nozzles configured to deliver the cryogen spray onto the target tissue. The end of the catheter may be configured to have a rounded tip, preferably made of a welded stainless steel sphere. This rounded tip may help reduce trauma to the tissue during catheter insertion or manipulation into the body cavities. A thermocouple may be located along the catheter shaft, preferably at or near the distal tip of the catheter, to provide temperature feedback to the control console, for example to better determine the precise moment that cryospray exits the tip of the catheter. The hypotubes are all laminated with a polymeric heatshrink which seals the laser cut pattern from the liquid intended to flow inside the catheter. Additionally, both hypotubes have variable laser cut patterns which provide rigidity where needed and much flexibility where needed. This is accomplished by varying the separation of the spiral or repeated cut pattern, as well as varying the shape of the pattern itself.

According to an alternative embodiment, the delivery catheter may be constructed of one or more layers of flexible polyimide, surrounded by a stainless steel braid, which is in turn coated with an outer layer of Pebax. It was discovered that that extrusion of Pebax block copolymer over the stainless steel braid allows the Pebax to wick through the pitch of the steel braid, helping to prevent kinking, breaking, or delamination during retroflex of the catheter. The Pebax also provides a desirable balance between hardness—important for smooth sliding of the catheter and general toughness, and softness, which is important for some degree of tackiness which allows the user to feel the movement of the catheter in the scope. The pitch of the stainless steel braid is configured to be fine enough to afford the required strength, but still allow the Pebax to wick through. The distal end of the catheter is provided with an atraumatic tip comprised only of Pebax, in the shape of a bullnose. This novel construction allows for retroflex of the catheter without kinking, breaking, or delamination of the catheter. For the purposes of this invention, retroflex is used to refer to the ability of a catheter to bend or turn approximately 210° about a radius of curvature of 0.375 inch or greater.

FIG. 5 shows the preferred embodiment catheter construction of the cryospray catheter 1 according to the invention. It includes a bayonet connection 2, catheter connection housing 3, insulation 4, laser cut hypotube with FEP or Pebax heatshrink wrap 5, nozzle connection of diminishing inner diameter 6, second smaller ID laser cut hypotube 7 with FEP or Pebax heatshrink wrap, radial spray pattern holes 8, spray pattern indicator marking bands 9 (two are shown, but three or more may be provided, for example, to account for spraying in smaller distal segments), and rounded tip 10.

By adding very thin layers of metal to the catheter shaft or increasing the heat transfer coefficient in the shaft by using a hypotube or adding a braided metal for example, the catheter may be constructed to provide optimal cryo delivery to the tip of the device in a very short cycle time.

FIG. 6 shows a typical hypotube 19 used for the construction of the proximal end of the catheter shaft 5. It typically has a length of 45 inches but can vary from 24 to 96 inches in length. The internal diameter of the tube 19 is usually 0.104 inches but can vary between 0.045 to 0.150 inches. In the preferred embodiment, the hypotube 19 may be laser cut as a spiral, but other variable cuts can be present. The cuts provide flexibility to the metal tube.

FIG. 7 shows a transition 25 of a large diameter hypotube shaft 19 to a small diameter laser cut hypotube shaft 8. The transition is so that a smaller diameter can be inserted into the working channel of a scope. In addition, the transition from large diameter to small diameter acts as a mixing point for the dual phase flow gas and liquid to interact along the catheter path and allow for the gas to once again attain the velocity of the liquid as they travel down the pipe. This transition is referred to as a "nozzling" transition. This transition can occur between two hypotubes, two polymeric shafts or between a coil and hypotube or coil and polymeric shaft.

Figure 8:
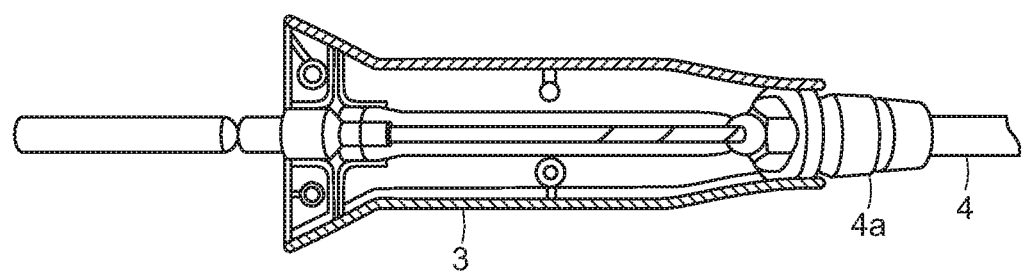
FIG. 8 shows the insulator and connector housing area with the bayonet, according to one embodiment of the invention.

FIG. 8 shows the insulator 4 and the connector housing 3 added to the catheter assembly 1.

Figure 9:
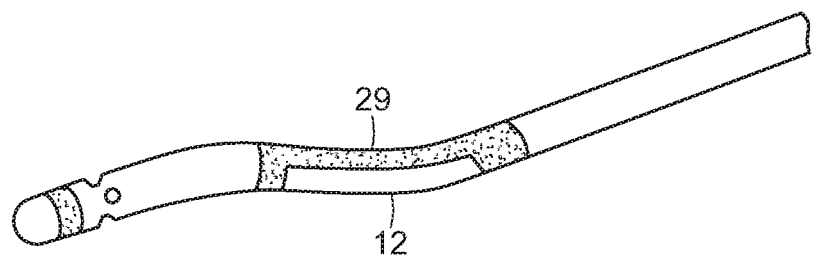
FIG. 9 shows an embodiment of the invention including an S-curve centering feature on the radial spray catheter containing an axial marker line that aids in visual positioning of such S-curve with respect to centering of such offset to the scope centerline.

FIG. 9 is an isometric view of an alternate embodiment catheter with an S-curve centering feature built into its distal tip shape. It shows the bend 12 and the alignment line 29 that is the feature used to visually align the catheter with respect to the scope working channel offset.

Figure 10:
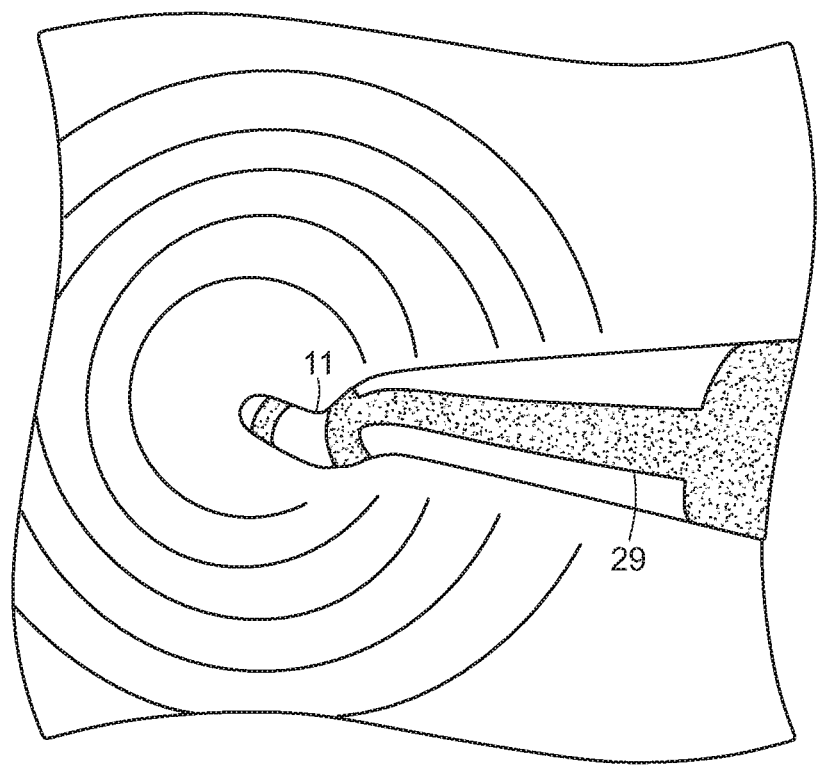
FIG. 10 shows an S-curve centering feature and axial line as viewed by the scope optics during use.

FIG. 10 shows the S-curve 12 of an alternate embodiment as seen through the scope 20 visualization system. The method of use is to target the area to be treated by locating the catheter section 11 between the marking bands, then rotating the catheter axially until the axial line 29 is visible and horizontal in the line of vision. At this point the catheter tip is relatively centered with the scope 20 centerline. This axial line is typically created via a pad printed or laser marking process.

Figure 16A:
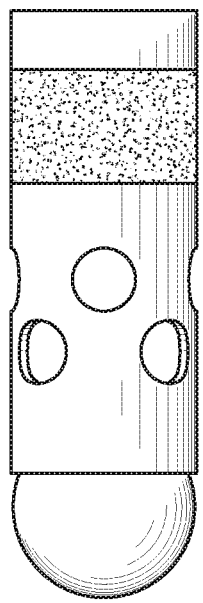
FIGS. 16A-16F show various radial spray pattern embodiments that can be located at the distal tip of the catheter.
Figure 16B:
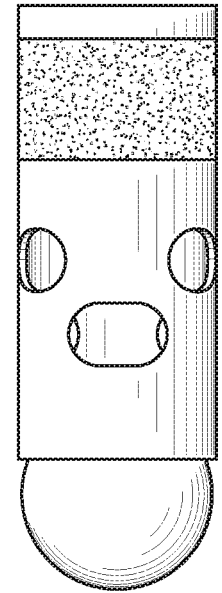
Figure 16C:
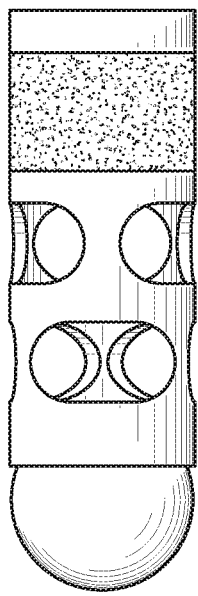
Figure 16D:
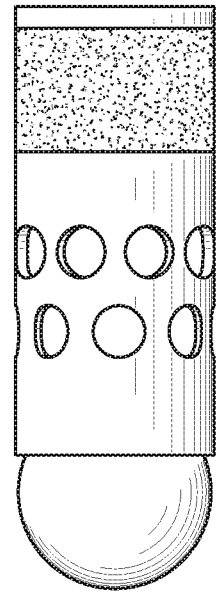
Figure 16E:
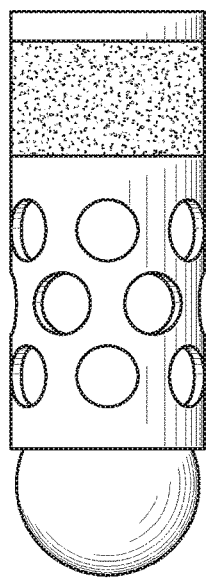
Figure 16F:
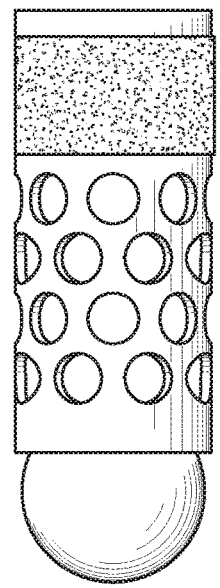
Figure 16G:
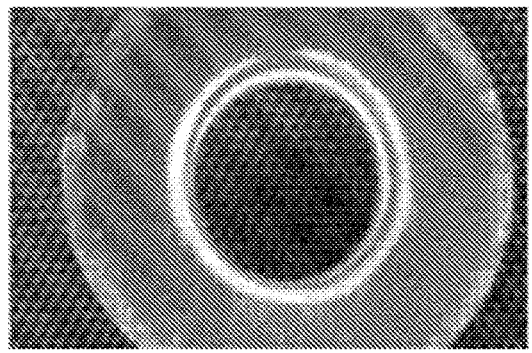
Figure 16H:
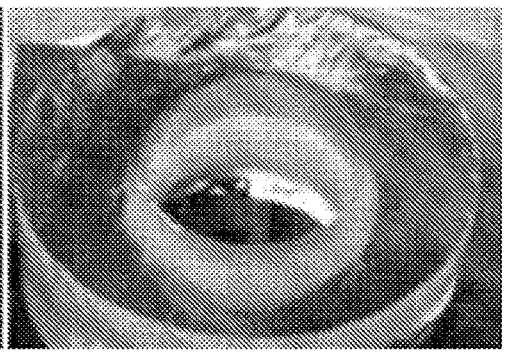
Figure 16I:
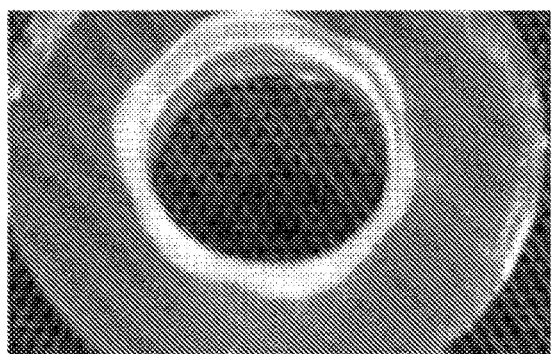
FIGS. 16I-J illustrate cryospray delivery patterns that result from the radial spray design illustrated in FIG. 16A.
Figure 16J:
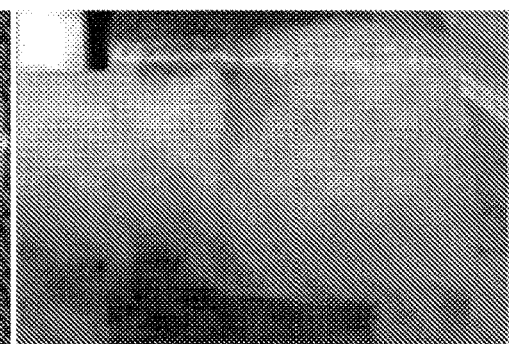

The preferred radial spray pattern of the catheter distal tip is 2 rows of holes equally dispersed around the circumference of the shaft, each row containing 8 holes of 0.016" each. The first and second row are separated along the length of the shaft by a distance of 0.025" measured from the centerline of the first row to the centerline of the second row, and the holes are arranged at 22.5° angles from each other as seen on FIG. 16D. As is shown in FIG. 16G-H, this radial spray design results in a pattern of cryospray delivery that is radially and axially uniform about the circumference of the airway, and that, when used to deliver "metered" cryospray amounts (i.e. cryospray amounts determined by an automated system of the present invention, delivered utilizing delivery protocol generated and executed by an automated system of the present invention) permits reliable, repeatable ablation of mucosa without the risk of damage to deeper tissues including airway cartilage; generally, ablation achieved using a radial spray design according to FIG. 16D in conjunction with an automated cryospray system of the present invention results in an annular ablation to a depth of between 0.1 and 0.5 mm that is characterized by a uniform radial and axial margin; the depth of ablation can be increased in some cases while preserving its uniformity (not shown). Importantly, the axial extent of cryospray delivery is generally coextensive with the length of the spray pattern of FIG. 16D, and is not axially offset as is observed in other systems. Thus, a user of a system incorporating the tip design of FIG. 16D can be reasonably assured that, when cryospray is delivered to the airway, it is delivered in the region in which the tip of the catheter is actually disposed. The inventors have found that other designs, such as the design of FIG. 16A, generally result in more variable and, frequently, deeper patterns of ablation that are not as advantageous for use in automated systems. For instance, FIG. 16I-J shows a cryospray delivery pattern obtained using the tip design of FIG. 16A that exhibits "scalloping" both in depth and axial extent; such scalloping, while appropriate or even useful for certain applications, is not optimal for mucosal ablation applications to treat, for instance, chronic bronchitis, as it raises the simultaneous risks of overtreatment of certain regions (potentially causing damage to airway cartilage) and undertreatment of others (potentially sparing portions of the mucosa contributing to the disease process).

The holes are located around the circumference of a short stiff section of the hypotube without laser cuts, with such section being as small as 0.050" in diameter to allow the hypotube to navigate through a retroflexed bronchoscope or any other areas of tortuosity Alternative patterns of alternate embodiments are shown on FIGS. 16B-16F. The embodiment shown in FIG. 16A has two rows of four round holes of 0.023" in diameter. The embodiment shown in FIGS. 16B and 16C have two rows of three oblong holes that are 2 to 4 times in length as compared to the diameter of the ends. The embodiment shown in FIG. 16E has three rows of six round holes, each having a diameter of 0.022". The embodiment shown in FIG. 16F has four rows of eight holes, each having a diameter of 0.016".

Figure 11A:
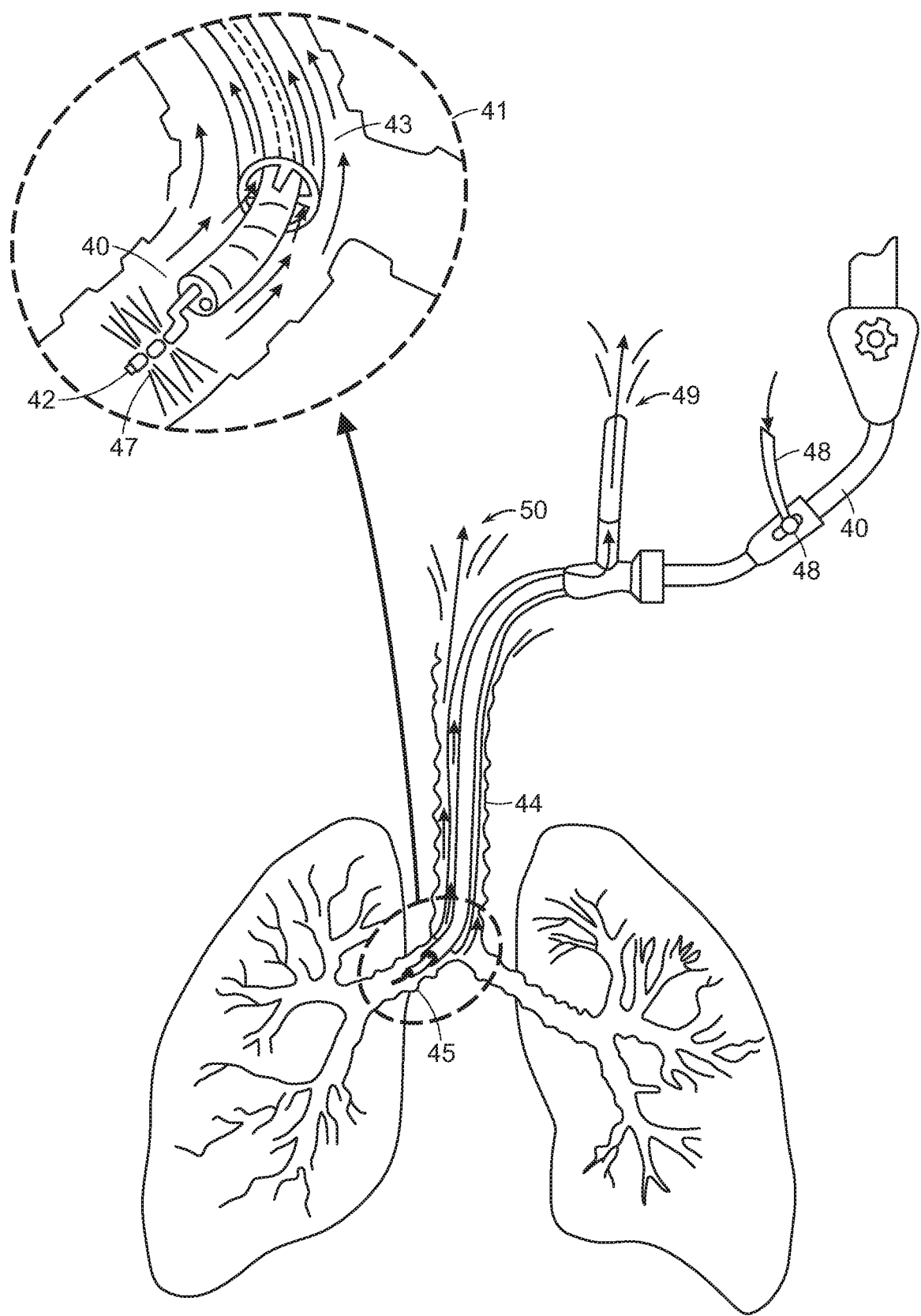
FIG. 11A is a perspective view, including a blow-up view, of a portion of a cryosurgery system 41 having a cryogen delivery apparatus 42, including bronchoscope 40, gas egress tube 43, and an S-shaped catheter tip 42 exiting the working channel of the bronchoscope.
Figure 11B:
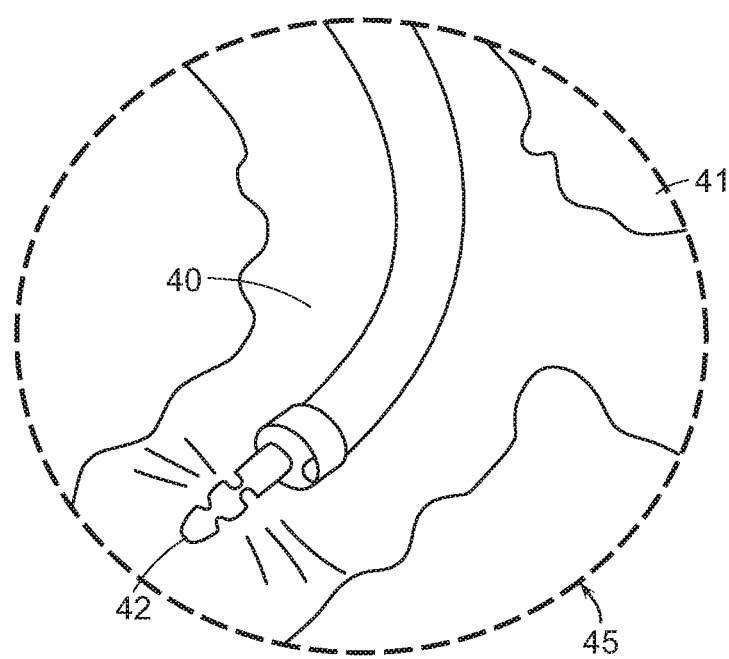
FIG. 11B shows a blow-up of an alternate embodiment with a straight catheter tip and no gas egress tube.

Referring to FIG. 11A, bronchoscope 40 may be positioned in the trachea 44, or bronchi—such as the principle bronchi 45 of patient. The catheter 48 is placed in the working channel lumen 46 of the scope 40 and exits the working channel at the distal tip of the scope. Cryogen delivery apparatus 42 comprises a radial spray cryogen delivery catheter at distal end 42, and one or more holes 47. After insertion of the cryogen delivery apparatus into the patient, cryogen is provided to cryogen delivery catheter 48 from a cryogen source. A gas egress tube 43 that surrounds the scope may be utilized to provide additional means to evacuate the treatment area of the cryogenic gas out of the patient 49. Passive lumen egress 50 is also present via the management of the airway to ensure proper venting during the procedure. FIG. 11B shows a blow-up of an alternate embodiment, in which a straight tipped catheter is used and without a gas egress tube.

Figure 18:
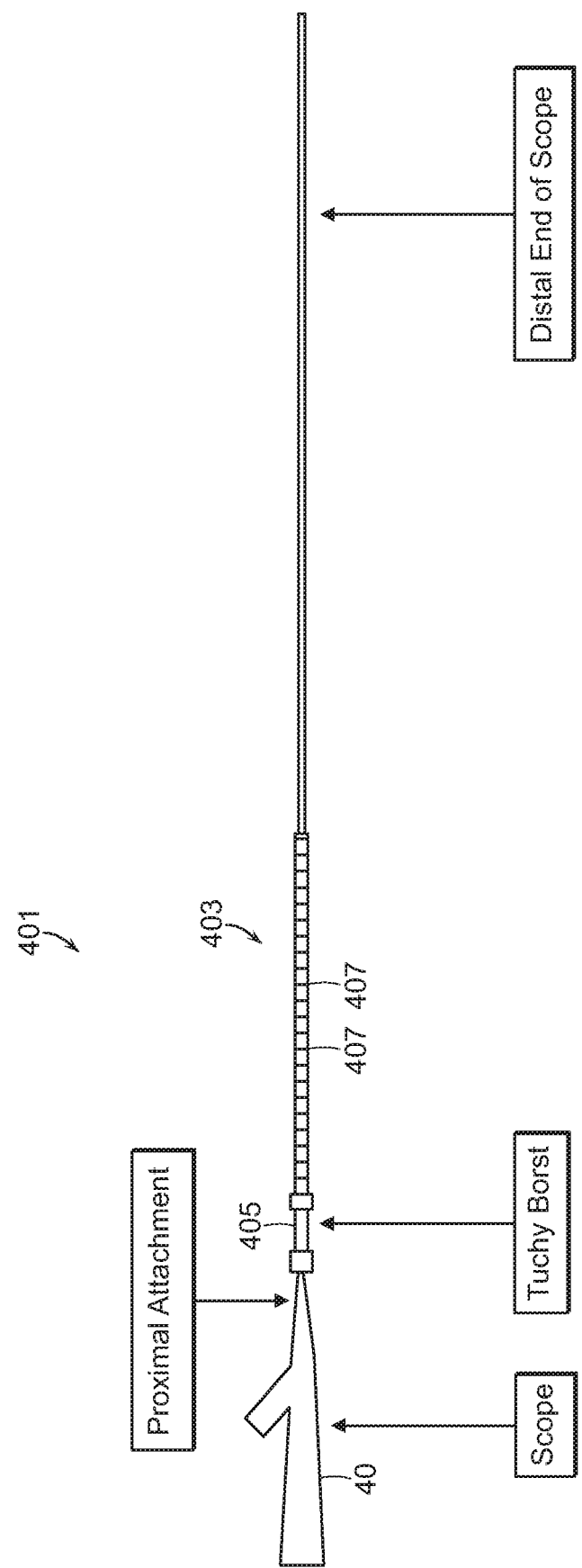
FIG. 18 shows a dose spacing sheath according to an embodiment of the invention.

Referring to FIG. 18, a dose spacing sheath is shown which is configured to be placed over the outer surface of a bronchoscope along a portion of its length during cryospray treatment of an airway or other bronchoscopic procedure. A dose spacing sheath 401 may be made of an elongated tube 403 having a lumen configured to receive a bronchoscope 40, a securing device 405, for example a Tuohy-Borst, at one end of said tube configured to secure a proximal end of said sheath to a proximal end of the bronchoscope, and a plurality of markings 407 along a portion of the external surface of the tube configured to denote a distance that said scope is moved relative to a fixed position of a patient, a patient feature, or other fixed reference point. Said markings may be circumferential marker bands outside the working channel of the scope and may optionally be associated with printed numbers. When aligned with a venting tube (e.g. rigid bronchoscope or endotracheal tube), the markings provide an extracorporeal proximal reference mark prior to dosing. In subsequent doses, the reference markers assist the physician when the scope is moved proximally to the next dosing site so as not to overlap doses.

FIGS. 13-14 show a variety of screens displayed by the system during an exemplary procedure according to an embodiment of the present invention. A home screen (not shown, but similar to that shown in FIG. 13A, is displayed during system power-up and self-test. The self-test can be cancelled so the user can proceed directly to filling the console. Once the self-test completes, the system proceeds to the next screen.

Figure 12:
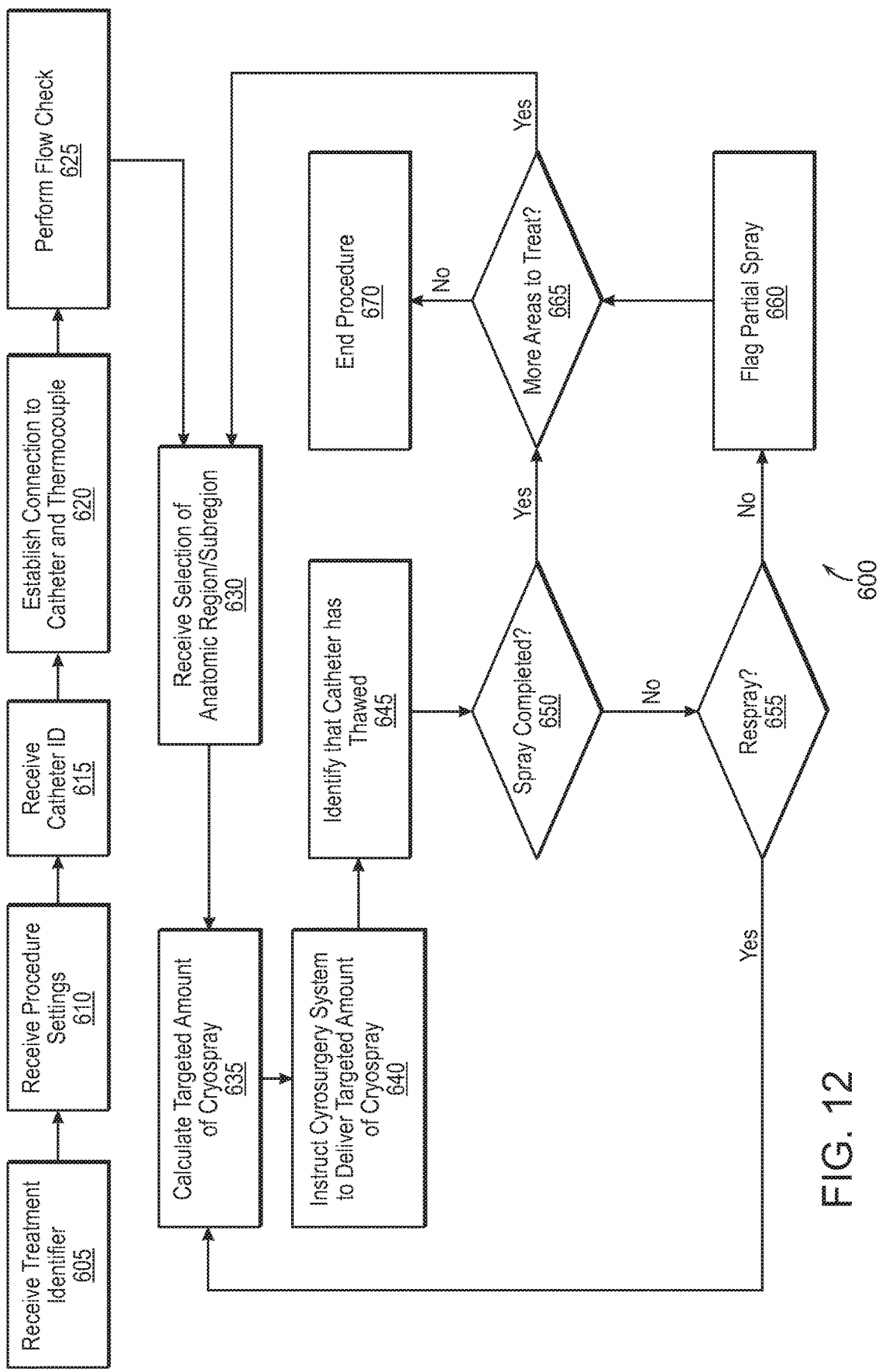
FIG. 12 is a flowchart depicting a method in accordance with an exemplary embodiment.

FIG. 12 depicts an exemplary method 600 for setting up the cryosurgery system 100 and performing an ablation procedure. The following description of the steps illustrated in FIG. 12 is supplemented with references to exemplary interfaces as shown in FIGS. 13A through 14P.

It is noted that the steps depicted in FIG. 12 are intended to be exemplary only. One of ordinary skill in the art will recognize that exemplary embodiments may include more, fewer, or different steps. Moreover, unless otherwise noted the ordering of the steps may be rearranged.

Figure 13A:
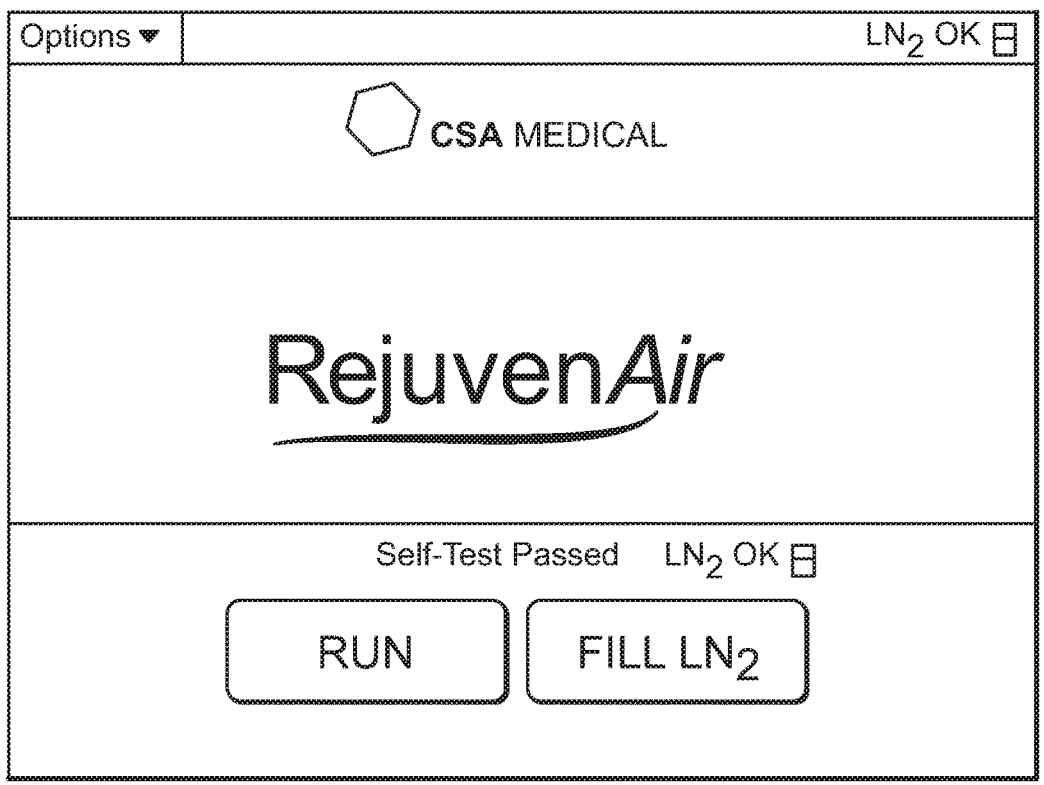

As an initial matter, a computing device associated with the cryosurgery system 100 may be initialized and may initialize the cryosurgery system 100. For example, as shown in FIG. 13A, the initialization process may involve performing self-checks, configuring the system to receive a new fill of cryogen, establishing communication between various components of the cryosurgery system 100, and retrieving any relevant patient records, among other actions.

Figure 13B:
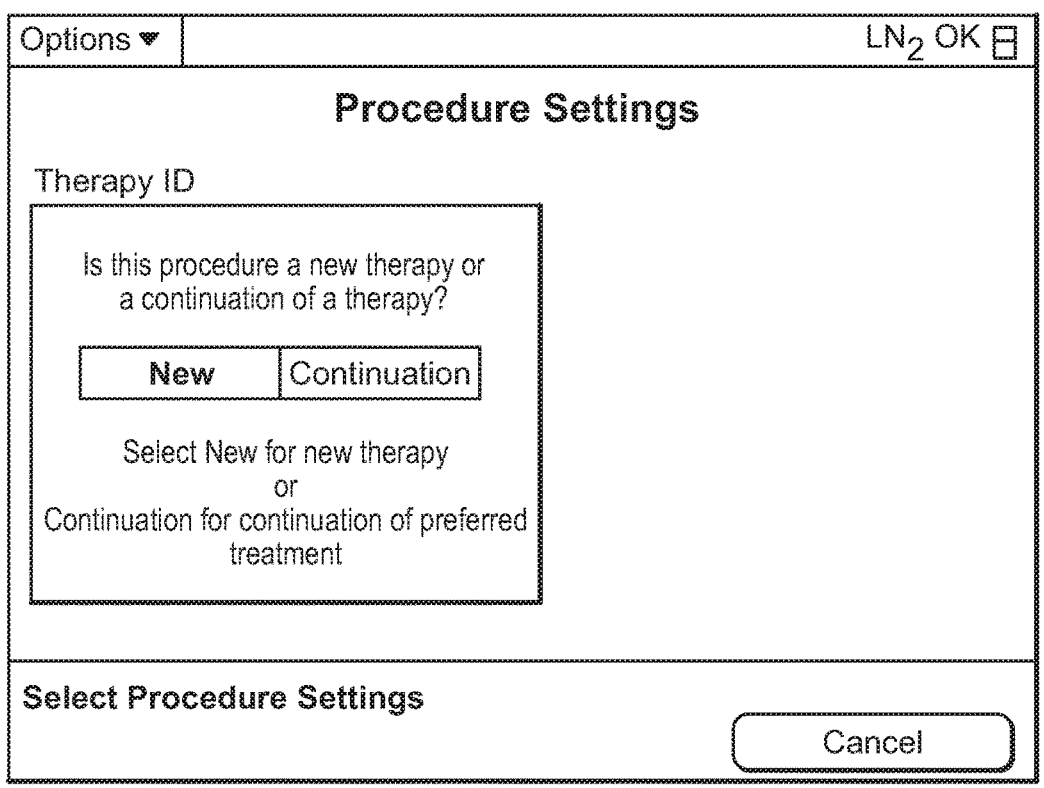

Once the system has been initialized, at step 605 the computing device may receive a treatment identifier. For example, as shown in FIG. 13B, an interface may be presented querying a user as to whether the procedure is a new therapy or a continuation of a previous treatment. If the procedure is a continuation of a previous treatment, then the user may be prompted to provide an identification of the previous treatment, and relevant treatment records may be retrieved from the computing device's storage. Details of the continuation therapy may be appended to the record as the therapy is carried out.

Figure 13C:
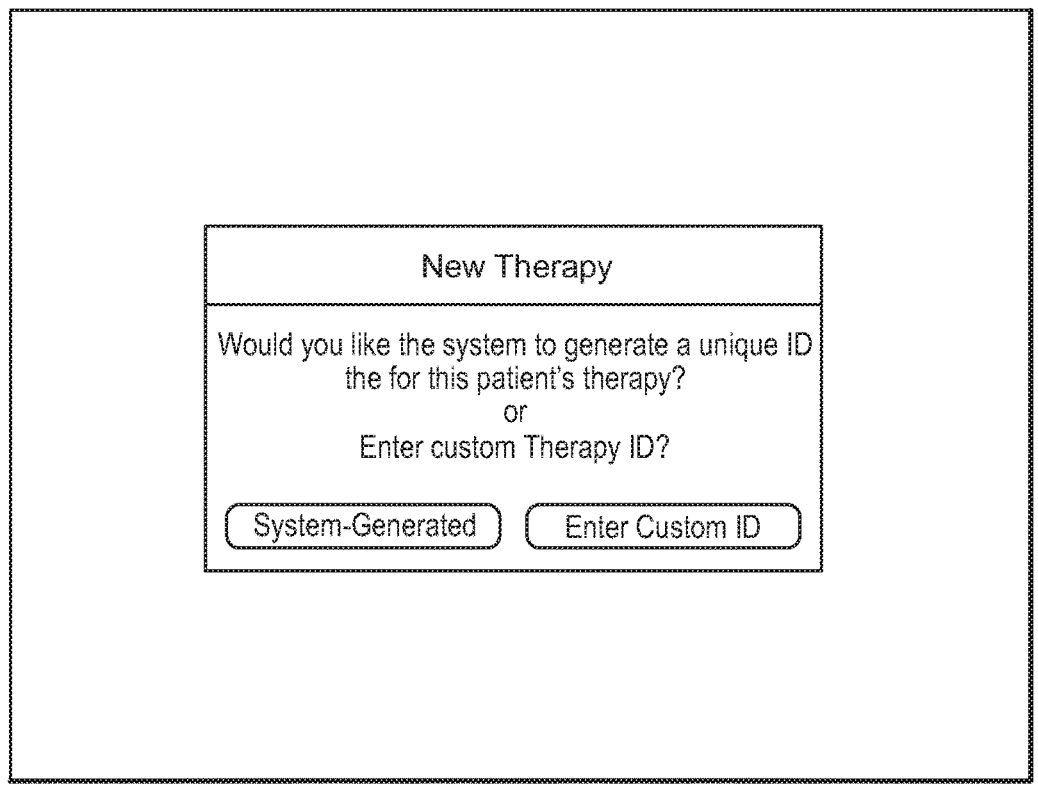
Figure 13D:
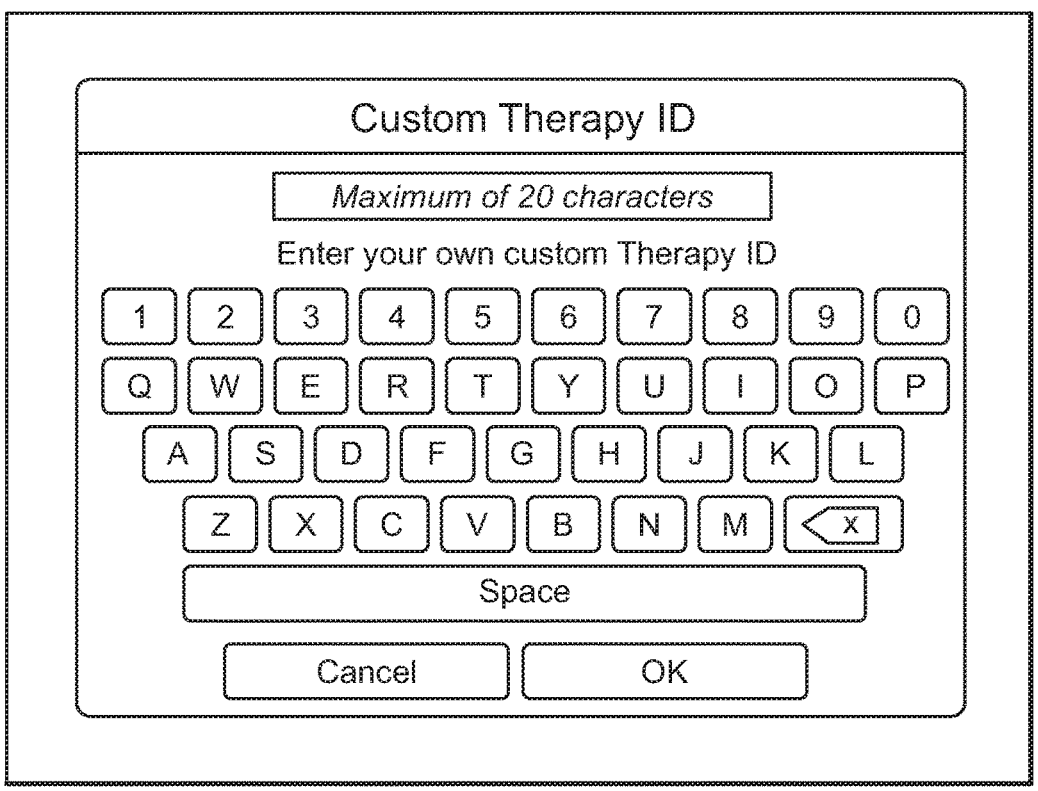

If, on the other hand, the therapy is a new therapy, the computing device may present an interface allowing a user to either enter a new therapy identifier, or have the system generate a new therapy identifier automatically (see FIG. 13C). The new therapy identifier may be associated with a patient record in the computing device's storage. If the computing system receives a selection indicating that the system should generate an identifier, then the system may create a unique identifier based on any appropriate creation scheme (e.g., by selecting a sequential identifier, or generating a random identifier and checking to ensure that the identifier is not already in use). If the computing device receives a selection indicating that the user will enter a custom identifier, then the computing device may present a new interface (e.g., as shown in FIG. 13D) allowing the user to enter a custom therapy identifier. Optionally, the computing device may verify that the user-entered custom therapy identifier is not already in use.

Processing may then proceed to step 610, where the computing device may receive procedure settings. The procedure settings represent patient information that is used to determine the amount of cryospray to deliver to target areas of the patient's lungs. According to exemplary embodiments, the cryosurgery system 100 and associated computing device are configured to determine a targeted amount of cryospray on the basis of only limited information. For example, as shown in FIG. 13E, the procedure settings may consist of the patient's gender and lung terminology which defines the airway locations to be selected later. In combination with a target area of the lung to be treated, these procedure settings may be sufficient to determine a targeted amount of cryospray to be applied. Optionally, the computing device may present an interface requesting that the procedure settings be confirmed by a physician, as shown in FIG. 13F.

At step 615, the computing device may receive a catheter identifier that corresponds to a type of catheter and/or to a specific catheter. For example, each catheter may be provided with a form of identification, such as an RFID tag or a bar code, and the tag or code may be scanned by a suitable scanning device in communication with the computing device. FIG. 13G shows an exemplary interface for receiving a scan of an RFID tag associated with a catheter.

At step 620, the computing device may determine that the catheter or thermocouple are plugged into the cryosurgery system 100, and/or may establish a connection to the catheter and thermocouple. The computing device may, for example, identify one or more data ports associated with the catheter or thermocouple that enable one-way or two-way communication between the catheter/thermocouple and the computing device. The computing device may display a prompt requesting that the catheter and thermocouple be connected to the ports, as shown in FIGS. 13H-13I. Upon detecting the presence of the catheter and thermocouple, and upon establishing communication with the catheter and thermocouple, the computing device may update the display to indicate that the catheter and thermocouple have been successfully connected (see, e.g., FIG. 13J).

Figure 13K:
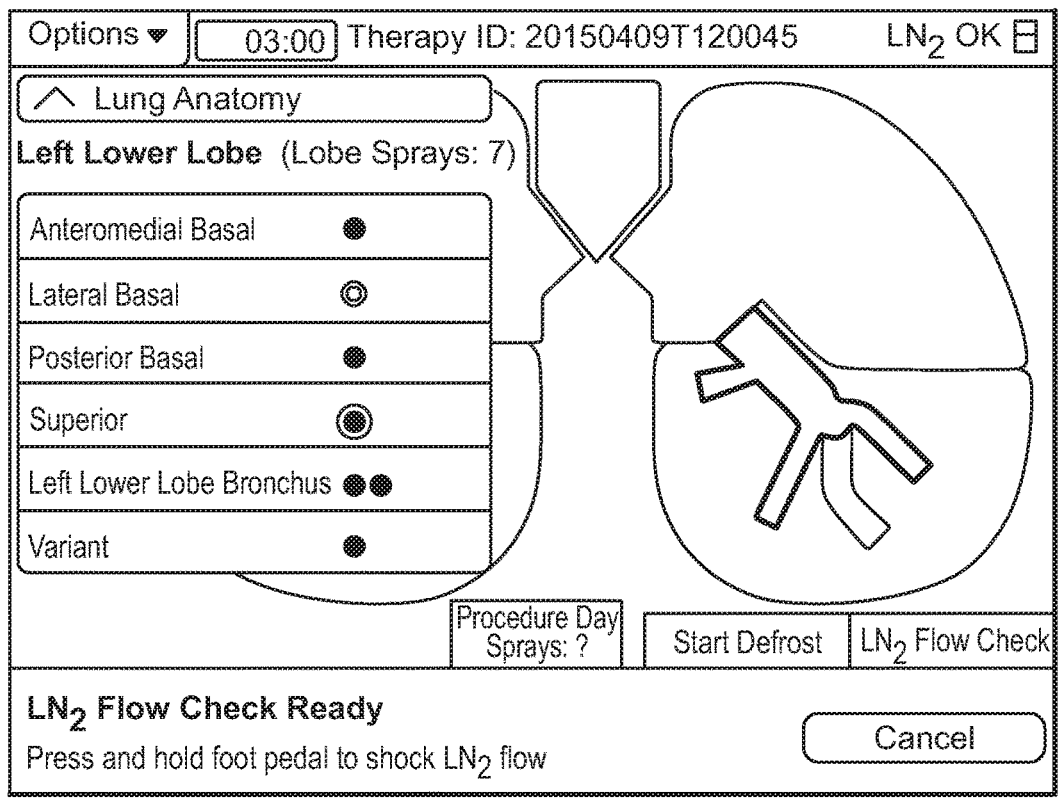
Figure 13L:
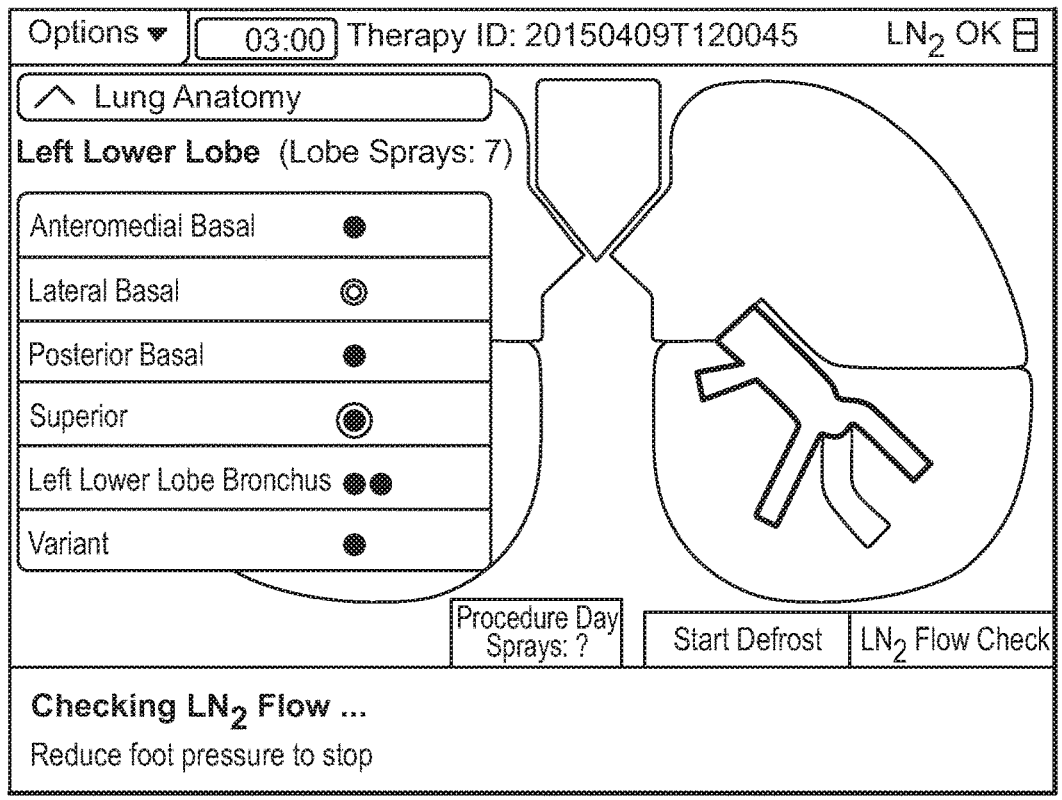

At step 625, the computing device may perform a cryospray flow check. The computing device may automatically initiate a flow of cryospray by sending a command to the cryosurgery system 100, or may prompt a user to manually activate the cryospray (as shown in FIG. 13K). The computing device may prevent the cryospray from being applied, manually or automatically, if certain safety parameters are not met. For example, the computing device may read the temperature from the thermocouple associated with the catheter prior to performing the cryospray flow check. If the thermocouple reports a temperature reading substantially corresponding to a body temperature (e.g., about 37° C.), then the computing device may determine that the catheter has already been deployed in the patient's body. Because the flow check is designed to occur outside of the patient's body, the computing device may, in this case, prevent the cryospray from being applied.

The computing device may evaluate the output of the cryosurgery system 100 (FIG. 13L) and update the interface with the results of the flow check. If the flow is determined to be abnormal (e.g., a flow rate outside of a predetermined range is detected), then the interface may be updated to require that the cryosurgery system undergo maintenance before continuing. If the flow is determined to be normal, then processing may continue to step 630.

At step 630, the computing device may receive a selection of an anatomic region and/or subregion for which an ablation procedure will be performed. The computing device may provide a prompt for allowing a user to enter an identification of a region/subregion to be treated. The prompt may be textual or, as shown in FIGS. 14A-14E, may be graphical.

At step 635, the computing device may calculate a targeted amount of cryospray. The calculation may be performed on the basis of the procedure settings received at step 610 and the region/subregion identified at step 630. For example, the patient's gender and lung terminology, as well as the target region/subregion, may be provided as inputs to an algorithm or algorithms that relate these values to an amount of cryospray necessary to ablate the tissue in the target region/subregion without damaging surrounding tissue. Once the targeted amount of cryospray is determined, processing may proceed to step 640.

At step 640, the computing system may instruct the cryosurgery system 100 to deliver the targeted amount of cryospray as calculated in step 635. For example, the computing system may automatically initiate the delivery of cryospray, or may prompt a user to manually initiate the delivery of cryospray, as shown in FIG. 14F. The computing system may receive a signal indicating that the application of cryospray has commenced.

Once the application of cryospray has commenced, the computing system may monitor the delivery of cryospray. The computing system may measure the amount of cryospray that has been delivered. This may be accomplished, for example, by calculating the amount of delivered cryospray based on the amount of time that has elapsed since the application of the cryospray commenced and the flow rate as determined at step 625, or based on the temperature as measured by the thermocouple. In some embodiments, multiple thermocouples may be strategically located at various locations on the catheter, and the measurements of the thermocouples may be related to parameters that allow the measurements to serve as a proxy for spray output. Once the amount of cryospray that has been delivered matches the targeted amount of cryospray, the computing device may automatically terminate the delivery of cryospray, for example by sending a termination command to the cryosurgery system 100. Moreover, the application of the spray may be stopped when the temperature as measured by the thermocouple indicates that the desired amount of spray has been applied.

During the cryospray delivery procedure, the computing device may measure the temperature of the catheter, as related by the thermocouple affixed to the exterior of the catheter some distance from the tip. The computing device may stop the spray (e.g., by sending the above-described termination command) prior to the delivery of the targeted amount of cryospray under certain conditions. For example, the application of cryospray may be terminated if (a) the temperature drops below a safety threshold, (b) the slope of a temperature curve that the device generates in real time varies (either too high or too low) from a threshold safety range, or (c) if the duration of spray extends beyond a threshold time.

At step 645, the computing device may identify that the catheter has thawed. Before performing additional steps (such as re-applying cryospray or moving the catheter), it may be important to ensure that the catheter has returned to a safe temperature to prevent damage to the patient's tissue or the catheter/thermocouple. Accordingly, the temperature of the catheter as measured by the thermocouple may be determined and compared to a predetermined threshold representing a safe temperature value. If the temperature exceeds the threshold value, then the computing device may determine that the catheter has thawed, and processing may proceed to step 650. If the temperature does not exceed the threshold value, then the computing device may wait a predetermined amount of time (e.g., one second) and re-read the temperature value from the thermocouple. Exemplary interfaces for validating that the catheter has thawed are depicted in FIGS. 14G-14H.

At step 650, the computing device may determine whether the targeted amount of cryospray calculated in step 635 was successfully delivered. As noted above, at step 640 the computing system may monitor various parameters associated with the catheter and/or thermocouple, which parameters are preferably used to calculate cryospray parameters and, during the application of cryospray, may be used to assess cryospray progress and/or to terminate or interrupt the cryospray if (for example) (a) the temperature drops below a safety threshold, (b) the slope of a temperature curve that the device generates in real time varies (either too high or too low) from a threshold safety range, or (c) if the duration of spray extends beyond a threshold time. If the flow of cryospray is stopped for these or other reasons before the targeted amount of cryospray is delivered, then the computing device may determine at step 650 that the targeted amount of cryospray was not successfully delivered. If step 640 proceeds without interruption, then the computing device may determine at step 650 that the targeted amount of cryospray was successfully delivered.

If the determination at step 650 is "no" (i.e., the targeted amount of cryospray was not successfully delivered), then at step 655 the computing device may determine whether to respray the cryospray. For example, the computing device may present an interface, such as the one depicted in FIG. 14I, for receiving an indication as to whether to respray the cryospray.

If the determination at step 655 is "no" (i.e., the computing device determines that no respray will occur), then processing may proceed to step 660 where the treatment is recorded as a partial spray. For example, a flag may be set in the patient's record indicating that the treatment was incomplete, and optionally indicating a degree of completeness of the treatment.

Returning to step 650, if the determination at step 650 is "yes" (i.e., the targeted amount of cryospray was successfully delivered) and/or if the determination at step 655 was "no" (i.e., the computing system did not determine that a respray should be applied), then processing may proceed to step 665 where the computing system determines whether any more areas remain to be treated. For example, the computing system may read a treatment plan associated with the patient's record, or may present a prompt querying whether additional areas remain to be treated. Alternatively, the computing device may present an interface for receiving a selection of additional areas to be treated, and may further present an option for ending the process in the event that no more areas remain to be treated.

If the determination at step 665 is "yes" (i.e., there are more areas to treat), then processing may return to step 630 and the computing device may receive a new selection of an anatomic region and/or subregion to be treated. The new selection may be the same as a previous selection (i.e., the same area may be selected for multiple treatments). FIGS. 14J-14N depict examples of selections of additional regions and subregions for further treatment.

If the determination at step 665 is "no," (i.e., there are no more areas to treat), then processing may proceed to step 670 and the computing device may end the procedure. As part of step 670, the computing device may generate or alter patient records to indicate the status of any treatments carried out, present prompts instructing the user to remove the catheter from the patient, shut down communication to the catheter, thermocouple, or other parts of the system, and perform any necessary housekeeping steps. Exemplary interfaces for ending the procedure are depicted in FIG. 14O-14P.

One or more of the above-described acts may be encoded as computer-executable instructions executable by processing logic. The computer-executable instructions may be stored on one or more non-transitory computer readable media. One or more of the above described acts may be performed in a suitably-programmed electronic device. FIG.

15 depicts an example of an electronic computing device 700 that may be suitable for use with one or more acts disclosed herein.

The computing device 700 may take many forms, including but not limited to a computer, workstation, server, network computer, Internet appliance, integrated circuit, mobile device, a tablet computer, a smart sensor, custom application specific processing device, etc.

Figure 15:
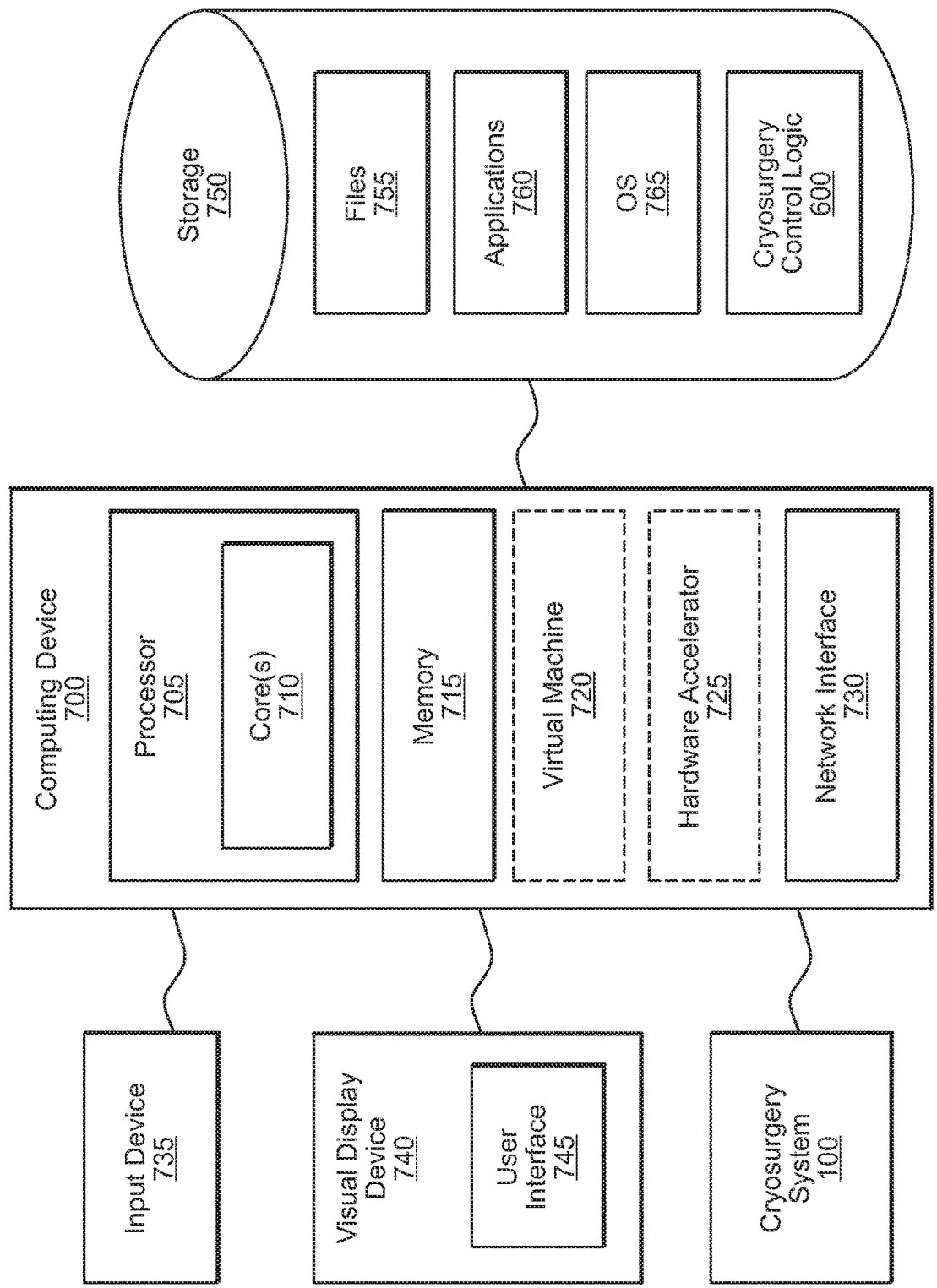
FIG. 15 is a block diagram illustrating an electronic computing device suitable for use with exemplary embodiments.

The computing device 700 is illustrative and may take other forms. For example, an alternative implementation of the computing device 700 may have fewer components, more components, or components that are in a configuration that differs from the configuration of FIG. 15. The components of FIG. 15 and/or other figures described herein may be implemented using hardware based logic, software based logic and/or logic that is a combination of hardware and software based logic (e.g., hybrid logic); therefore, components illustrated in FIG. 15 and/or other figures are not limited to a specific type of logic.

The computing device 700 may include a processor 705. Processors 705 include devices that execute instructions and/or perform mathematical, logical, control, or input/output operations. The processor 705 may include hardware based logic or a combination of hardware based logic and software to execute instructions on behalf of the computing device 700. The processor 705 may include logic that may interpret, execute, and/or otherwise process information contained in, for example, the memory 715. The information may include computer-executable instructions and/or data that may implement one or more embodiments as described herein.

The processor 705 may comprise a variety of homogeneous or heterogeneous hardware. The hardware may include, for example, some combination of one or more processors, microprocessors, field programmable gate arrays (FPGAs), application specific instruction set processors (ASIPs), application specific integrated circuits (ASICs), complex programmable logic devices (CPLDs), graphics processing units (GPUs), or other types of processing logic that may interpret, execute, manipulate, and/or otherwise process the information. Moreover, the processor 705 may include a system-on-chip (SoC) or system-in-package (SiP).

The processor 705 may be a Central Processing Unit (CPU) having one or more processing cores 710. Cores 710 include independent processing units that are physically or logically separate from one another, and that are typically configured to perform parallel processing task. The processor 705 may further include one or more coprocessors, and/or on-chip cache. Such a processor 705 may implement the Complex Instruction Set Computing (CISC) architecture. Examples of such processors 705 include the Celeron®, Pentium®, and Core™ families of processors from Intel Corporation of Santa Clara, Calif., and the Accelerated Processing Unit (APU) and Central Processing Unit (CPU) processors from Advanced Micro Devices (AMD), Inc. of Sunnyvale, Calif.

Alternatively or in addition, the processor 705 of the computing device 700 may be a specialized processor having relatively limited processing capabilities and designed to run in low-power environments. For example, the processor 705 may implement the Reduced Instruction Set Computing (RISC) or Acorn RISC Machine (ARM) architecture. Examples of such processors 705 include the Atom™ family of processors from Intel Corporation of Santa Clara, Calif., the A4 family of processors from Apple, Inc. of Cupertino, Calif., the Snapdragon™ family of processors from Qualcomm Technologies, Inc. of San Diego Calif., and the Cortex® family of processors from ARM Holdings, PLC of Cambridge, England.

The processor 705 may also be a custom processor.

The computing device 700 may include one or more tangible non-transitory computer-readable storage media for storing one or more computer-executable instructions or software that may implement one or more embodiments of the invention.

The non-transitory computer-readable storage media may be, for example, the memory 715 or the storage 750. The memory 715 may comprise a RAM that may include RAM devices that may store the information. The RAM devices may be volatile or non-volatile and may include, for example, one or more DRAM devices, flash memory devices, SRAM devices, zero-capacitor RAM (ZRAM) devices, twin transistor RAM (TTRAM) devices, read-only memory (ROM) devices, ferroelectric RAM (FeRAM) devices, magneto-resistive RAM (MRAM) devices, phase change memory RAM (PRAM) devices, or other types of RAM devices. Examples of memory 715 include Secure Digital™ (SD) memory from the SD Association, as well as Single Inline Memory Modules (SIMMs) and Double Inline Memory Modules (DIMMs) from a variety of manufacturers. The memory 715 may also be a custom memory.

The computing device 700 may include a virtual machine (VM) 720 for executing the instructions loaded in the memory 715. A virtual machine 720 may be provided to handle a process running on multiple processors so that the process may appear to be using only one computing resource rather than multiple computing resources. Virtualization may be employed in the computing device 700 to dynamically share infrastructure and resources in the electronic device. Multiple VMs 720 may be resident on a single computing device 700.

A hardware accelerator 725, may be implemented in an ASIC, FPGA, or some other device. Hardware accelerators 725 include specialized logic implemented in hardware to perform functions that would otherwise be executed more slowly by software. Accordingly, the hardware accelerator 725 may be configured to reduce the general processing time of the computing device 700.

The computing device 700 may include a network interface 730 to interface with a network through one or more types of connections. The network may be, for example, a Local Area Network (LAN), Wide Area Network (WAN) or the Internet. The network interface 730 may be, for example, a network interface controller (NIC) for establishing a wired connection to a computer network, a fiber optic interface for connecting to a fiber optic network, a cable interface for connecting to a cable television network, a telephone jack for connecting to a telephone network, a power-line interface for connecting to a power-line communications network, an area network connection for receiving information on LAN or WAN links (e.g., T1, T3, 56 kb, X.25), a broadband connection for connecting to, for example, an integrated services digital network (ISDN), a Frame Relay connection, an asynchronous transfer mode connection (ATM), wireless connections (e.g., 802.11x-compatible networks), high-speed interconnects (e.g., InfiniBand, gigabit Ethernet, Myrinet), or some combination of any or all of the above.

The network interface 730 may include a built-in network adapter, network interface card, personal computer memory card international association (PCMCIA) network card, card bus network adapter, wireless network adapter, universal serial bus (USB) network adapter, modem or any other device suitable for interfacing the computing device 700 to any type of network capable of communication and performing the operations described herein.

The computing device 700 may include hardware and/or software for connecting to one or more input devices 735, such as a keyboard, a multi-point touch interface, a pointing device (e.g., a mouse), a gyroscope, an accelerometer, a haptic device, a tactile device, a neural device, a microphone, or a camera that may be used to receive input from, for example, a user. Note that the computing device 700 may include hardware or software for interacting with other suitable I/O peripherals.

The input devices 735 may be configured to provide input that is registered on a visual display device 740. A graphical user interface (GUI) 745 may be shown on the display device 740. The GUI 745 may correspond to the GUIs depicted in any of FIGS. 13A-14P. Note that other types of output devices, besides visual display devices, may be employed with the computing device 700.

The computing device 700 may also interface with the cryosurgery system 100 for receiving input from, and providing output to, the cryosurgery system 100. The computing device 700 may issue instructions to the cryosurgery system 100, and may perform any or all of the steps described in FIG. 12. Alternatively or in addition, the computing device 700 may be integral with the cryosurgery system 100.

A storage device 750 may also be associated with the computing device 700. Storage devices 750 include devices that persistently store data on one or more tangible, non-transitory computer-readable mediums. The storage device 750 may store information, including data and/or computer-executable instructions that may implement one or more embodiments of the invention. The information may be executed, interpreted, manipulated, and/or otherwise processed by the processor 705. The storage device 750 may include, for example, a magnetic disk, optical disk (e.g., CD-ROM, DVD player), random-access memory (RAM) disk, tape unit, and/or flash drive.

The storage device 750 (as well as other components depicted in FIG. 15) may be accessible to the processor 705 via an I/O bus.

The storage device 750 may further store files 755, applications 760, and an operating system (OS) 765. Examples of OSes 765 may include the Microsoft® Windows® operating systems, the Unix and Linux operating systems, the MacOS® operating system for Macintosh computers, an embedded operating system, such as the Symbian OS, a real-time operating system, an open source operating system, a proprietary operating system, operating systems for mobile electronic devices, or other operating system capable of running on the electronic device and performing the operations described herein. The operating system 765 may be running in native mode or emulated mode.

Still further, the storage device 750 may store logic for controlling the cryosurgery system 100, such as logic embodying the cryosurgery process 600 described in FIG. 12.

FIG. 13A-L shows a series of Procedure Set-up Screens according to an embodiment of the invention which initiates the steps needed to perform a procedure with the system of the invention. The Procedure Set-up screen may consist of Tank Level Indicator, and various selectable procedure settings, including but not limited to Patient Type selection (e.g., gender, weight-based, age-based, or any other patient category or information that may be used as a basis for delivery of proper cryospray dose), Vent Method, and Egress Reminder selection. The Procedure Set-up screen may also consist of text or symbols to guide the user through the set-up of consumables for the procedure. Once this set-up is complete, the user can proceed to the next screen. Alternatively, if the user is accessing the system to fill the console or to service the console, the user may access those functional screens by selecting a drop-down menu (not shown).

The catheter is scanned by placing the RFID tag on the scanner on the side of the console. When a catheter is successfully scanned, the Catheter ID appears on the screen, and the screen guides the user to the next step. Scanning a catheter initiates the Pre-Cooling process. According to another embodiment, an RFID tag may be provided in a part of the catheter itself, preferably in the connector housing, or "hub", so that it is automatically detected when it is plugged into the console. According to this alternative embodiment, the RFID scanner is placed in the console proximate to the location where the catheter is plugged into the console, so that it automatically reads an RFID that is located in the connector housing of a catheter when a catheter is plugged into the console.

The set up screen contains a list of requirements that must be met prior to moving to the next screen. The list may include but is not limited to:

Vent Method or Gas Egress Path Confirmed—The system acknowledges that the gas egress path has been checked.

Valid Catheter—The system acknowledges the catheter was successfully scanned.

Catheter Inserted—The system detects when the user successfully inserts a catheter into the control panel.

Gender Selected—the system acknowledges that the patient gender has been selected. Any type of patient category that may serve as a basis for delivery of proper cryospray dose may be used, including gender, weight-based, age-based, etc.

When the system is pre-cooling, a state indicator box stating "Precooling System" is displayed.

OK Button—pressing this button enables progression to the next screen, provided all needs have been met. Once all the requirements on the procedure set-up screen are met, pressing the next button takes the user to the Treatment Screen.

Figure 14A:
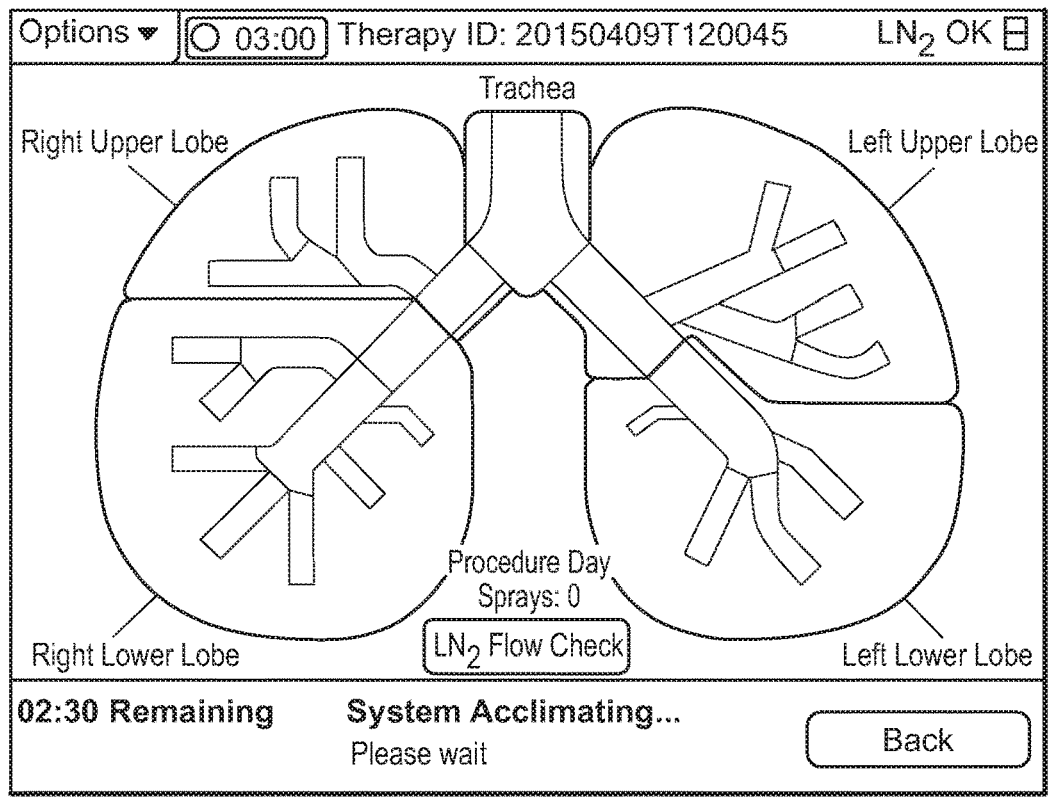
FIGS. 14A-P are exemplary interfaces for performing an ablation procedure in accordance with exemplary embodiments.
Figure 14B:
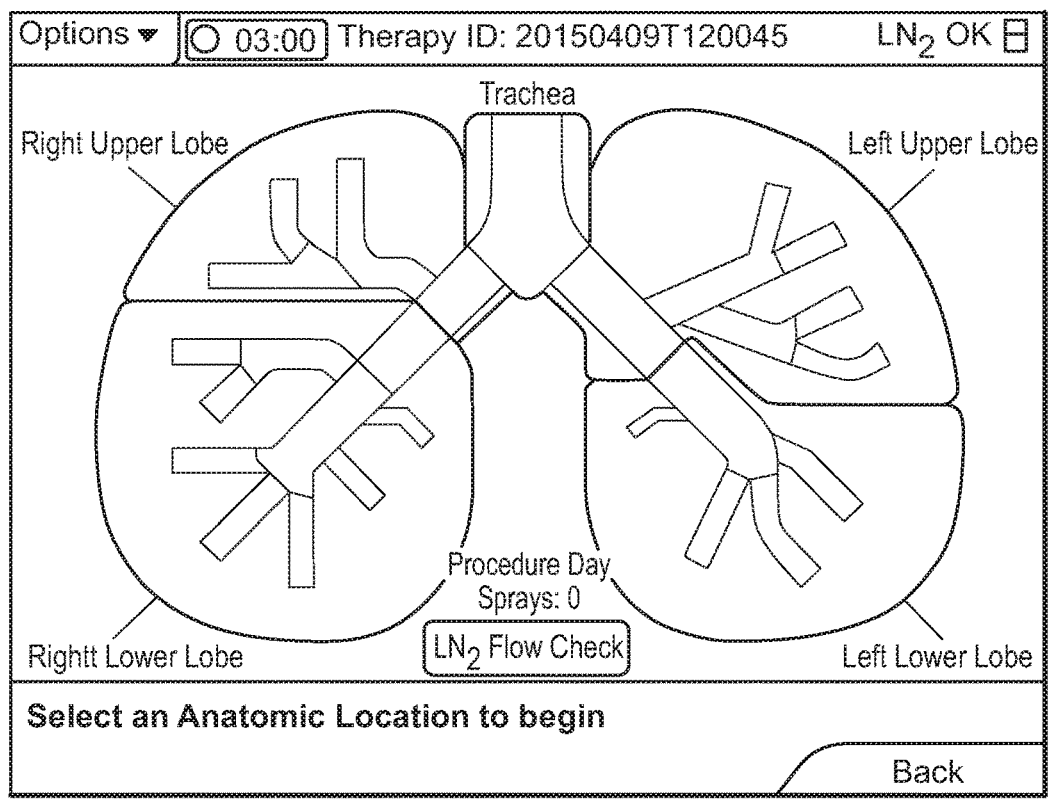
Figure 14C:
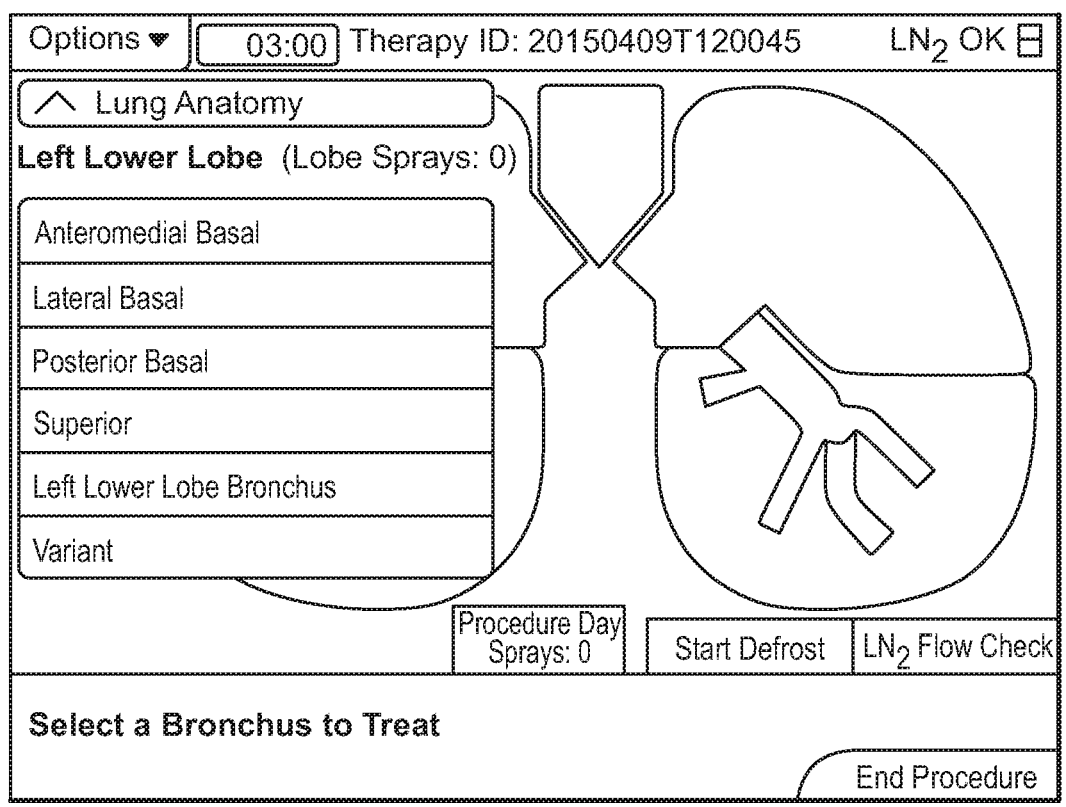
Figure 14D:
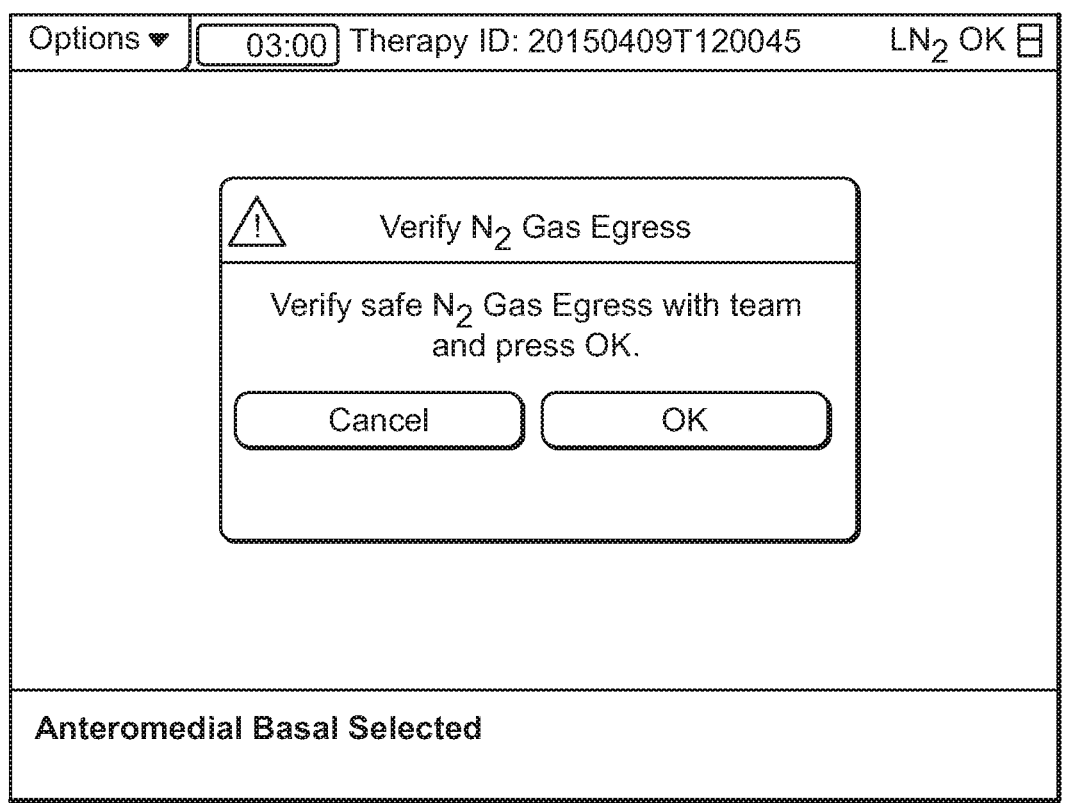
Figure 14E:
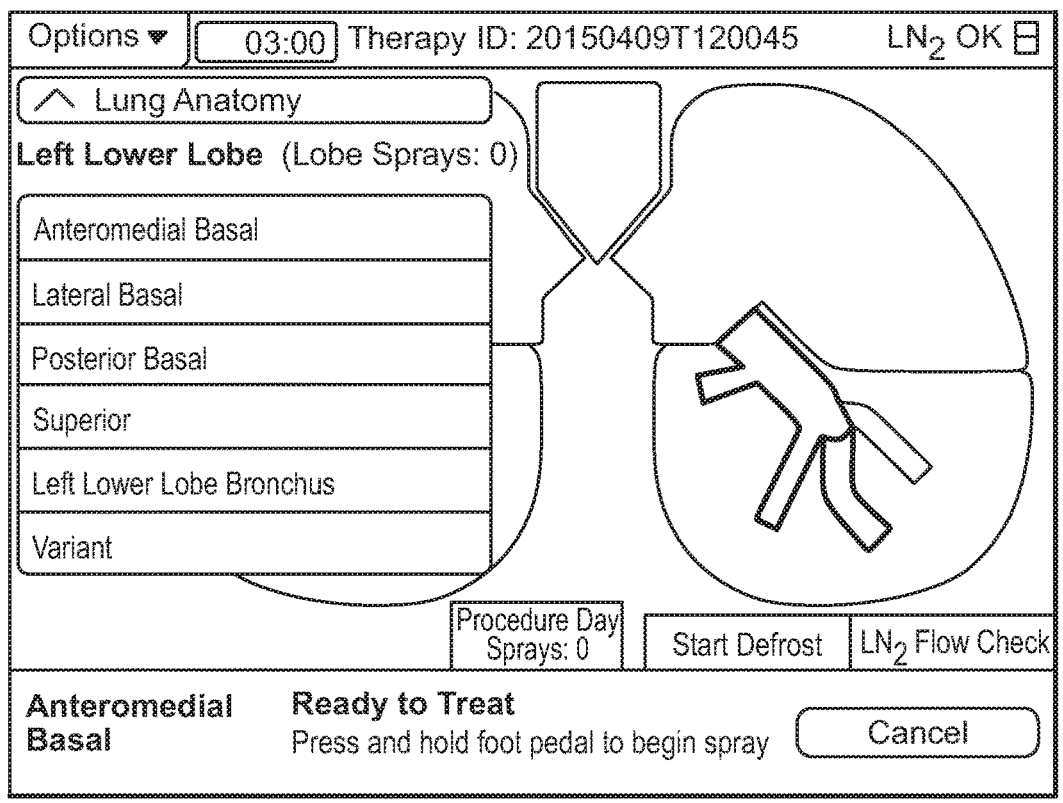
Figure 14F:
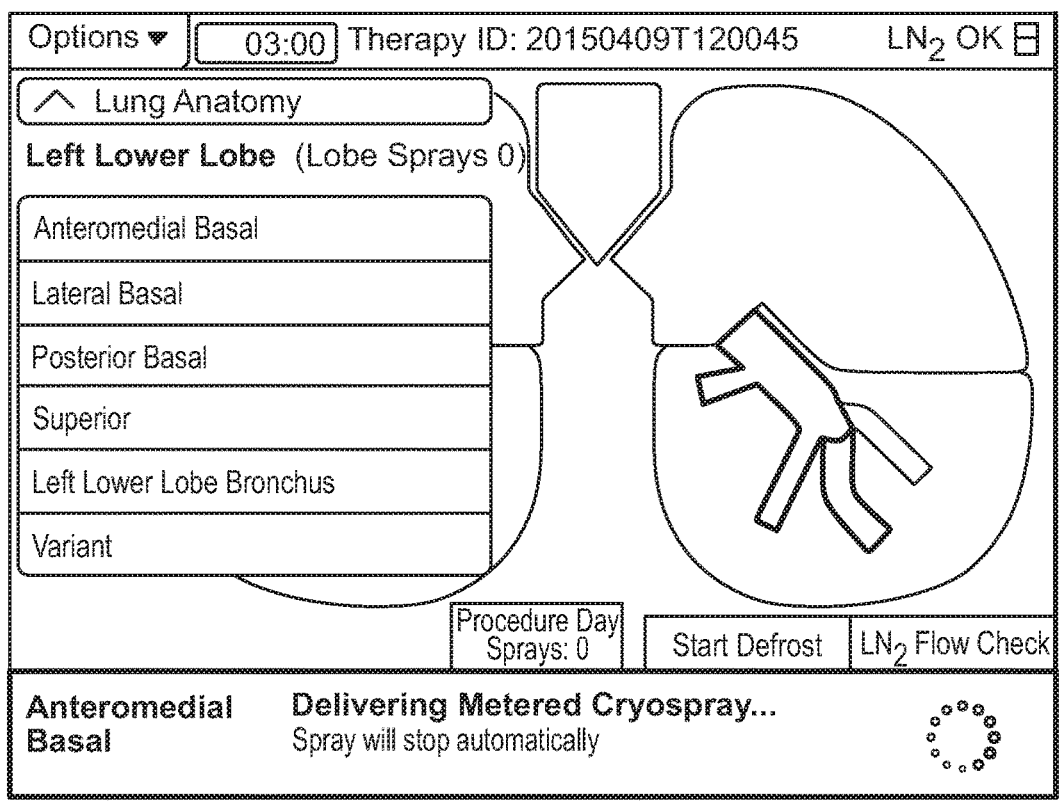
Figure 14G:
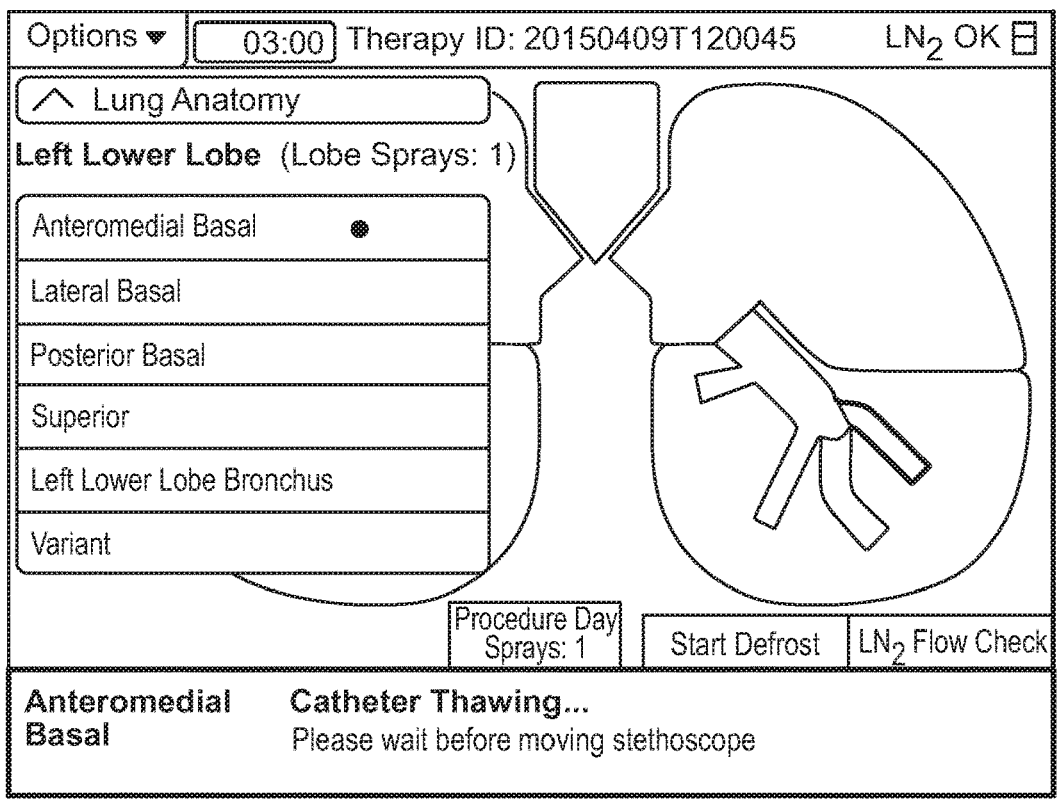
Figure 14H:
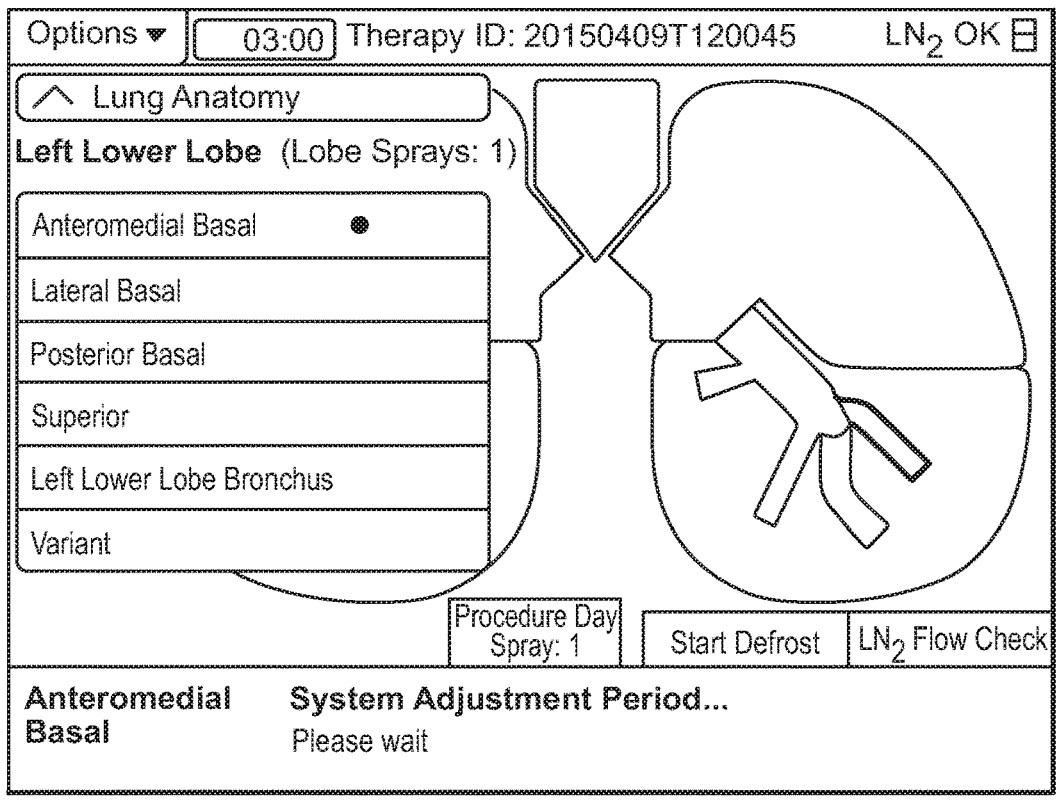
Figure 14I:
Figure 14J:
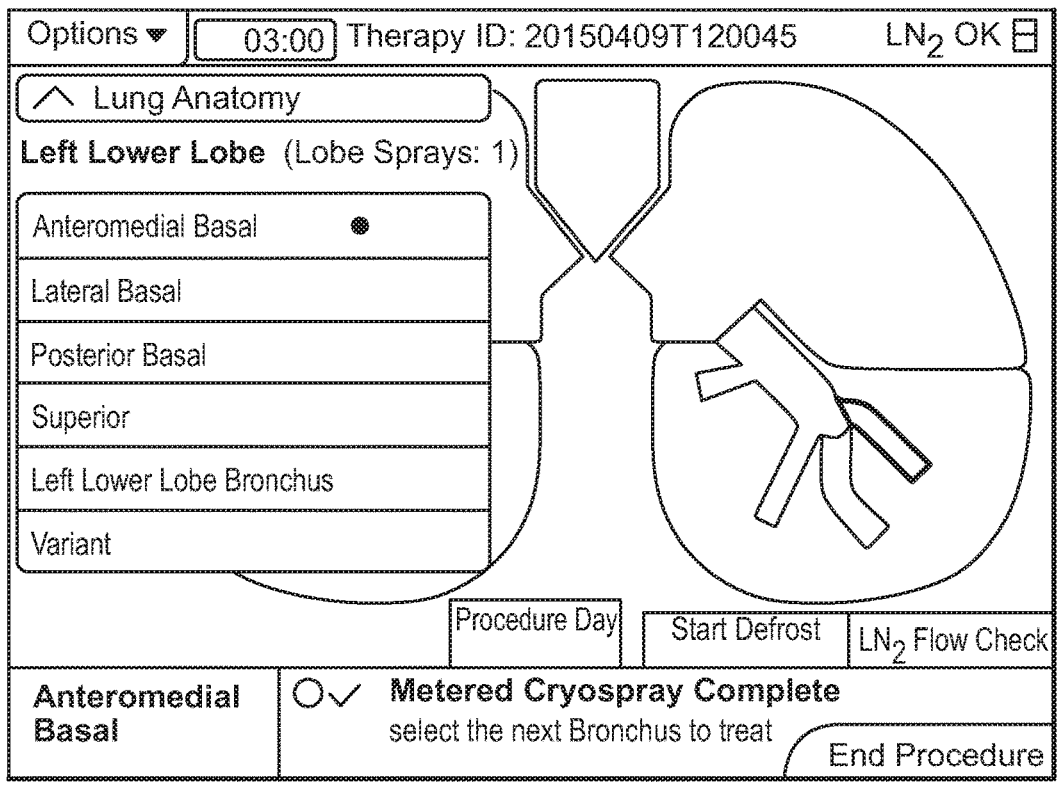
Figure 14K:
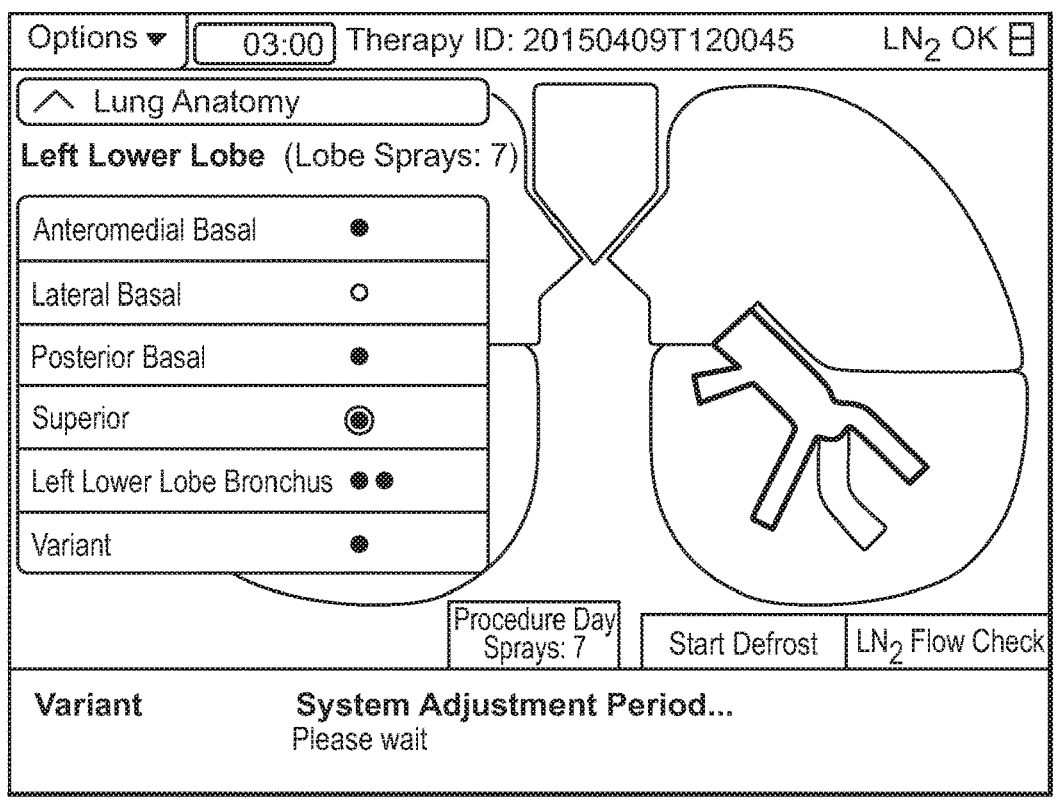
Figure 14L:
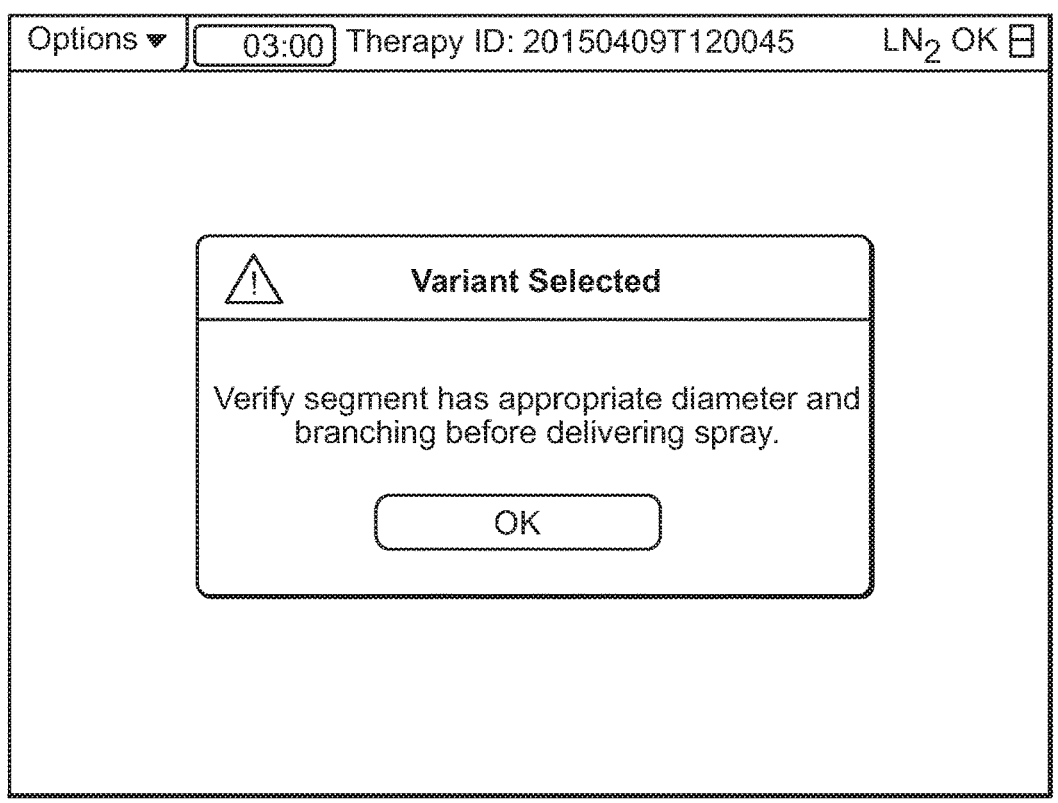
Figure 14M:
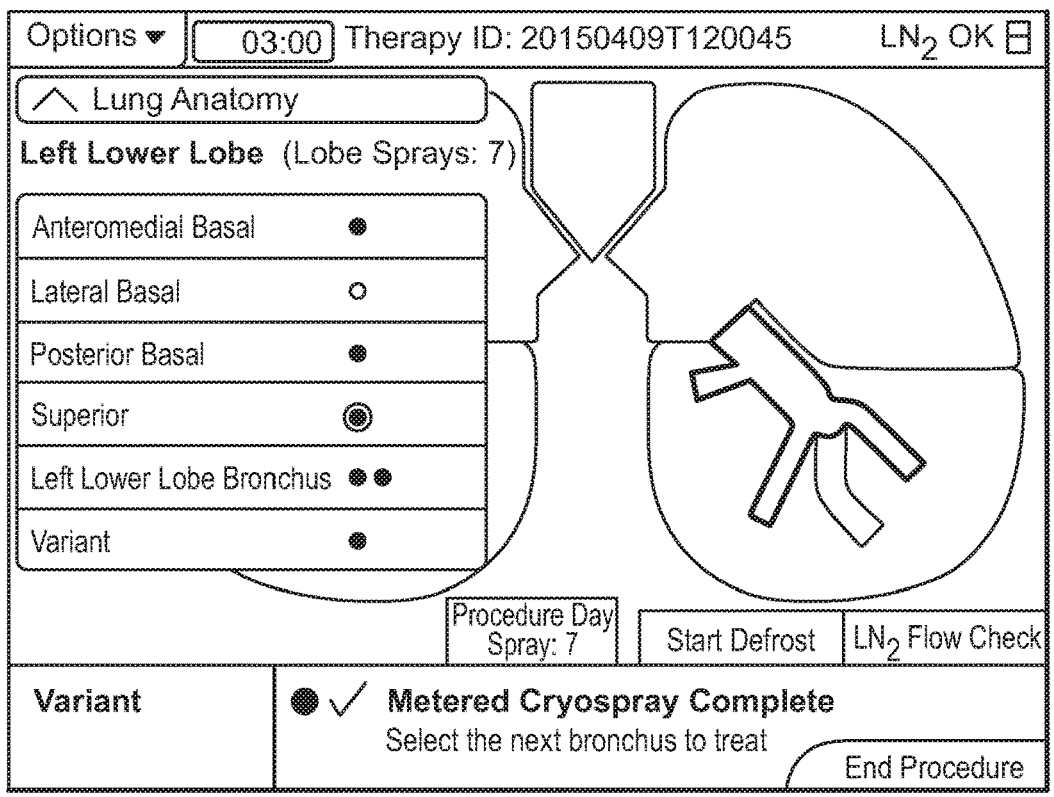
Figure 14N:
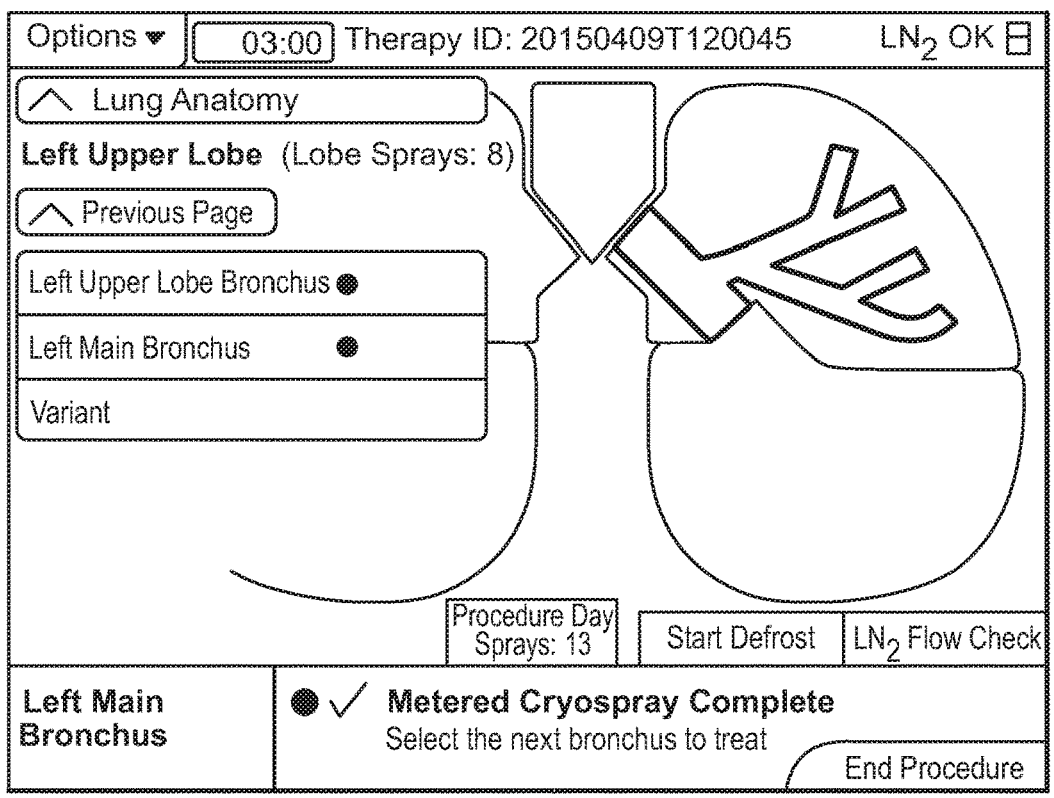
Figure 14O:
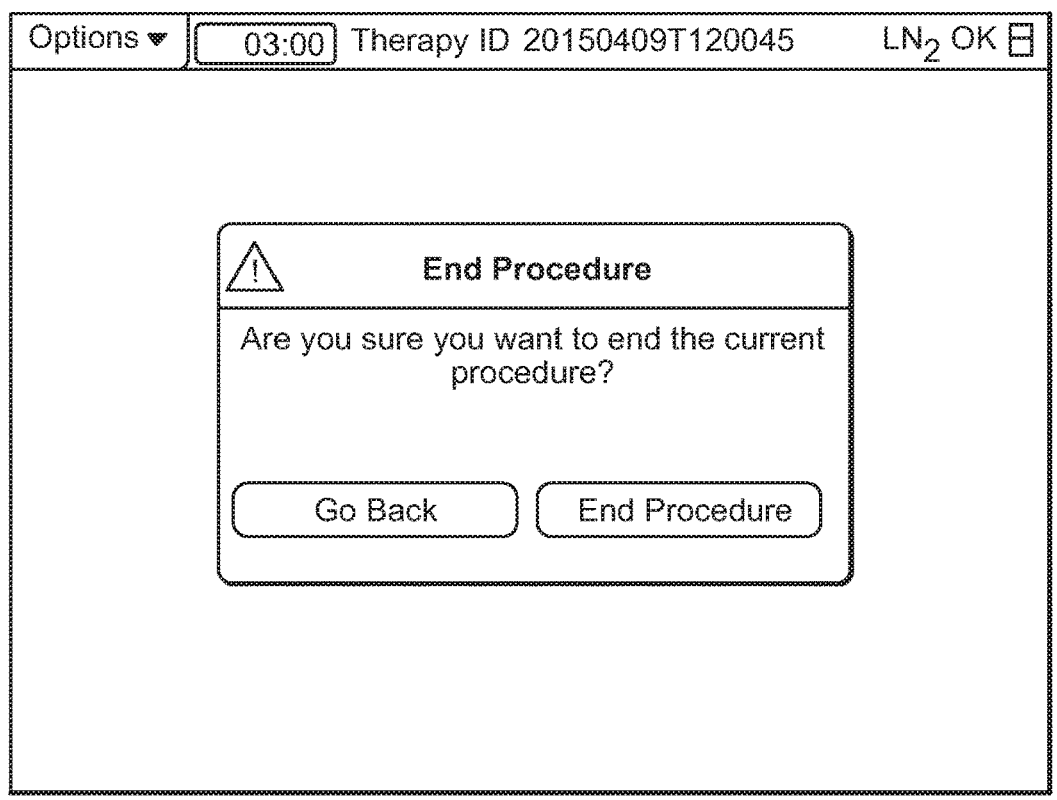
Figure 14P:
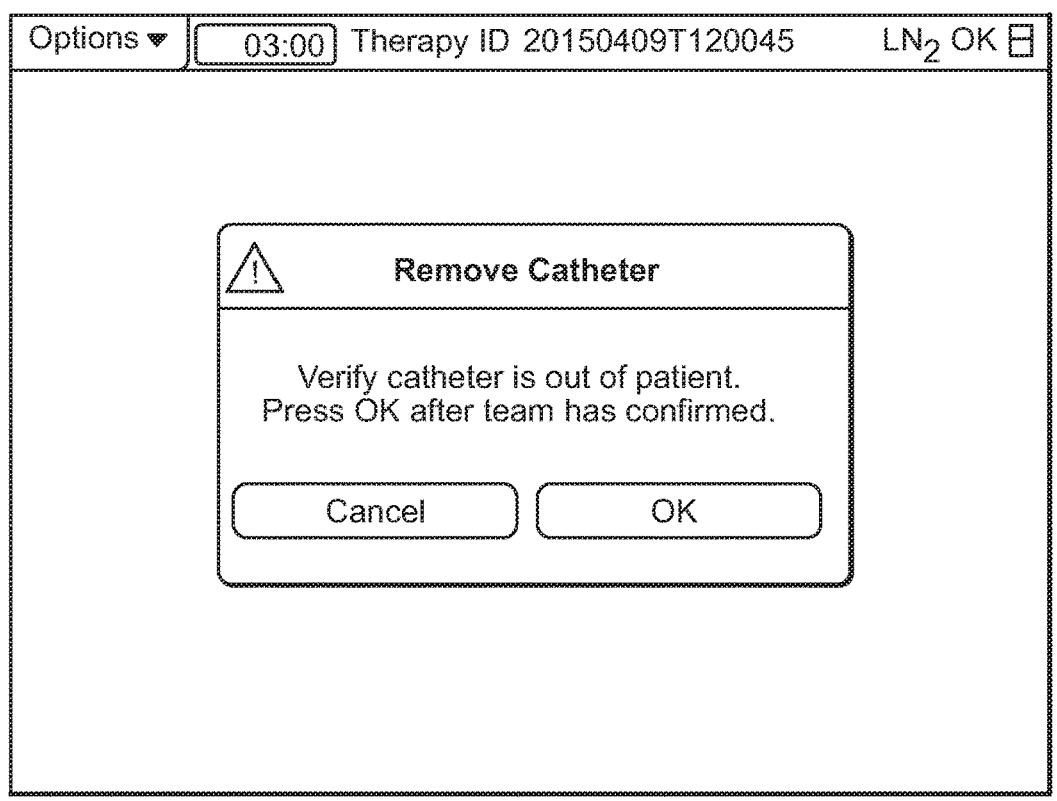

Treatment Screens, shown in FIG. 14A-P guide users through a procedure for lung treatment, generally include a bronchial tree schematic 501 including anatomy labels 503 for each segment that may be treated. Dose location labels 504, dose status indicators 505, cryogen tank volume remaining display 507, total spray indicator 509, state indicators 511, test spray button 513 and defrost button 515. The user selects the dose location label button for the location that will receive the treatment. Selection of one of the label buttons set the dose time for that spray.

When one of the anatomy label buttons is selected, the system automatically sets the dose time for that treatment location and patient gender (or other patient type or category, according to system design).

Once a dose is completed, the first dose status indicator for that treatment site will change colors. The number of dose status indicators for a particular dose location button depends on the length of the segment. For example, the Trachea dose location button 504 shown in FIG. 14 has six dose status indicators 505. This means that there are six potential treatment locations in the trachea. When the Trachea is selected for treatment, the status indicators will change colors one at a time, as each different site in the trachea is completed. If an incomplete dose is delivered, the indicator will not change colors. By contrast, the left bronchial segment #9 location button has only two dose status indicators because it is a much shorter segment and typically requires only two separate doses to cover the entire treatable segment. When a spray dose is initiated, this indicator may count down to zero. Once it reaches zero, the spray automatically stops and an audible beep may sound.

Figure 19A:
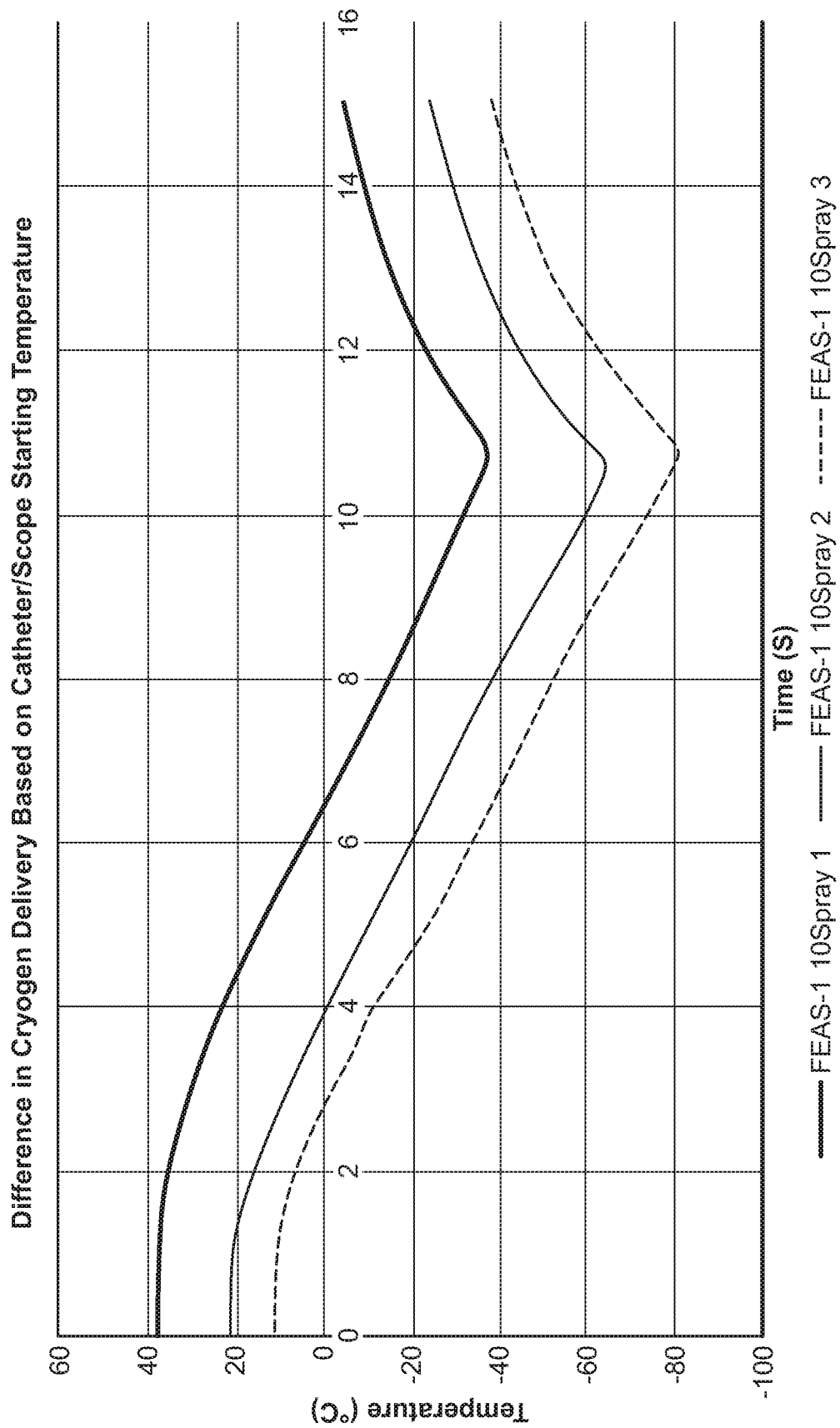
FIG. 19A shows temperature curves obtained in an airway model, as measured on or near the distal tip of the catheter, when identical quantities of cryospray are delivered through catheters with varying starting temperatures.

A thermocouple or other temperature sensing element (e.g. a flex circuit temperature sensor) is preferably disposed on the catheter near the distal tip, to provide temperature information to the console. The temperature information is used in several of processes described above: temperature information is used to determine the quantity of cryospray to be delivered by the system, to determine when the cryospray exits the tip of the catheter and to control the delivery of dosing, and to provide feedback to the system during the delivery of cryospray, as the system is preferably configured to interrupt the flow of cryospray if the measured temperature decreases below a threshold, or if the rate of change of the measured temperature varies from a standard rate of change. As is shown in FIG. 19A, the temperature of the catheter at the time the cryospray is initiated may significantly impact any changes in tissue temperature caused by the cryospray; accordingly, the system may decrease the cryospray dose delivered over the course of a sequence of cryosprays, and this decrease may be caused, at least in part, by a progressive decrease in the catheter temperature over the course of multiple treatments.

Figure 19B:
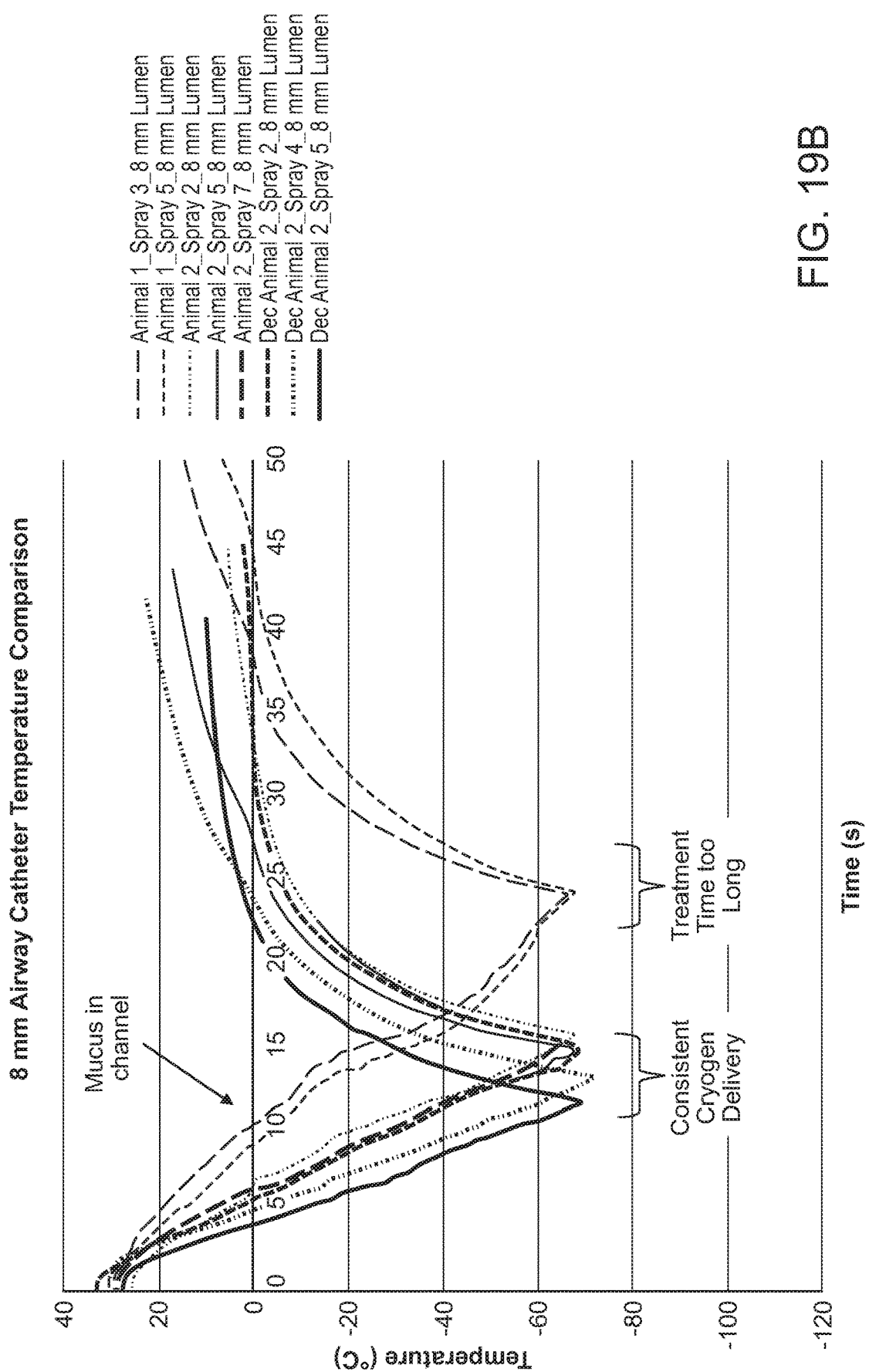
FIG. 19B shows temperature curves in an airway model when identical cryospray volumes are delivered to a dry working channel and a working channel having mucus therewithin.
Figure 20:
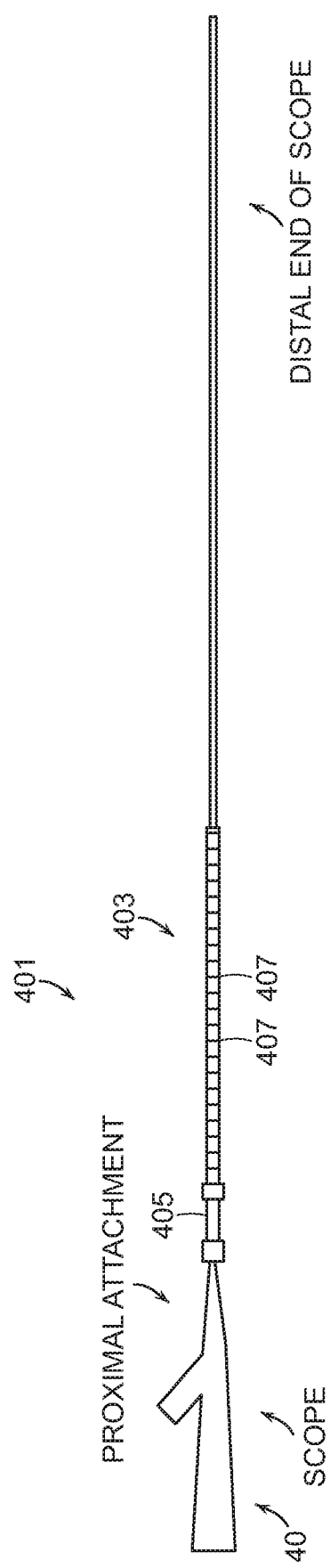
FIG. 20 shows a bronchoscopic measurement sheath according to an embodiment of the invention, loaded onto the proximal end of a bronchoscope

FIG. 19B shows that the rate of temperature change, as measured by a temperature sensor disposed on the catheter, can vary depending on the presence or absence of mucus within the working channel; thus, temperature information of the catheter is used in preferred embodiments is used to assess the rate of temperature change during the delivery of cryospray, and if the rate of change varies beyond a threshold value from a standard rate of change, or if the elapsed time during the cryospray exceeds a threshold time, the system may interrupt the cryospray.

According to certain embodiments, then, the timing of the spray dose may be started from the moment cryospray leaves the catheter, based on feedback from the thermocouple, rather than from the time the user depresses the pedal.

The defrost button may be pressed to facilitate removal of a frozen catheter from a scope or other manipulation tool, if it is necessary to remove it before the catheter would naturally thaw. When the DEFROST button is engaged, the DEFROST Indicator will appear. DEFROST will run for a predetermined amount of time. To interrupt the defrost operation before the predetermined time has elapsed, the user need only press the defrost button a second time.

The Test Spray button may be pressed if the user wants to demonstrate the spray outside of the patient.

The End Procedure button may be pressed once the procedure is complete. Pressing this button may lead the user to a procedure summary report, which may summarize the doses and locations for that procedure day.

Venting of Nitrogen gas is achieved through passive venting. Before beginning treatment and at the discretion of the treating physician, proper passive venting tube type and size should be determined. A rigid bronchoscope or endotracheal vent tube may provide an annular vent area where the scope passes through the center of the tube.

A scope Introducer may be provided in the catheter kit to aid introduction of the catheter into the scope and to reduce catheter kinking. The tapered end of the introducer should be placed approximately 1 cm into the working channel of the scope or until any built in mechanical stop engages into the introducer.

A sheath (referred to herein as a "dose spacing sheath") may be placed on the outer surface of the flexible bronchoscope to aid in discreet placement of doses to prevent overlapping doses when multiple doses are delivered in an anatomical lumen of the same diameter.

A flexible bronchoscope is introduced through the nose or mouth as appropriate and the airway is inspected before starting the procedure. The user then navigates the bronchoscope to the targeted site and positions the bronchoscope so that the targeted treatment site is viewed.

Once the bronchoscope has been advanced to the target treatment site, the catheter may be fed through the introducer and into the working channel of the bronchoscope. Once the catheter has been properly situated at the target site, the user then selects the anatomy location buttons on the Treatment screen, based on which anatomical location will be treated.

Prior to delivering a dose, the system may prompt the user to confirm gas egress path.

To initiate cryospray, the user presses and holds the foot pedal. The system will spray until the earlier of a predetermined temperature is measured by the catheter or a predefined time based on the anatomy and patient type/category/gender screen selections has elapsed.

During the spray, the monitor may count down the time remaining on the dose. Once the dose is complete, the display may indicate the dose is complete, and the user can then move to the next dose location and press the location on the user interface.

If the spray is stopped before an adequate dose is delivered, the system may not acknowledge it as a dose and the user may be advised to redeliver that dose.

Figure 17:
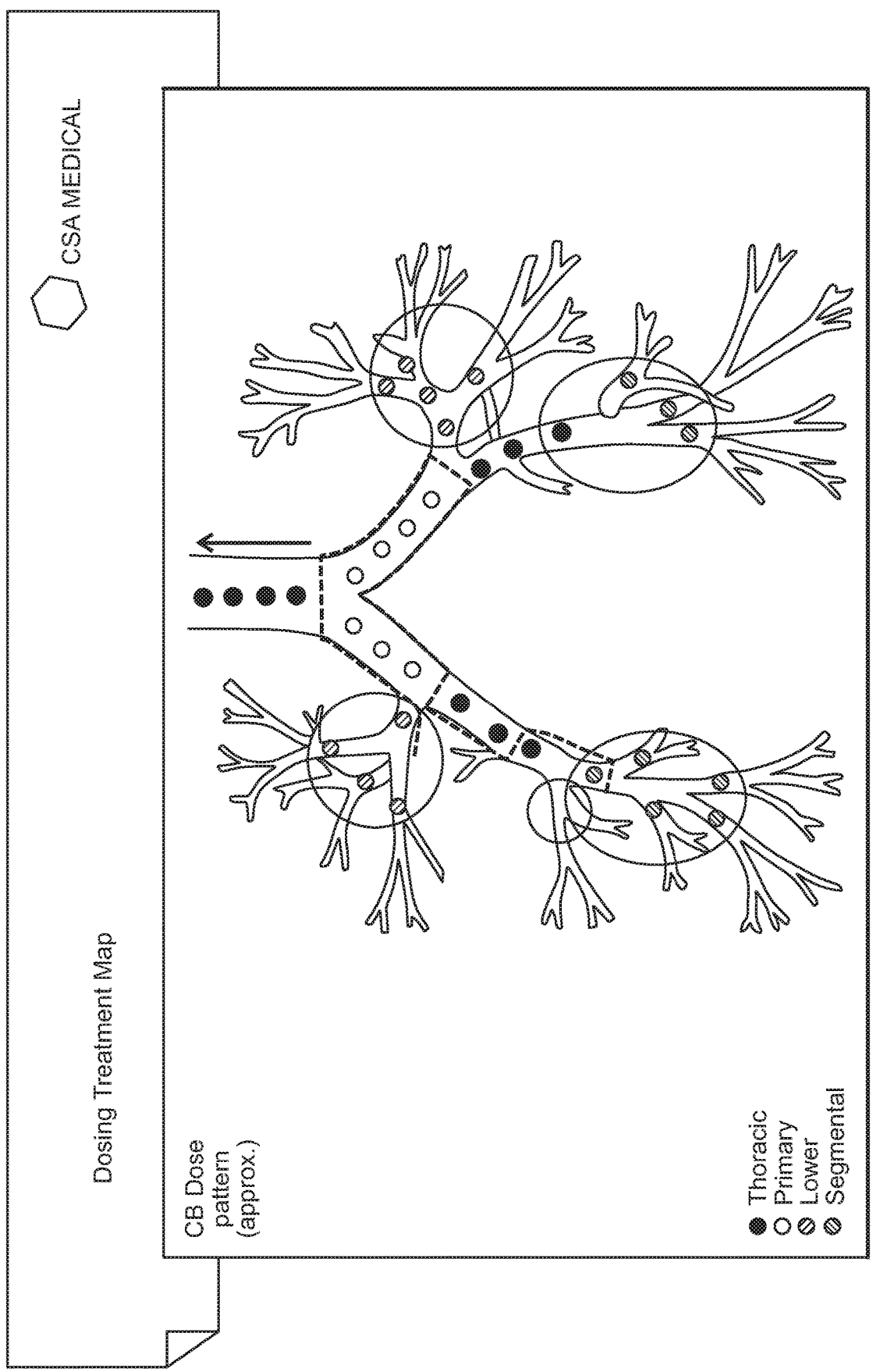
FIG. 17 shows a dose treatment map according to an embodiment of the invention.

As an example of the use of the invention in the right lung, and with reference to FIG. 17, after making the appropriate console gender and anatomic selections, the user would navigate to most distal point of RB9 (Right Lateral basal), activate the spray, then wait for the spray to automatically stop after the prescribed dose, then wait for thaw. The user would then move the catheter and bronchoscope proximally and navigate to RB10 (Right Posterior basal), indicate that treatment location on the user interface, and repeat the procedure steps (i.e., initiate spray, wait for it to automatically stop, then wait for thaw). The user would then move the catheter and bronchoscope proximally to RB8 (Right Anterior basal), and again repeat. The user would then navigate to RB7 (Right Medial basal), and repeat. After spraying the Basal Segments, the user would then move the catheter to the Right Lower Lobe, indicate that treatment location on the user interface, and repeat the procedure steps with the lobar treatment time pre-programmed into the system. In each anatomy location, there may be more than one spray/dose depending on the length of the segment, but no more than one dose/spray on the same site. This may continue until all viable segments, lobar and bronchi locations have been treated.

For segments that are long enough for more than one spray/dose, the user may spray more than one spray/dose, but no more than one dose/spray on the same site. An example in Right Lobar Bronchi, the user would proceed as follows: navigate to most distal point of RLL (Right Lower Lobar), note the marking on the Dose Spacing Sheath relative to a fixed point, e.g. endotracheal tube, spray, thaw, back up using the markings on the Dose Spacing Sheath, spray dose number two in RLL, thaw. Move the catheter and the bronchoscope proximally into the bronchus intermedius. Hand ventilation may be required with or without removing bronchoscope.

In the main bronchi, there may be more than one spray/dose depending on the length of the segment but no more than one dose/spray on the same site. Again, moving the catheter and bronchoscope in a distal-to-proximal direction, and after changing the console anatomic setting to bronchi, the user would note the marking on the Dose Spacing Sheath relative to a fixed point, e.g. endotracheal tube, spray, thaw, back up using the markings on the Dose Spacing Sheath, spray dose number two, thaw and repeat until main bronchi and bronchus intermedius are treated. Hand ventilation may be required with or without removing bronchoscope after a number of doses are given.

In the trachea, there may be more than one spray/dose depending on the length of the trachea, but no more than one dose/spray on the same site. Starting at the main carina, moving the catheter and bronchoscope in a distal to proximal direction note the marking on the Dose Spacing Sheath relative to a fixed point, e.g. endotracheal tube, spray, thaw, back up using the markings on the Dose Spacing Sheath, spray dose two, thaw and repeat until an appropriate length of the trachea is treated. Hand ventilation may be required with or without removing bronchoscope after a number of doses are given.

Bronchoscopic Sheath for Measuring and Spacing

Figure 21:
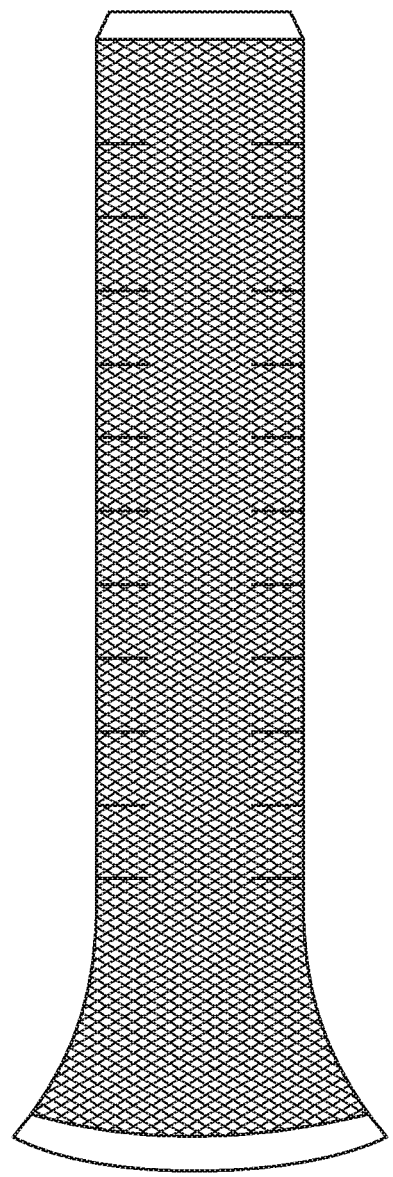
FIG. 21 is a close-up view of a bronchoscopic measurement sheath according to an embodiment of the invention, showing an optional flared proximal end and an optional tapered distal end, with an optional elastomeric cuff at both ends.

Referring to FIG. 21, a bronchoscopic measurement sheath is shown which is configured to be placed over the outer surface of a flexible fiber-optic bronchoscope along a portion of its length during a bronchoscopic procedure. Bronchoscopic measurement sheath 401 may be made of an elongated tube 403 having a lumen configured to receive a bronchoscope 40, a securing device 405, for example a Tuohy-Borst, at one end of said tube configured to secure a proximal end of said sheath to a proximal end of the bronchoscope. According to other embodiment, the securing device is a hub (see, e.g., FIG. 4) fixed to a proximal end of the sheath. The sheath preferably bears a plurality of markings 407 along a portion of the external surface of the tube configured to denote a distance that said scope is moved relative to a fixed position of a patient, a patient feature, or other fixed reference point. Said markings may be circumferential marker bands outside the working channel of the scope and may optionally be associated with printed numbers. When aligned with a venting tube (e.g. rigid bronchoscope or endotracheal tube), the markings provide an extracorporeal proximal reference mark prior to dosing. In subsequent doses or treatments, the reference markers assist the physician when the scope is moved to new treatment locations. In the case of dose spacing, the reference markers assist the physician so as not to overlap doses.

A bronchoscopic measurement sheath may be placed on the outer surface of the flexible bronchoscope to provide reference markings to aid practitioner in measuring movement of the bronchoscope into and out of the patient's airway during diagnostic or therapeutic bronchoscopy A bronchoscopic measurement sheath may be placed on the outer surface of the flexible bronchoscope to aid in discreet placement of doses to prevent overlapping doses when multiple doses are delivered in an anatomical lumen of the same diameter.

FIG. 21 shows a close up of an embodiment of a bronchoscopic measurement sheath according to an embodiment of the invention in which a proximal end of the sheath is cuffed or hubbed and a distal end of the sheath is cuffed and tapered. The optional hub at the proximal end is configured to aid with loading of the sheath onto a bronchoscope, and the optional taper at the distal end is configured to assist with introduction of a sheath-loaded bronchoscope into an endotracheal tube.

According to various embodiments, the sheath may be made of a braided PET (polyethylene terephthalate) polymer monofilament, and the markings are printed on the exterior of the sheath. According to other embodiments, the braid may be made from filaments of other compositions (e.g., polypropylene, nylon, polyester) or the braid may be made from a hybrid of filaments made from PET and other materials. According to a preferred embodiment, the braid is a 72-carrier construction in a 1 over 2 under 2 pattern, the 72 elements comprising 24 elements of 0.0052"PET monofilament at each end, and 48 elements of 85/24 PET multifilament (85 denier/24 filaments). The material may be braided onto a 0.076" acetal substrate core at 38 ppi (pics per inch). According to other embodiments, the braid may be comprised of up to 150 elements of different diameter filaments from 0.004" to 0.01 and up to 50 ppi (pics per inch). Alternatively, the braid is a 26 ppi (measured after construction) braid formed over a 2 mm mandrel, having 12 carriers in each direction (24 total) with 2 ends each of 0.006" (0.015 mm) monofilament and another 12 carriers in each direction (24 total) comprising 440 denier monofilament, and is heat-set at 340° F. (171.1° C.) for five minutes.

As shown in FIG. 21, either or both ends of the sheath may be formed with a cuff or bonded to prevent or inhibit fraying and/or unraveling of the braid and assist in insertion and removal from the scope.

The end cuffs may be a heat-fused end of the braid itself, or it may be a separate elastomeric (e.g., polyurethane, silicon, etc.) or rigid plastic hub fixed or bonded to the end of the braid. In the case a proximal hub is used, it is preferably shaped to fit the tapered portion of the bronchoscope that connects the working end to the hand piece. According to one embodiment, the hub may be a separate elastomeric element that sandwiches the end of the braid. The hub may be affixed to the braid according to any known methods, including heat bonding, joint bonding, ultra violet light cure, adhesive, or mechanical bonding, such as dipping. According to a preferred embodiment, the hub may be formed with an annular recess (see FIG. 4) configured to receive the heat-sealed edge of the braid. Once the end of the braided tube has been inserted into the annular recess of the hub, adhesive may be dispensed to fill the annular space that receives the braid, bonding the braid into the annular recess. As shown in FIG. 21, the distal end may be tapered for atraumatic insertion in anatomy. According to another embodiment, the distal end may be made have greater stiffness than the remainder of the braid to assist with insertion of the bronchoscope and mounted measurement sheath into the sealing gasket of an endotracheal tube or other laryngeal mask airway, preventing the sheath from buckling and retracting on itself and the bronchoscope as it passes through the tight passage.

FIG. 22 shows an embodiment of a bronchoscopic measurement sheath mounted on the proximal end of a bronchoscope. The proximal portion of the braided sheath may be a heat-fused end of the braid itself, or it may have a separate elastomeric (e.g., polyurethane, silicon, etc.) or rigid plastic element fixed to the end of the braid in order to slide the sheath onto the scope and fix it in place (see, e.g., FIGS. 6 and 7). According to a preferred embodiment, the proximal end has a thermoplastic molded component or "hub" (see, e.g., FIG. 4) molded onto the braid and having tapered interior profile to accommodate the tapered junction between the proximal end of the flexible fiber optic bronchoscope (the "working portion") and the handpiece.

Figure 24:
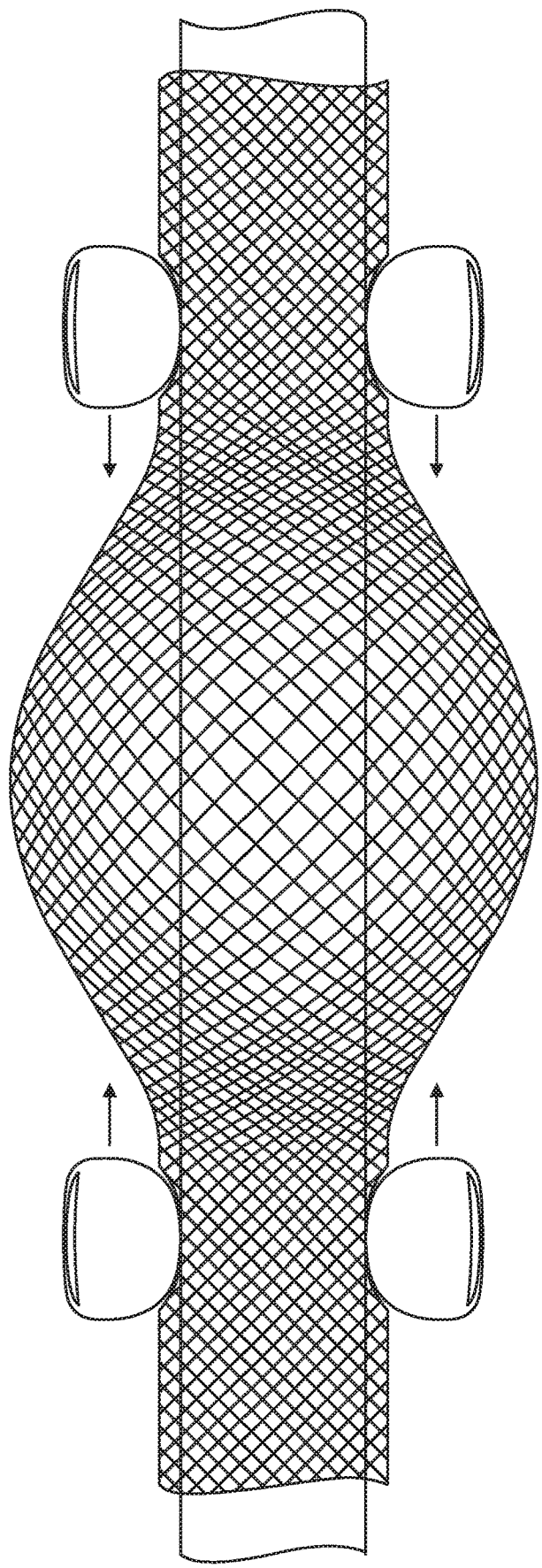
FIG. 24 is a close-up view of a bronchoscopic measurement sheath according to an embodiment of the invention, specifically showing how the sheath expands when the ends are forced together.

FIG. 24 shows how the braid of the sheath is configured to expand and open when the two ends of the sheath are forced together. In order to advance the sheath over the bronchoscope prior to a procedure, or to withdraw the sheath from the bronchoscope after a procedure, the user need only squeeze one end of the sheath tightly against the bronchoscope, and advance the other end toward the fixed end. When the pinched/fixed end is released, the sheath will relax in that direction. However, when one end of the sheath is pulled, the configuration of the braid causes the sheath to tighten tightly around the bronchoscope. Accordingly, the braid of the sheath causes the sheath to work like a Chinese finger puzzle. Accordingly, the sheath will not slide off the bronchoscope as it is being advanced into the endotracheal tube and down a patient's airway. According to a preferred embodiment, the sheath is packaged in a pre-loaded compressed state, so that when it is removed from the packaging for use it is already in the compressed, braid-expanded state which facilitates its application onto the outside surface of the scope.

Figure 25:
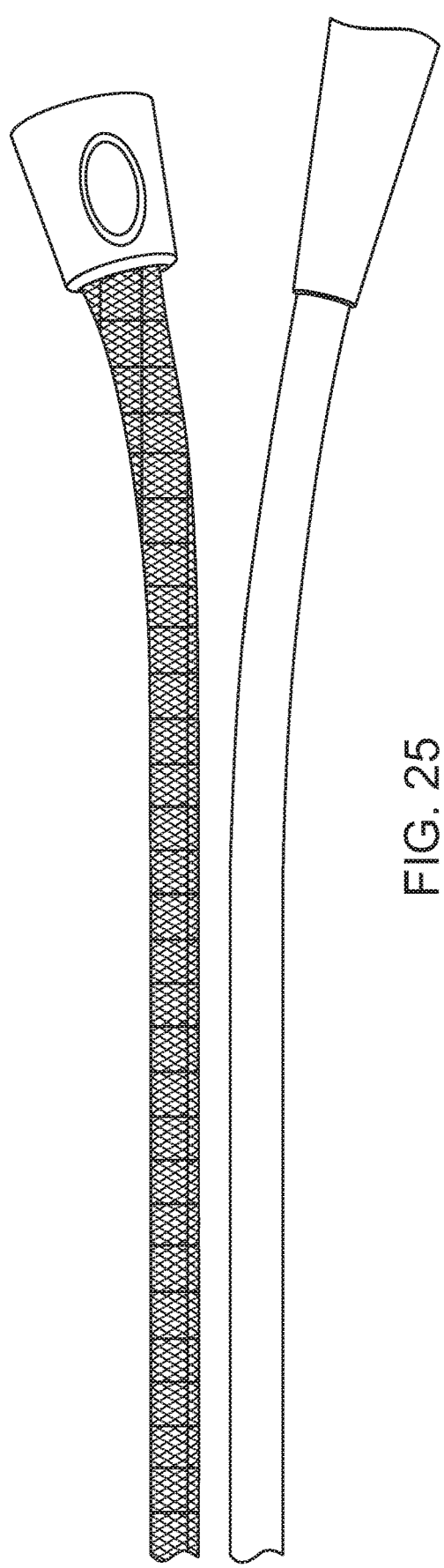
FIG. 25 shows the proximal end of a bronchoscopic measurement sheath according to an embodiment of the invention, next to a flexible bronchoscope.
Figure 26:
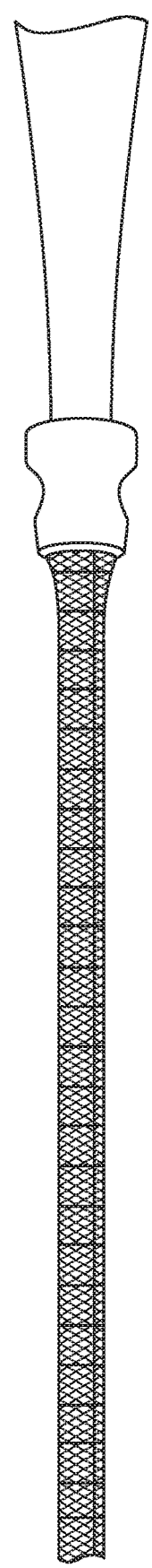
FIG. 26 shows the proximal end of a bronchoscopic measurement sheath according to an embodiment of the invention mounted on the outside of a flexible bronchoscope.

FIG. 25 shows an embodiment of the braided sheath according to the invention, bearing a rigid plastic cuff at the proximal end, next to a flexible bronchoscope onto which it might be loaded. FIG. 26 shows an embodiment of the braided flexible sheath according to the invention loaded onto the outside surface of a flexible bronchoscope, with the rigid plastic cuff at the proximal end of the sheath tightly fitted to the tapered portion of the bronchoscope that connects the working end of the bronchoscope to the handpiece of the bronchoscope.

According to an embodiment of the invention for dose spacing, the invention was initially designed for use in connection with cryospray treatment of a patient's airway using a bronchoscope to allow a user to carefully monitor how far the bronchoscope was being advanced into and/or withdrawn from a patient's airway to ensure that all desired portions of the airway received treatment, but no portion of the airway received more than a single treatment. A flexible bronchoscope is introduced through the nose or mouth as appropriate and the airway is inspected before starting the procedure. The user then navigates the bronchoscope to the targeted site and positions the bronchoscope so that the targeted treatment site is viewed. The dose spacing sheath provides dose spacing guidance when referenced against a fixed reference point such as an endotracheal tube, to allow the bronchoscopist not to dose the same anatomical location more than once.

For example, using the dose spacing sheath to assist with cryospray treatment in Right Lobar Bronchi, the user would navigate sheath-mounted bronchoscope to most distal point of RLL (Right Lower Lobar), noting the marking on the dose spacing sheath relative to a fixed point, e.g. endotracheal tube. The user would then initiate a spray treatment, allow the area to thaw, then withdraw the bronchoscope a discrete distance using the markings on the dose spacing sheath, and then spray a second dose at a second non-overlapping location in the in RLL. The same procedure would be used at any location within the airway to make sure that multiple contiguous or nearly contiguous regions are treated without overlap.

While use of the bronchoscopic measurement sheath and the concept of dose spacing is described herein in the context of cryospray therapy, it can be used for any type of airway treatment in which measure of distance is important.

While use of the bronchoscopic measurement sheath is described herein in the context of airway reference measurement and treatment it can be used for any type of bronchoscopic or endoscopic treatment in which measure of distance is important.

In addition to assisting with dosing, the dose spacing sheath of the invention may be used as a measuring device for any bronchoscopic procedure to document the location of lesions, strictures, treatment sites or length of airway segments.

CONCLUSION

While the examples presented above are focused on treatment of the airway, the systems, methods, and principles illustrated thereby will be understood by skilled artisans to be applicable to cryotherapy of other organ systems and conditions in which delivery of cryogen to a site within a body lumen, including the esophagus, stomach, duodenum, small intestine, large intestine, rectum, uterus, fallopian tube, etc. is desired. Additionally, the automated cryospray systems and catheters described above can be adapted to treat such organ systems, and catheters and systems so adapted, as well as the use of such systems generally, are within the scope of the present invention.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A system comprising:
a source of cryogen in fluid communication with a delivery device for the cryogen;
one or more valves configured to adjust a flow of the cryogen from the source through the delivery device in response to a control signal;
a temperature sensor disposed on the delivery device; and
a controller configured to:
receive temperature information from the temperature sensor;
determine a single dose quantity of the flow of the cryogen based on the temperature information; and
adjust the control signal to the one or more valves based on the determined single dose quantity of the flow of the cryogen to deliver the determined single dose quantity of the flow of the cryogen and to terminate the flow of the cryogen when the determined single dose quantity of the flow of the cryogen is delivered.

2. The system of claim 1, wherein the temperature information is a rate of change of temperature of the temperature sensor measured in real time during the flow of the cryogen.

3. The system of claim 2, wherein the controller is further configured to determine if the rate of change of temperature is within a threshold safety range.

4. The system of claim 3, wherein the controller is further configured to adjust the control signal to terminate the flow of cryogen when the rate of change of the temperature is not within the threshold safety range.

5. The system of claim 1, wherein the controller is further configured to receive a user input of at least one location for treatment and to compare the temperature information received from the temperature sensor to a threshold temperature that is based upon the at least one location for treatment.

6. The system of claim 1, wherein the controller is further configured to measure an elapsed time of the flow of the cryogen from the one or more valves through the delivery device, and compare the elapsed time to a threshold time.

7. The system of claim 1, wherein the temperature information is a cooling power measurement indicative of a cooling power of the delivery device while the delivery device is delivering the flow of the cryogen; and
wherein the controller is further configured to:
receive a pressure measurement of the source of the cryogen corresponding to the cooling power measurement indicative of the cooling power of the delivery device; and
store the pressure measurement as a target pressure.

8. A system comprising:
a source of cryogen in fluid communication with a delivery device for the cryogen;
one or more valves configured to adjust a flow of the cryogen from the source through the delivery device in response to a control signal; and
a controller configured to:
determine a target single dose quantity of the flow of the cryogen;
measure an amount of the cryogen that has been delivered during the flow of the cryogen as a proportion of the target single dose quantity of the flow of the cryogen; and
control the control signal based on the target single dose quantity of the flow of the cryogen and the measured amount of the cryogen to deliver the target single dose quantity of the flow of the cryogen.

9. The system of claim 8, wherein the controller is further configured to control the control signal to terminate the flow of the cryogen when the amount of the cryogen measured substantially matches the target single dose quantity of the flow of the cryogen.

10. The system of claim 8, wherein the amount of the cryogen measured is a function of an amount of time elapsed at a certain rate of the flow of the cryogen.

11. The system of claim 8, wherein the controller is further configured to record a partial delivery of the target single dose quantity of the flow of the cryogen when the amount of the cryogen measured is less than the target single dose quantity of the flow of the cryogen and greater than zero.

12. The system of claim 8, wherein the controller is further configured to record that no flow of the cryogen was delivered when the amount of the cryogen measured is substantially zero.

13. The system of claim 11, wherein the controller is further configured to control the control signal to continue the flow of cryogen against the target single dose quantity of the flow of the cryogen when the amount of the cryogen measured is less than the target single dose quantity of the flow of the cryogen.

14. The system of claim 8, wherein the target single dose quantity of the flow of the cryogen is based on a user input.

15. The system of claim 14, wherein the user input includes an identified segment of an airway.

16. A system comprising:
a delivery device for delivering a spray of a cryogen for treatment of at least one spray location;
a source of the cryogen in fluid communication with the delivery device; and
a controller comprising a user interface, the controller configured to:
receive an input from a user of a patient-type identification and the at least one spray location prior to the treatment, a single dose quantity of the cryogen determinable from the input;
control a flow of the cryogen from the delivery device during the treatment at the at least one spray location; and
determine when the treatment at the at least one spray location should be terminated based on a measured quantity of the flow of the single dose quantity of cryogen.

17. The system of claim 16, wherein the determination is based on a treatment plan associated with the patient-type identification.

18. The system of claim 16, wherein the determination is based on the at least one spray location.

19. The system of claim 16, wherein the at least one spray location comprises an anatomic region and an anatomic sub-region.

20. The system of claim 16, wherein the controller is further configured to alter a patient record to indicate a status of the treatment performed.

* * * * *